(12) United States Patent
Patolsky et al.

(10) Patent No.: US 10,948,451 B2
(45) Date of Patent: Mar. 16, 2021

(54) ELECTROCHEMICAL DETECTION OF NITRO-CONTAINING COMPOUNDS

(71) Applicant: Ramot at Tel-Aviv University Ltd., Tel-Aviv (IL)

(72) Inventors: Fernando Patolsky, Rehovot (IL); Vadim Krivitsky, Bney-Ayish (IL); Boris Filanovsky, Bat-Yam (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/008,218

(22) Filed: Jun. 14, 2018

(65) Prior Publication Data

US 2018/0372673 A1    Dec. 27, 2018

Related U.S. Application Data

(60) Provisional application No. 62/519,934, filed on Jun. 15, 2017.

(51) Int. Cl.
*G01N 33/22* (2006.01)
*G01N 27/403* (2006.01)
*G01N 27/404* (2006.01)
*G01N 33/00* (2006.01)
*G01N 27/30* (2006.01)

(52) U.S. Cl.
CPC ....... *G01N 27/4045* (2013.01); *G01N 27/304* (2013.01); *G01N 27/308* (2013.01); *G01N 33/0057* (2013.01)

(58) Field of Classification Search
None
See application file for complete search history.

(56) References Cited

U.S. PATENT DOCUMENTS

| | | | |
|---|---|---|---|
| 3,389,963 A | 6/1968 | Baumgartner et al. | |
| 4,299,682 A | 11/1981 | Oda et al. | |
| 4,647,359 A | 3/1987 | Lindstrom | |
| 4,795,542 A | 1/1989 | Ross et al. | |
| 5,480,808 A | 1/1996 | Kauffman et al. | |
| 5,795,453 A | 8/1998 | Gilmartin | |

(Continued)

FOREIGN PATENT DOCUMENTS

| | | |
|---|---|---|
| CN | 101241105 | 8/2008 |
| CN | 103323516 | 9/2013 |

(Continued)

OTHER PUBLICATIONS

Bratin et al. "Determination of Nitro Aromatic, Nitramine, and Nitrate Ester Explosive Compounds in Explosive Mixtures and Gunshot Residue by Liquid Chromatography and Reductive Electrochemical Detection", Analytica Chimica Acta, 130(2): 295-311, Oct. 1981.

(Continued)

*Primary Examiner* — Paul S Hyun

(57) ABSTRACT

A carbon electrode having a functional moiety that forms a charge-transfer complex with a nitro-containing compound covalently attached to a surface of the electrode, and a process of preparing such an electrode are provided. Also provided are sensing systems integrating the carbon electrode and methods utilizing same for electrochemical detection of nitro-containing compounds.

20 Claims, 26 Drawing Sheets

Figure 1:
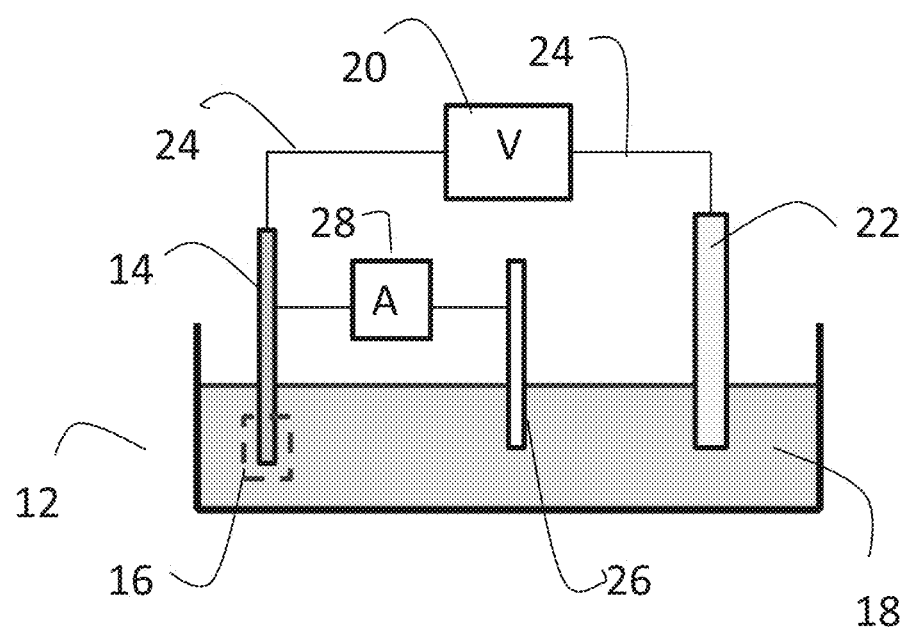

(26 of 26 Drawing Sheet(s) Filed in Color)

(56) References Cited

U.S. PATENT DOCUMENTS

| | | | |
|---|---|---|---|
| 5,897,758 A | 4/1999 | Musacchio et al. | |
| 6,129,831 A | 10/2000 | Temmerman et al. | |
| 6,309,535 B1 | 10/2001 | Williams et al. | |
| 6,872,786 B2 | 3/2005 | Murray et al. | |
| 7,244,345 B1 | 7/2007 | Filanovsky | |
| 7,824,619 B1* | 11/2010 | Aviram | G01N 33/0057 422/88 |
| 8,178,357 B2 | 5/2012 | Trogler et al. | |
| 8,968,825 B1 | 3/2015 | Kawde et al. | |
| 2003/0168338 A1* | 9/2003 | Gao | C12Q 1/004 204/471 |
| 2005/0051440 A1 | 3/2005 | Simpson et al. | |
| 2006/0193750 A1 | 8/2006 | Filanovsky et al. | |
| 2006/0231420 A1* | 10/2006 | Garzon | G01N 27/4074 205/775 |
| 2007/0131566 A1* | 6/2007 | Filanovsky | G01N 27/4045 205/780.5 |
| 2009/0142649 A1* | 6/2009 | Fernandez Lopez | C12N 11/14 429/401 |
| 2009/0275143 A1 | 11/2009 | Misra et al. | |
| 2010/0000882 A1 | 1/2010 | Wang et al. | |
| 2010/0040863 A1 | 2/2010 | Li | |
| 2010/0112546 A1 | 5/2010 | Lieber et al. | |
| 2010/0187108 A1 | 7/2010 | Matsumoto et al. | |
| 2010/0227382 A1 | 9/2010 | Lieber et al. | |
| 2010/0297776 A1 | 11/2010 | Trogler et al. | |
| 2011/0033869 A1 | 2/2011 | Bertin | |
| 2011/0140885 A1 | 6/2011 | Hummer et al. | |
| 2011/0162977 A1* | 7/2011 | Lafitte | G01N 27/48 205/775 |
| 2011/0180764 A1 | 7/2011 | Takahashi et al. | |
| 2011/0306699 A1 | 12/2011 | Whang et al. | |
| 2012/0037513 A1 | 2/2012 | Lindemann | |
| 2013/0115705 A1* | 5/2013 | Patolsky | G01N 27/4146 436/106 |
| 2013/0144131 A1 | 6/2013 | Wang et al. | |
| 2014/0275597 A1* | 9/2014 | Zhang | C07F 7/1896 556/418 |
| 2016/0061775 A1 | 3/2016 | Zabetakis et al. | |
| 2016/0095547 A1 | 4/2016 | Wang et al. | |
| 2017/0226647 A1 | 8/2017 | Benetton et al. | |
| 2017/0243911 A1 | 8/2017 | Patolsky et al. | |
| 2018/0045678 A1 | 2/2018 | Dressick et al. | |
| 2018/0364209 A1 | 12/2018 | Patolsky et al. | |
| 2020/0025736 A1 | 1/2020 | Patolsky et al. | |

FOREIGN PATENT DOCUMENTS

| | | |
|---|---|---|
| CN | 103852512 | 6/2014 |
| CN | 103983680 | 8/2014 |
| CN | 105738440 | 7/2016 |
| WO | WO 2005/050157 | 6/2005 |
| WO | WO 2006/090401 | 8/2006 |
| WO | WO 2007/029245 | 3/2007 |
| WO | WO 2011/000443 | 1/2011 |
| WO | WO 2011/154939 | 12/2011 |
| WO | WO 2012/049616 | 4/2012 |
| WO | WO 2014/111944 | 7/2014 |
| WO | WO 2015/059704 | 4/2015 |
| WO | WO 2017/030930 | 2/2017 |
| WO | WO 2017/098518 | 6/2017 |
| WO | WO 2018/229780 | 12/2018 |
| WO | WO 2018/229781 | 12/2018 |

OTHER PUBLICATIONS

Buckshire "An Overview of Carbon Fiber Electrodes Used in Neurochemical Monitoring", Thesis Submitted to the Graduate Faculty of Arts and Sciences in Partial Fulfillment of the Requirements for the Degree of Master of Science, Chemistry, University of Pittsburgh, USA, p. 1-34, Jun. 13, 2008.

Butler et al. "Removal of Dissolved Oxygen From Water: A Comparison of Four Common Techniques", Talanta, 41(2): 211-215, Feb. 1994.

Chaki et al. "Single Phase Preparation of Monodispersed Silver Nanoclusters Using a Unique Electron Transfer and Cluster Stabilising Agent, Triethylamine", Chemical Communications, 2002(1): 76-77, Advance Publication Dec. 11, 2001.

Chaubey et al. "Mediated Biosensors", Biosensors & Bioelectronics, 17(6-7): 441-456, Jun. 26, 2002.

Chen et al. "Determination of Explosives Using Electrochemically Reduced Graphene". Chemistry—An Asian Journal, 6(5): 1210-1216, Published Online Mar. 8, 2011.

Chen et al. "Poly[Meso-Tetrakis(2-Thienyl)Pophyrin] for the Sensitive Electrochemical Detection of Explosives", Sensors and Actuators B: Chemical, 147(1): 191-197, Available Online Mar. 17, 2010.

Cizek et al. "Integrated Explosive Preconcentrator and Electrochemical Detection System for 2,4,6-Trinitrotoluene (TNT) Vapor", Analytica Chimica Acta, 661(1): 117-121, Available Online Dec. 16, 2009.

Dubnikova et al. "Novel Approach to the Detection of Triacetone Triperoxide (TATP): Its Structure and Its Complexes With Ions", The Journal of Physical Chemistry A, 106(19): 4951-4956, Apr. 18, 2002.

Dwivedy et al. "Charge-Transfer Complexes of 2,4,6-Trinitrotoluene and M-Dinitrobenzene With Some Amines", Journal of Chromatography A, 29(1): 120-125, Jul. 1967.

Engel et al. "Supersensitive Detection of Explosives by Silicon Nanowire Arrays", Angewandte Chemie, International Edition, 49(38): 6830-6835, Sep. 10, 2010.

Eren et al. "Determination of Peroxide-Based Explosives With Copper(II)-Nepcuproine Assay Combined With a Molecular Spectroscopic Sensor", The Analyst, 135(8): 2085-2091, Published Online Jun. 7, 2010.

Filanovsky et al. "Carbon Electrodes Modified With TiO2/Metal Nanoparticles and Their Application to the Detection of Trinitrotoluene", Advanced Functional Materials, 17(9): 1487-1492, Published Online Apr. 18, 2007.

Galik et al. "Cyclic and Square-Wave Voltammetric Signatures of Nitro-Containing Explosives", Electroanalysis, 23(5): 1193-1204, May 2011.

Grigoriants et al. "Electrochemical Reduction of Trinitrotoluene on Core-Shell Tin-Carbon Electrodes", Electrochimica Acta, 54(2): 690-697, Available Online Jul. 11, 2008.

Guo et al. "Porphyrin Functionalized Graphene for Sensitive Electrochemical Detection of Ultratrace Explosives", Electroanalysis, 23(4): 885-893, Apr. 2011.

Laine et al. "Analysis of Hydrogen Peroxide and an Organic Hydroperoxide Via the Electrocatalytic Fenton Reaction", Microchemical Journal, 91(1): 78-81, Available Online Aug. 22, 2008.

Laine et al. "Electrochemical Detection of Triacetone Triperoxide Employing the Electrocatalytic Reaction of Iron(II/III)-Ethylenediaminetetraacetate and Hydrogen Peroxide", Analytica Chimica Acta, 608: 56-60, Published Online Dec. 8, 2007.

Lichtenstein et al. "Supersensitive Fingerprinting of Explosives by Chemically Modified Nanosensors Arrays", Nature Communications, 5: 4195-1-4195-12, Jun. 24, 2014.

Lu et al. "Highly Sensitive Electrochemical Detection of Trace Liquid Peroxide Explosives at a Prussian-Blue 'Artificial-Peroxide' Modified Electrode", The Analyst, 131(12): 1279-1281, Published in Advance Oct. 12, 2006.

Marinovic et al. "The Electrochemical Reduction of Trinitrotoluene on a Platinum Wire Modified by Chemisorbed Acetonitrile", Journal of Electroanalytical Chemistry, 648(1): 1-7, Available Online Jul. 15, 2010.

Munoz et al. "'One-Step' Simplified Electrochemical Sensing of TATP Based on Its Acid Treatment", The Analyst, 132(6): 560-565, Published in Advance Apr. 30, 2007.

Parajuli et al. "Sensitive Determination of Hexamethylene Triperoxide Diamine Explosives, Using Electrogenerated Chemiluminescence Enhanced by Silver Nitrate", Analytical Chemistry, 81(13): 5267-5272, Published on Web Jun. 10, 2009.

(56) References Cited

OTHER PUBLICATIONS

Schulte-Ladbeck et al. "A Field Test for the Detection of Peroxide-Based Explosives", The Analyst, 127(9): 1152-1154, Published in Advance Aug. 16, 2002.
Schulte-Ladbeck et al. "Determination of Triacetonetriperoxide in Ambient Air", Analytica Chimica Acta, 482(2): 183-188, Apr. 15, 2003.
Schulte-Ladbeck et al. "Trace Analysis of Peroxide-Based Explosives", Analytical Chemistry, 75(4): 731-735, Published on Web Jan. 15, 2003.
Sheppard et al. "Electrochemical and Microscopic Characterisation of Platinum-Coated Perfluorosulfonic Acid (Nafion 117) Materials", Analyst, 123(10): 1923-1929, 1998.
Spalek et al. "Kinetics of the Decomposition of Hydrogen Peroxide in Alkaline Solutions", Journal of the Chemical Society, Faraday Transactions I: Physical Chemistry in Condensed Phases, 78(8): 2349-2359, 1982.
Wang et al. "A Single-Walled Carbon Nanotube Network Gas Sensing Device", Sensors, 11(8): 7763-7772, Aug. 8, 2011.
Weiss "The Catalytic Decomposition of Hydrogen Peroxide on Different Metals", Transactions of the Faraday Society, 31: 1547-1557, 1935.
Xie et al. "Selective and Rapid Detection of Triacetone Triperoxide by Double-Step Chronoamperometry", Microchemical Journal, 94(2): 166-170, Available Online Oct. 31, 2009.
Zang et al. "Electrochemical Detection of Ultratrace Nitroaromatic Explosives Using Ordered Mesoporous Carbon", Analytica Chimica Acta, 683(2): 187-191, Available Online Oct. 20, 2010.
Zhao et al. "Electrocatalytic Reduction of Hydrogen Peroxide by Iron-Adenosine Nucleotide Complexes", Journal of Electroanalytical Chemistry, 379(1-2): 501-503, Dec. 12, 1994.
"Hydrogen Peroxide Sensor Based on Carbon Paste Electrode Containing a Metal Porphyrin Complex", Chemical Sensors, 17: Supplement B, 427-429, 2001.
International Search Report and the Written Opinion dated Oct. 10, 2018 From the International Searching Authority Re. Application No. PCT/IL2018/050665. (12 Pages).
International Search Report and the Written Opinion dated Oct. 11, 2018 From the International Searching Authority Re. Application No. PCT/IL2018/050666. (13 Pages).
Official Action dated Sep. 27, 2018 From the US Patent and Trademark Office Re. U.S. Appl. No. 16/008,215. (23 pages).
Afraz et al. "Analytical Sensing of Hydrogen Peroxide on Ag Nanoparticles—Multiwalled Carbon Nanotube-Modified Glassy Carbon Electrode", Journal of Solid State Electrochem, 17:2017-2025, 2013.
Benedet et al "Amperometric Sensing of Hydrogen Peroxide Vapor for Security Screening", Analytical and Bioanalytical Chemistry 395: 371-376, 2009.
Campbell et al. "Hydrogen Peroxide Electroreduction at a Silver-Nanoparticle Array: Investigating Nanoparticle Size and Coverage Effects", Journal of Physican CHemistry C, 113: 9053-9062, 2009.
Chen et al. "Improvement of the Reduction Capacity of Activated Carbon Fiber", Carbon, 41: 1265-1271, 2003.
Dong et al. "Inorganic/Organic Doped Carbon Aerogels as Biosensing Materials for the Detection of Hydrogen Peroxide", Analytical Chemistry, 85:11739-11746, 2013.
Garjonyte et al. "Electrocatalytic Reactions of Hydrogen Peroxide at Carbon Paste Electrodes Modified by Some Metal Hexacyanoferrates", Sensors and Actuators B 46: 236-241, 1998.
Goodman "The Electrochemical Analysis of Bovine Bone Derived Supercapacitors Orgarnic Peroxide Explosives and Conducting Polymer Nanojunctions", Theses—Chemastry Department, 208 Pages, 2013.
Habihi et al. "Voltammetric and Amperometric Determination of Hydrogen Peroxide using a Carbon-Ceramic Electrode Modified With a Nanohybrid Composite Made from Single-Walled Carbon Nanotubes and Silver Nanoparticles", Microchim Acta, 177:185-193, 2012.

Jia et al. "Synthesis of Palladium/Helical Carbon Nanofiber Hybrid Nanostructures and Their Application for Hydrogen Peroxide and Glucose Detection", ACS Applied Materials & Interfaces, 5: 12017-12022, 2013.
Jin et al. "Preparation of Novel Arrays Silver Nanoparticles Modified Polyrutin Coat-Paraffin-Impregnated Graphite Electrode for Tyrosine and Tryptophan's Oxidation", Electroanalysis 20(8): 907-915, 2008.
Kumaravel et al. "A Novel Nanosilver/Nafion Composite Electrode for Electrochemical Sensing of Methyl Parathion and Parathion", Journal of Electroanalytical Chemistry, 638(2): 231-235, Available Online Nov. 6, 2009.
Langley et al. "Manganese Dioxide Graphite Composite Electrodes: Application to the Electroanalysis of Hydrogen Peroxide, Ascorbic Acid and Nitrite", Analytical Sciences 23: 165-170, 2007.
Li et al. "A novel nonenzynlatic hydrogen peroxide sensor based on silver nanopartides and ionic liquid functionalized nlultiwalled carbon nanotube composite modified electrode", Electrochimica Acta, 113: 170-175, 2013.
Li et al. "Nanoporous Carbon Nanofibers Decorated with Platinum Nanoparticles for Non-Enzymatic Electrochemical Sensing of H2O2", Nanomaterials,5:1891-1905, 2015.
Liu et al. "A method for the Production of Reduced Graphene Oxide Using Benzylamine as a Reducing and Stabilizing Agent and its Subsequent Decoration with Ag Nanoparticles for Enzymeless Hydrogen Peroxide Detection",Carbon, 49: 3158-3164, 2011.
Lorestani et al. "One-Step Hydrothermal Green Synthesis of Silver Nanopartide-Carbon Nanotube Reduced-Graphene Oxide Composite and its Application as Hydrogen Peroxide Sensor", Sensors and Actuators B: Chemical, 208: 389-398, 2015.
Lu et al. "Determination of Explosives Based on Novel Type of Sensor Using Porphyrin Functionalized Carbon Nanotubes", Colloids and Surfaces B: Biointerfaces, 88: 396-401, Available Online Jul. 18, 2011.
Lu et al. "Nanomental-Decorated Exfoliated Graphite Nanoplatelet Based Glucose Biosensors with High Sensitivity and Fast Response", ACS Nano, 2(9): 1825-1832, 2008.
Mamo et al. "Development of a Molecularly Imprinted Polymer-Based Sensor for the Electrochemical Determination of Triacetone Triperoxide (TATP)", Sensors, 14(12): 23269-23282, Published Online Dec. 5, 2014.
Mani et al. "Electrodeposition of Copper Nanoparticles Using Pectin Scaffold at Graphene Nanosheets for Electrochemical Sensing of Glucose and hydrogen peroxide", Electrochimica Acta, 176:804-810, 2015.
Mbah et al. "Solid Membrane Electrode Assembly for on Board Detection of Peroxides Based Explosives", Sensors and Actuators B, 222: 693-697, 2016.
Sablok et al. "Amine Functionalized Graphene Oxide/CNT Nanocomposite for Ultrasensitive Electrochemical Detection of Trinitroluene", Journal of Hazardous Materials, 248-249: 322-328, Published Online Jan. 23, 2013.
Salimi et al. "A Novel Non-Enzymatic Hydrogen Peroxide Sensor Based on Single Walled Carbon Nanotubes-Manganese Complex Modified Glassy Carbon Electrode", Electrochinlica Acta 56: 3387-3394, 2011.
Schulte-Ladbeck et al. "Liquid Chromatography—Post-Column Photochemical Conversion and Electrochemical Detection for Determination of Peroxide-Based Explosives", Chromatographia 57: Supplement, S61-S66, 2003.
Shamsipur et al. "A High Sensitive TNT Sensor Based on Electrochemically Reduced Graphene Oxide-Poly(Amidoamine) Modified Electrode", Electroanalysis, 27(6): 1466-1472, Published Online Mar. 18, 2015.
Welch et al. "Silver Nanoparticle Assemblies Supported on Glassy-Carbon Electrodes for the Electro-Analytical Detection of Hydrogen Peroxide", Analytical and Bioanalytical Chemistry, 382(1): 12-21, Published Online Apr. 26, 2005.
Supplementary European Search Report dated Apr. 5, 2019 Form the European Patent Office Re. Application No. 18782866.0. (6 Pages).

(56) References Cited

OTHER PUBLICATIONS

Arul et al. "Silver Nanoparticles Built-In Zinc Metal Organic Framework Modified Electrode for the Selective Non-Enzymatic Determination of H2O2", Electrochimica Acta, XP029970277, 235: 680-689, Available Online Mar. 16, 2017.
De Souza et al. "Nonenzymatic Amperometric Sensors for Hydrogen Peroxide Based on Melanin-Capped Fe3+-, Cu2+-, or Ni2+-Modified Prussian Blue Nanoparticles", IEEE Sensors Journal, XP011662692, 15(9): 4749-4757, Sep. 2015.
Lu et al. "Ag Nanoparticles Self-Supported on Ag2V4O11 Nanobelts: Novel Nanocomposite for Direct Electron Transfer of Hemoglobin and Detection of H2O2", Sensors and Actuators B: Chemical, XP027278889, 150(1): 200-205, Available Online Jul. 16, 2010.
Requisition by the Examiner dated Feb. 15, 2019 From the Innovation, Science and Economic Development Canada, Canadian Intellectual Property Office Re. Application No. 3,020,573. (6 Pages).
Halouzka et al. "Nanostructured Silver and Platinum Modified Carbon Fiber Microelectrodes Coated With Nafion for H2O2 Determination", Journal of Biochemcial Technology, 2(5): S70-S73, Publisched Online Oct. 25, 2011.
Halouzka et al. "Silver-Nafion Coated Cylindrical Carbon Fiber Microelectrode for Amperometric Monitoring of Hydrogen Peroxide Heterogeneous Catalytic Decomposition", Chemical Engineering Journal, 165(3): 813-818, Dec. 15, 2010.
Marwan et al. "Functionalization of Glassy Carbon Electrodes With Metal-Based Species", Chemical Materials, 17(9): 2395-2403, Published on Web Apr. 8, 2005.
Nia et al. "Hydrogen Peroxide Sensor: Uniformly Decorated Silver Nanoparticles on Polypyrrole for Wide Detection Range", Applied Surface Science, 357(Part B): 1565-1572, Dec. 1, 2015.
Ojani et al. "Electrocatalytic Oxidation of Hydrogen Peroxide on Poly(M-Toluidine)-Nickel Modified Carbon Paste Electrode in Alkaline Medium", Electroanalysis, 22(14): 1607-1616, Jul. 2010.
Parajuli "Sensitive Detection of High Explosives Using Electrogenerated Chemiluminescence", Abstract of a Dissertation Submitted to the Graduate School of The University of Southern Mississippi in Partial Fulfillment of the Requirements for the Degree of Doctor of Philisophy, p. 1-126, May 2011.
Requisition dated Feb. 8, 2019 From the Innovation, Science and Economic Development Canada, Canadian Intellectual Property Office Re. Application No. 3,020,655. (7 Pages).
Fu et al. "Amino Functionalized Mesoporous Silica Microspheres With Perpendicularly Aligned Mesopore Channels for Electrochemical Detection of Trace 1,4,6-Trinitrotoluene", Electrochimica Acta, 56(1): 102-107, Available Online Sep. 21, 2010.
Vu et al. "Electrochemical Detection of TNT by Differential Pulse Adsorptive Stripping Voltammetry at Carbon Paste Electrode Modified by 1-Butyl-3-Methylimidazolium Tetrafluoroborate", Bulletin of the Korean Chemical Society, 37(3): 378-385, Published Online Feb. 22, 2016.
Krivitsky et al. "The Direct and Selective Electrochemical Vapour Trace Detection of Organic Peroxide Explosives via Surface Decoration", Analytical Chemistry, 91(8): 5323-5330, Published Online Mar. 20, 2019.
Krivitsky et al. "The Direct and Selective Electrochemical Vapour Trace Detection of Organic Peroxide Explosives via Surface Decoration", Analytical Chemistry, Supplementary Information, p. S1-S8, Published Online Mar. 20, 2019.
Supplementary European Search Report and the European Search Opinion dated Jun. 12, 2019 From the European Patent Office Re. Application No. 18782870.2. (11 Pages).
Agüí et al. "Rapid Voltammetric Determination of Nitroaromatic Explosives at Electrochemically Activated Carbon-Fibre Electrodes", Analytical and Bioanalytical Chemistry, XP019327334, 382(2): 381-387, Published Online Apr. 14, 2005.
Requisition dated Jul. 10, 2019 From the Innovation, Science and Economic Development Canada, Canadian Intellectual Property Office Re. Application No. 3,020,655. (6 Pages).
Delamar et al. "Covalent Modification of Carbon Surfaces by Grafting of Functionalized Aryl Radicals Produced From Electrochemical Reduction of Diazonium Salts", Journal of the American Chemical Society, 114(14): 5883-5884, Jul. 1, 1992.
McCreery "Advanced Carbon Electrode Materials for Molecular Electrochemistry", Chemical Reviews, 108(7): 2646-2687, Published on Web Jun. 17, 2008.
Communication Pursuant to Article 94(3) EPC dated Feb. 3, 2020 From the European Patent Office Re. Application No. 18782870.2. (7 Pages).
Dong et al. "Molecular Recognition and Specific Interactions for Biosensing Applications", Sensors, 8(10): 6605-6641, Published Online Oct. 23, 2008.
International Search Report and the Written Opinion dated Mar. 17, 2020 From the International Searching Authority Re. Application No. PCT/IL2019/051394. (11 Pages).
Huffman et al. "Carbon-Fiber Microelectrodes for In Vivo Applications", Analyst, 1340): 18-24, Published Online Oct. 31, 2008.
Translation dated Oct. 5, 2020 of Notification of Office Action dated Aug. 25, 2020 From the State Intellectual Property Office of the People's Republic of China Re. Application No. 201880002996.6. (15 Pages).

\* cited by examiner

ELECTROCHEMICAL DETECTION OF NITRO-CONTAINING COMPOUNDS

RELATED APPLICATION

This application claims the benefit of priority under 35 USC § 119(e) of U.S. Provisional Patent Application No. 62/519,934 filed on Jun. 15, 2017, the contents of which are incorporated herein by reference in their entirety.

FIELD AND BACKGROUND OF THE INVENTION

The present invention, in some embodiments thereof, relates to detection of chemicals and, more particularly, but not exclusively, to novel electrodes, and to systems and methods employing same, which are usable in electrochemical detection of nitro-containing chemicals such as nitro-containing explosives.

An 'explosive' is a chemically-unstable molecule having a rapid rate of autodecomposition, with the accompanying evolution of large amounts of heat and aseous products. There has been a great increase in the development of trace and ultra-trace explosive detection in the last decade, mainly due to the globalization of terrorist acts, and the reclamation of contaminated land previously used for military purposes.

In addition, the availability of raw materials for the preparation of explosives, together with the growing access to information on preparing these explosives, allows for almost anyone with sufficient will and internet access to prepare a bomb. The vast number of people passing through borders, public places, airports etc. poses a huge challenge for current day security screening technologies. The same challenge applies to homes and buildings security. The ultimate goal is to be able to rapidly and effectively screen every passing person, without the need to delay the traffic of people, and without human contact if possible.

Explosives, especially concealed ones, have a very low vapor pressure or 'signature' in the surrounding air. The effective vapor pressure of explosives can be reduced by a factor of up to 1000, with the use of plastic packages. Detection methods for traces of explosives therefore continue to be plagued by the low volatility of many target analytes.

One of the most commonly-used high explosives over the last 100 years is 2,4,6-trinitrotoluene (TNT), which poses not only a direct security threat, but also great environmental concern due to soil and water contamination near production, storage and test sites.

Analytical procedures in use today for the trace detection of explosives typically involve collecting vapor samples and analyzing them with a sensitive method. Several methodologies have been reported for detecting TNT and other explosives. These are based on electrochemistry, ion-mobility spectrometry, gas chromatography, high-performance liquid chromatography, surface enhanced Raman spectroscopy, nuclear quadruple resonance' and neutron activation analysis photoluminescence, surface acoustic-wave devices, microcantilevers, fluorescent polymers, surface plasmon resonance, quartz crystal microbalance, immunosensors and other methods. These methods are reliable for explosives detection, but involve time-consuming procedures, high costs and operation by well qualified staff, which limits their application in field conditions.

Additional methods involve trained animals including dogs, mice and bees and utilize their highly sensitive sense of smell for traces explosive detection. These methods however require intense and expensive training of the animal, and handling by an expert.

Electrochemical detection methods utilize electrodes, immersed in an electrolyte, and connected to a potentiometer, which measures the current that flows between the electrodes upon potential application. Typically, during an electrochemical reaction the electrode potential is varied; and an electric current flows between the electrodes that is characteristic of the presence of an electrochemically reactive substance in the electrolyte. Electrochemical detection methods and devices are typically highly sensitive, relatively simple, hand held, low cost and reliable.

The utilization of electrochemical based sensors for the detection of nitro-containing compounds is straightforward: the nitro groups are highly electrochemically-reactive and can be easily reduced to amines by applying typical negative potentials [Bratin et al. *Analytica Chimica Acta* 130, 295-311, (1981)]. Numerous strategies have therefore been suggested for designing a working electrode for the detection of nitro-based explosives. Currently reported designs are variable and include, for example, noble metals and their alloys, carbon electrodes chemically modified with ferrocene or quinone derivatives, glassy carbon modified with mesoporous ordered carbon, hemin analogues (phtalocianines and porphirynes), glassy carbon modified with a conducting polymer (porphyrin-thiol), carbon/$TiO_2$ composite electrode, carbon/Sn core-shell electrode, glassy carbon modified with porphyrin/graphene mix, graphene-modified glassy carbon electrode, Two-dimensional molecular imprinting alkane-thiols modified gold nano-particles and screen-printed electrode.

However, the required adsorptive voltammetry, rotating disk electrode, long accumulation, stripping voltammetry, low stability surface modification, pre-concentration and deaeration often complicate the protocol of detection and limit the practical application of these designs in detecting nitro-containing explosives.

An efficient design of an electrode for electrochemical detection of nitro-containing compounds should perform high stability, fast kinetics of the reduction reaction, high sensitivity, and a short measurement time.

One of the most pronounced limitations in electrochemical measurement under atmospheric conditions is the presence of dissolved oxygen in a sample. The dissolved oxygen concentration in aqueous electrochemical solution is about 0.25 mM (about 8 ppm) [Julia, P. L. C. & Coso, E. B. *Homenatge professor Josep M. Costa (eBooK) 2a part. Trends in electrochemistry and corrosion at the beginning of the 21st century*. (Publicacions i Edicions de la Universitat de Barcelona, 2004)] and is much higher in non-aqueous electrochemical solutions [Achord, J. M. & Hussey, *Analytical Chemistry* 52, 601-602, (1980)]. Therefore the dissolved oxygen concentration is higher by several orders of magnitudes than that of the nitro explosive analyte. As a result, the current of dissolved oxygen reduction is sufficiently intense to cause a partial masking of nitro aromatics and complete masking of nitro-amines peaks [Bratin et al., 1981, supra].

This limitation is typically treated by deaeration; the oxygen is removed by means of bubbling inert gas, for example argon or nitrogen. Typically, 10-15 minutes of deaeration are required in order to obtain efficient oxygen removal in a sample of approximately 5 ml. This lengthy procedure is not in line with the requirements for real time detection of nitro-containing explosives [W. Chen, Y. Wang, C. Bruckner, C. M. Li, Y. Lei, *Sensor Actuat B-Chem* 2010, 147. 191-197].

WO 2011/154939 and WO 2014/111944 describe nanodevices which utilize functionalized nanowires for detecting nitro-containing compounds. The nanowires feature a functional moiety that interacts with a nitro-containing compound by forming a charge-transfer complex therewith.

WO 2005/050157, WO 2006/090401, and WO 2007/029245 teach systems for detecting traces of nitro-aromatic compounds in air, which utilize carbon electrodes modified by amino-aromatic compound or nitrogen-containing heterocyclic compounds.

Additional background art includes Chaubey, A. & Malhotra, B. D. Mediated biosensors. *Biosens Bioelectron* 17, 441-456, (2002); Zang et al. *Analytica Chimica Acta* 683, 187-191, (2011); U.S. Pat. No. 6,872,786; Chen et al. *Sensor Actuat B-Chem* 147, 191-197, (2010); Filanovsky, B. et al. *Adv Funct Mater* 17, 1487-1492, (2007); Grigoriants, I. et al. *Electrochim Acta* 54, 690-697, (2008); Guo et al. *Electroanal* 23, 885-893, (2011); Chen et al. *Chemistry—An Asian Journal* 6, 1210-1216, (2011); Wang et al. *Sensors-Basel* 11, 7763-7772, (2011); Cizek, K. et al. *Analytica Chimica Acta* 661, 117-121, (2010); Galik et al. *Electroanal* 23, 1193-1204, doi:DOI 10.1002/elan.201000754 (2011); WO 2010/112546; WO 2010/227382; WO 2015/059704; WO 2017/098518; Engel, Y. et al. *Angew Chem Int Edit* 49, 6830-6835, (2010); Dwivedy et al. *Journal of Chromatography A* 29, 120-125 (1967); and Lichtenstein, A. et al. *Nat Commun* 5, (2014).

SUMMARY OF THE INVENTION

The present inventors have now designed and successfully practiced a novel sensing system for electrochemical detection of nitro-containing compounds. The designed system can detect variable nitro-containing compounds, can distinguish between structurally-different nitro-containing compounds (e.g., nitro-aromatic, nitrate-ester and nitro-amine compounds) in a single cycle, and can perform electrochemical detection efficiently in the presence of dissolved oxygen, thus circumventing the need to remove oxygen prior to the detection operation. The sensing system can be operated such that a detectable concentration of a nitro-containing compound is lower than 20 ppb and even lower, and at a detection time of less than 20 seconds, and is therefore highly useful in field conditions.

The sensing system disclosed herein is based on a carbon electrode, preferably a carbon fiber electrode, more preferably, a carbon fiber microelectrode, which is modified at its surface. The electrode is modified by subjecting its surface to oxygen plasma and/or by covalently attaching thereto a functional moiety that forms a charge-transfer complex with a nitro-containing compound.

The sensing system and methods disclosed herein meet the requirements of a sensitive and robust methodology for detection of explosives by being highly sensitive, selective (sophisticated) and working in real time regime, while at the same time, it features a high sampling rate and multiplex capabilities, while maintaining handling simplicity and reliability. The sensing system disclosed herein can be designed as hand-held devices, with minimized and miniaturized dimensions, weight and costs.

According to an aspect of some embodiments of the present invention there is provided a sensing electrode comprising a carbon electrode and a functional moiety covalently attached to a surface of the electrode, the functional moiety being such that forms a charge-transfer complex with a nitro-containing compound.

According to some of any of the embodiments described herein, the carbon electrode is a carbon fiber electrode.

According to some of any of the embodiments described herein, the electrode is a carbon fiber microelectrode.

According to some of any of the embodiments described herein, the electrode is a carbon paper microelectrode.

According to some of any of the embodiments described herein, the electrode is a gas permeable electrode.

According to some of any of the embodiments described herein, the carbon electrode is a surface-modified electrode featuring a plurality of surface reactive groups.

According to some of any of the embodiments described herein, the carbon electrode is a surface-modified electrode featuring a plurality of surface reactive groups and the functional moiety or a plurality of functional moieties is/are attached to at least a portion of these surface reactive groups.

According to some of any of the embodiments described herein, the surface reactive groups comprise hydroxy groups.

According to some of any of the embodiments described herein, a length of the functional moiety is smaller than 2 nm, or smaller than 1.5 nm, or smaller than 1 nm. According to some of any of the embodiments described herein, the functional moiety comprises an electron donating moiety.

According to some of any of the embodiments described herein, the electron donating moiety is selected from the group consisting of $C_{1-10}$ alkyl substituted by an electron donating group, a $C_{1-10}$ alkenyl substituted by an electron donating group, an aryl substituted by an electron donating group, a cycloalkyl substituted by an electron donating group, a heteroalicyclic comprising a heteroatom that functions as an electron donating group and a heteroaryl comprising a heteroatom that functions as an electron donating group.

According to some of any of the embodiments described herein, the electron donating moiety a $C_{1-10}$ alkyl substituted by an electron donating group According to some of any of the embodiments described herein, the electron donating group is selected from the group consisting of amine, alkoxy, thioalkoxy, aryloxy and thioaryloxy.

According to some of any of the embodiments described herein, the electron donating group is amine.

According to some of any of the embodiments described herein, the functional moiety comprises a silicon atom.

According to some of any of the embodiments described herein, the functional group comprises a silyl or siloxane substituted by the electron donating moiety.

According to some of any of the embodiments described herein, the silyl or siloxane is further substituted by at least one hydrocarbon group.

According to some of any of the embodiments described herein, the functional moiety comprises a silyl substituted by an aminoalkyl, the alkyl being 1-10 carbon atoms in length.

According to some of any of the embodiments described herein, the alkyl is 1-5 carbon atoms in length.

According to some of any of the embodiments described herein, the functional moiety is selected from the group consisting a silyl substituted by an aminopropyl and a siloxane substituted by an aminopropyl.

According to some of any of the embodiments described herein, the silyl is further substituted by 2 alkyl groups.

According to some of any of the embodiments described herein, the functional moiety is covalently attached to the carbon electrode via a —Si—O— bond.

According to some of any of the embodiments described herein, the electrode is usable for determining a presence and/or level of a nitro-containing compound in a sample, upon integrating the electrode in an electrochemical cell which further comprises an electrolyte.

According to an aspect of some embodiments of the present invention there is provided a sensing system (sensor) comprising a sensing electrode according to any of the respective embodiments and any combination thereof, the sensing electrode being connectable to a power source.

According to some of any of the embodiments described herein, the sensing electrode forms a part of an electrochemical cell.

According to some of any of the embodiments described herein, the electrochemical cell further comprises a reference electrode.

According to some of any of the embodiments described herein, the electrochemical cell further comprises an auxiliary electrode.

According to some of any of the embodiments described herein, the system further comprises an inlet port for contacting an electrolyte solution with the sensing electrode.

According to some of any of the embodiments described herein, the system further comprises means for introducing an electrolyte solution to the electrochemical cell.

According to some of any of the embodiments described herein, the system further comprises an electrolyte solution in contact the sensing electrode.

According to some of any of the embodiments described herein, the electrolyte features a pH lower than 7, as described herein in any of the respective embodiments.

According to some of any of the embodiments described herein, the electrolyte features an acidic pH.

According to some of any of the embodiments described herein, the electrolyte comprises a mixture of an aqueous solvent and an organic solvent.

According to some of any of the embodiments described herein, the electrolyte comprises a quaternary ammonium salt.

According to some of any of the embodiments described herein, the system further comprises a sample inlet or any other means for contacting the sample with the sensing electrode.

According to some of any of the embodiments described herein, the simple further comprises a sample inlet or any other means for introducing a sample to the electrochemical cell.

According to some of any of the embodiments described herein, the system further comprises a gas outlet.

According to some of any of the embodiments described herein, the system is devoid of means for deaerating the system prior to contacting the system with a sample. According to some of any of the embodiments described herein, the system further comprises a power source electrically connected to the sensing electrode.

According to some of any of the embodiments described herein, the system further comprises a device for measuring an electrochemical parameter of the sensing electrode.

According to some of any of the embodiments described herein, the system further comprises an electrical current measuring device for measuring an electrical current or a change in an electrical current generated at the sensing electrode.

According to some of any of the embodiments described herein, the power source is configured to apply a varying potential to the sensing electrode.

According to some of any of the embodiments described herein, the system further comprises a device for determining a change in the electrical current in response to the varying potential.

According to some of any of the embodiments described herein, the electrochemical cell is configured such that upon contacting a sample containing a nitro-containing compound with the sensing electrode, a presence and/or level of an electrochemical parameter generated in response to applying potential to the sensing electrode is indicative of a presence and/or level of the nitro-containing compound.

According to some of any of the embodiments described herein, the system is configured for determining a change in the electrical current in response to a varying potential applied to the sensing electrode, the change being indicative of a presence and/or level of the nitro-containing compound.

According to some of any of the embodiments described herein, the system further comprises a data processor configured for constructing a fingerprint of the nitro-containing compound, the fingerprint being a change of the electrical current in response to a varying potential (a voltammogram).

According to some of any of the embodiments described herein, the data processor is further configured to access a database of nitro-containing compound fingerprints, to search the database for a database fingerprint matching a constructed fingerprint of the nitro-containing compound, and to identify the nitro-containing compound based on the matched database fingerprint.

According to some of any of the embodiments described herein, the data processor is further configured to determine a level of the identified nitro-containing compound in a sample, the determining being using at least one of (i) a calibration curve stored on a computer readable medium, (ii) a lookup table stored on a computer readable medium, and (iii) a predetermined relationship between the derivative and the level.

According to some of any of the embodiments described herein, the predetermined relationship comprises a linear relationship.

According to an aspect of some embodiments of the present invention there is provided a method of detecting a nitro-containing compound in a sample, the method comprising:

contacting the sample with a sensing electrode according to any of the respective embodiments and any combination thereof;

applying potential to the sensing electrode; and measuring an electrochemical parameter of the sensing electrode, wherein a presence and/or level of the parameter is indicative of a presence and/or level of the nitro-containing compound in the sample.

According to some of any of the embodiments described herein, contacting the sensing electrode with the sample comprises introducing the sample to a sensing system according to any of the respective embodiments as described herein.

According to some of any of the embodiments described herein, the electrochemical parameter comprises an electrical current generated at the sensing electrode, wherein a presence and/or level of the electrical current is indicative of a presence and/or level of the nitro-containing compound.

According to some of any of the embodiments described herein, the method is devoid of deaerating the system.

According to some of any of the embodiments described herein, the sample is a fluid sample.

According to some of any of the embodiments described herein, the sample is a gaseous sample.

According to some of any of the embodiments described herein, the sample comprises oxygen.

According to some of any of the embodiments described herein, contacting the sample with the sensing electrode comprises contacting an electrolyte solution comprising the sample with the sensing electrode.

According to some of any of the embodiments described herein, a concentration of dissolved oxygen in the electrolyte is at least 1 ppm.

According to some of any of the embodiments described herein, a detectable concentration of the nitro-containing compound in the sample is lower than 100 ppb, or lower than 50 ppb.

According to some of any of the embodiments described herein, the nitro-containing compound is a nitro-containing explosive.

According to some of any of the embodiments described herein, the explosive is selected from the group consisting of 2-nitrotoluene; 3-nitrotoluene; 4-nitrotoluene; 2,4,6-trinitrotoluene (TNT); 2,4-dinitrotoluene; 3,4-dinitrotoluene; 2,6-dinitrotoluene; ethylene glycol dinitrate (EGDN); nitroglycerine (NG); cyclotrimethylenetrinitramine (cyclonite; RDX); pentaerythritol tetranitrate (PETN); homocyclonite (octogen; HMX); ammonium nitrate; 1,2,3-propanetrial trinitrate formulation; and any mixture thereof.

According to some of any of the embodiments described herein, the sample comprises at least two nitro-containing compounds, and wherein the determining is of a presence and/or level of each of the compounds.

According to some of any of the embodiments described herein, the nitro-containing compound is in a fluid state.

According to some of any of the embodiments described herein, the nitro-containing compound is in a gaseous state.

According to some of any of the embodiments described herein, a detectable concentration of the nitro-containing compound in the sample is lower than 100 ppb or lower than 50 ppb.

According to an aspect of some embodiments of the present invention there is provided a process of preparing the electrode according to any of the present embodiments, the process comprising: coupling to a carbon electrode featuring a plurality of a first reactive group on at least a portion of its surface of a carbon electrode a compound featuring the functional moiety and a second reactive group that forms a covalent bond with the first reactive groups, thereby preparing the electrode.

According to some of any of the embodiments described herein, the process further comprises, prior to the coupling, generating the first reactive groups on the at least a portion of the surface of the carbon electrode.

According to some of any of the embodiments described herein, generating the reactive groups comprises subjecting the carbon electrode to oxygen plasma treatment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 presents a schematic illustration of an exemplary electrochemical system for detecting nitro-containing compounds according to some embodiments of the present invention.

Figure 2A:
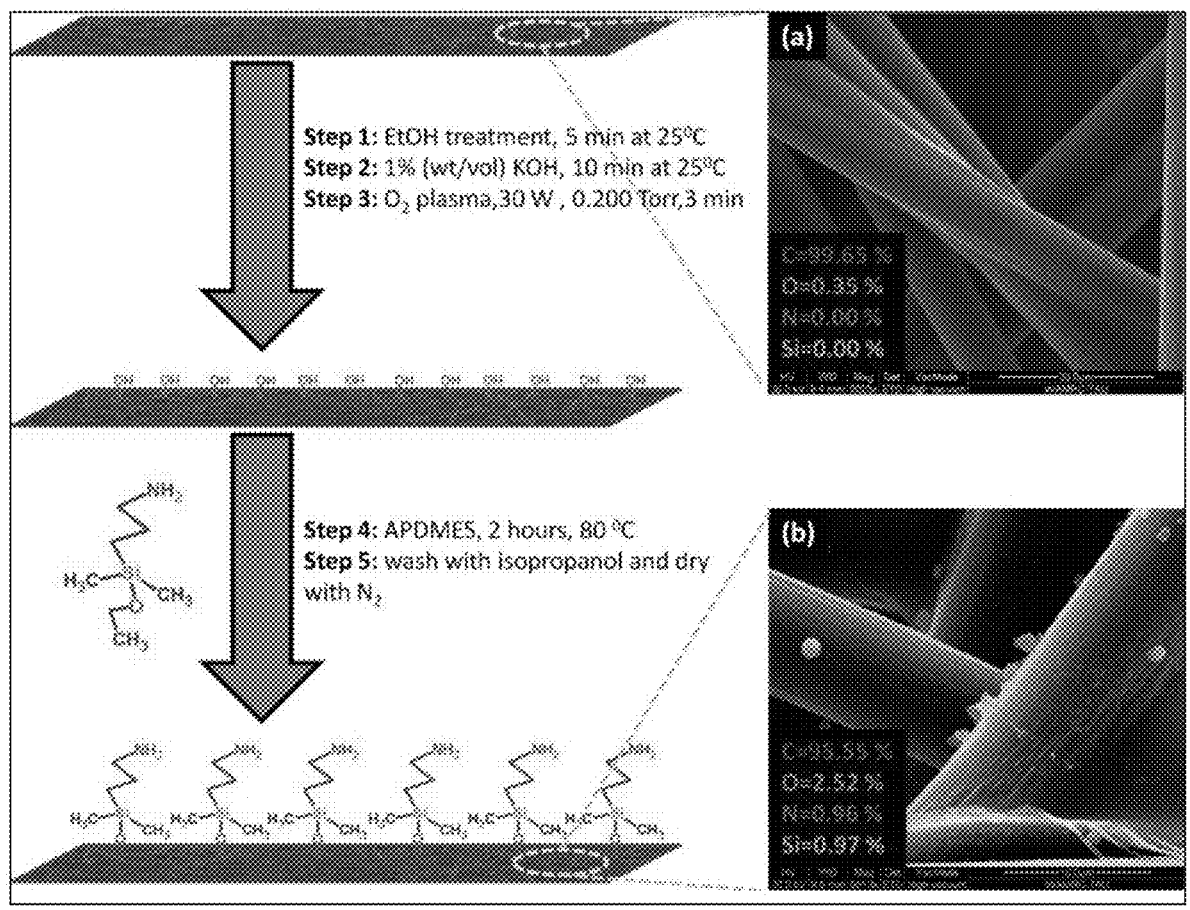
Figure 2B:
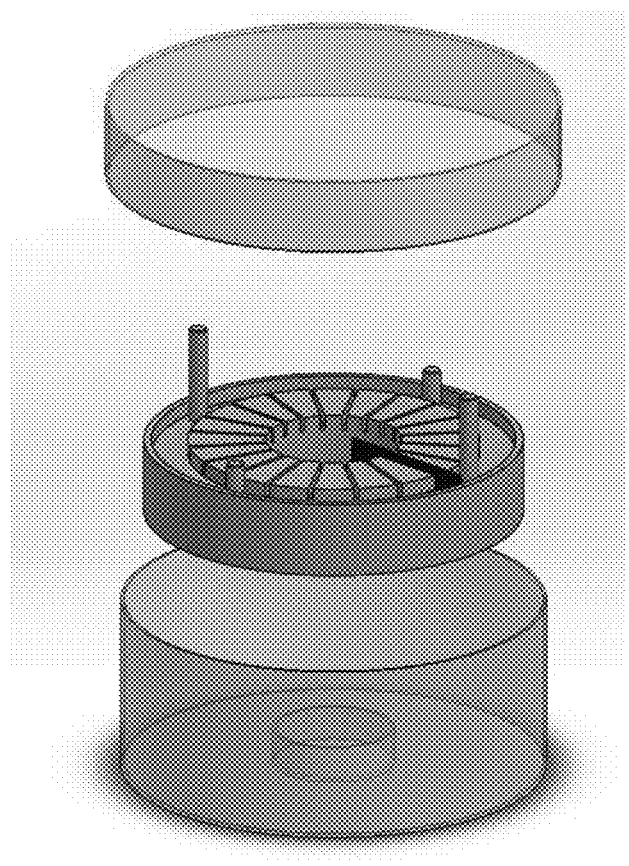

FIGS. 2A-B present a schematic representation of the chemical modification of carbon fiber (CF) microelectrode, according to some embodiments of the present invention (FIG. 2A, left schematic illustrations); and a scanning electron microscope (secondary electrons) image and X-ray photoelectron spectroscopy atomic concentrations for carbon (C), oxygen (O) nitrogen (N) and silicon (Si) analysis before (FIG. 2A, right upper images) and after (FIG. 2B, right lower images) the modification [Abbreviations: Ethanol (EtOH), 3-aminopropyldimethylethoxysilane (APDMES), Potassium hydroxide (KOH)], and a schematic illustration of a device usable in gas phase chemical modification of carbon fiber (CF) microelectrode, according to some embodiments of the present invention (FIG. 2B).

Figure 3A:
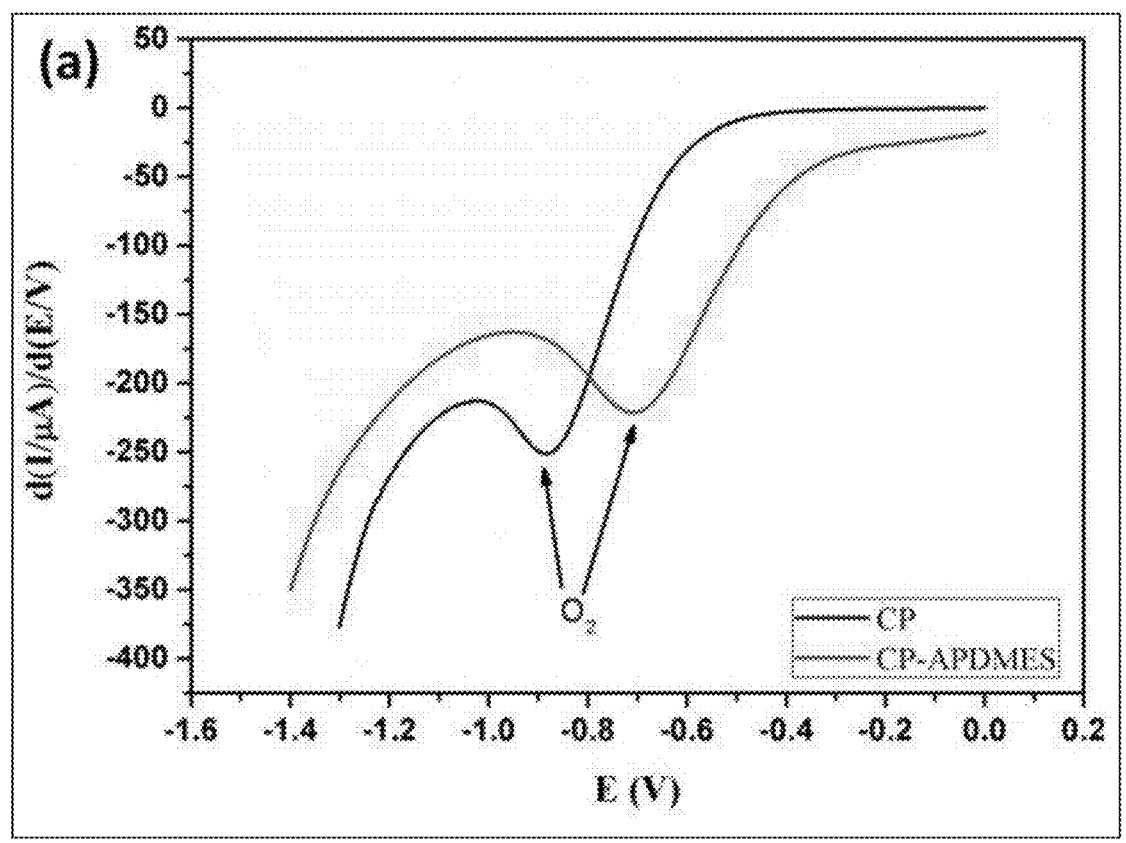

FIG. 3A presents comparative differential pulse voltammetry curves of non-modified CF microelectrode (CP; black line) and of an exemplary amino-modified CF microelectrode (CP-APDMES; red line), according to some embodiments of the present invention. The background solution contained 0.25 M Potassium chloride, 5 mM Tetrabutylammoniumiodide in aqueous buffer phthalate pH 4.0/acetonitrile mix at 7/3 volume ratio, respectively. The differential pulse voltammetry was performed at modulation time of 0.05 seconds, interval time of 0.1 seconds, and modulation amplitude of 50 mV.

Figure 3B:
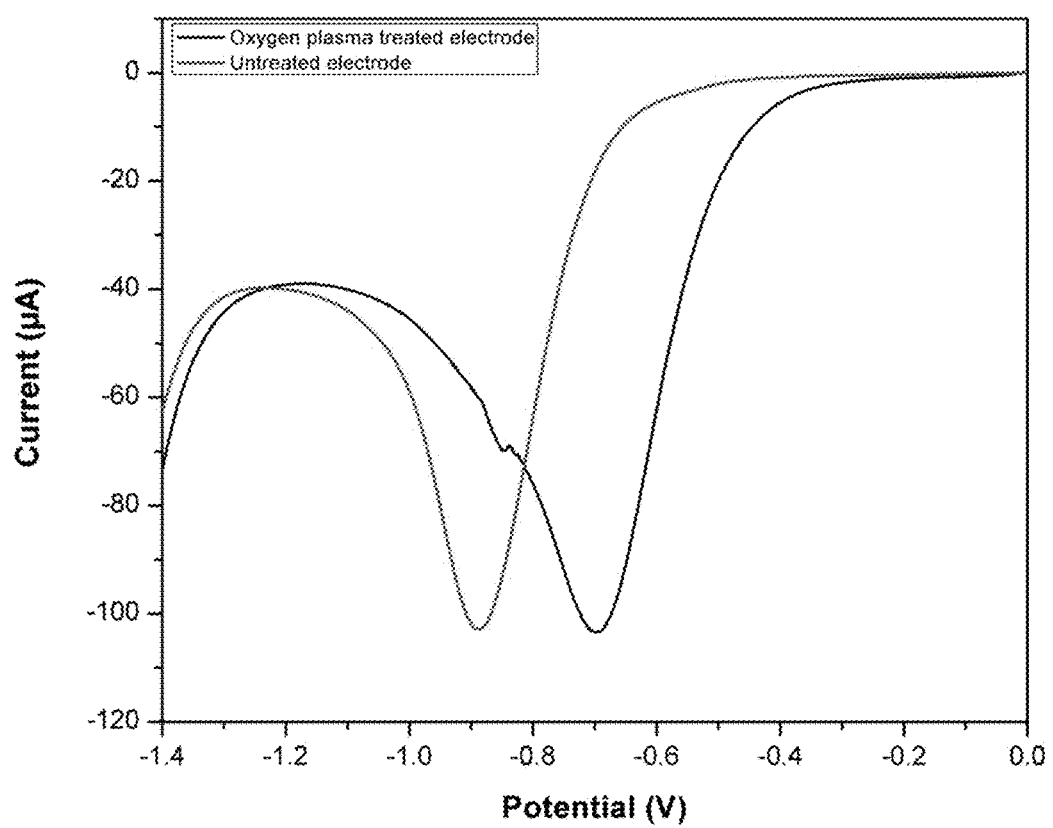

FIG. 3B presents comparative differential pulse voltammetry curves of non-modified CF microelectrode (untreated electrode; red line); and of a CF microelectrode subjected to oxygen plasma treatment (ocygen plasma treated elecrode; black line), according to some embodiments of the present invention. The background solution contained 0.25 M Potassium chloride, 5 mM Tetrabutylammoniumiodide in aqueous buffer phthalate pH 4.0/acetonitrile mix at 7/3 volume ratio, respectively. The differential pulse voltammetry was performed at modulation time of 0.05 seconds, interval time of 0.1 seconds, and modulation amplitude of 50 mV.

Figure 4A:
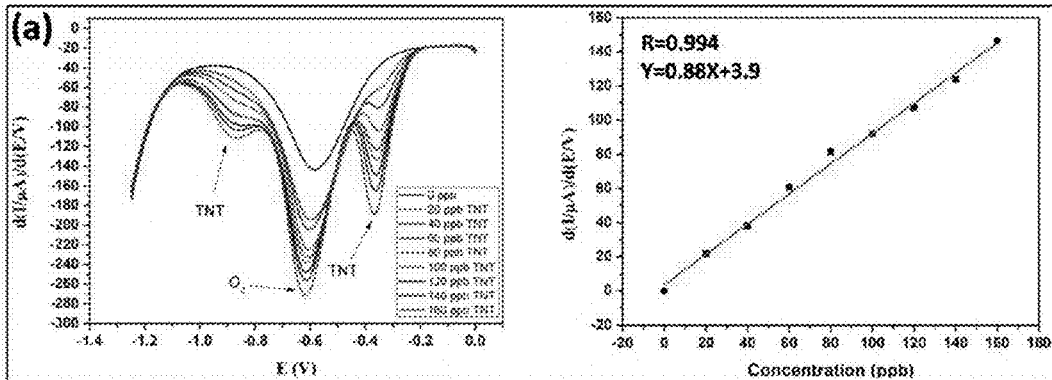
Figure 4B:
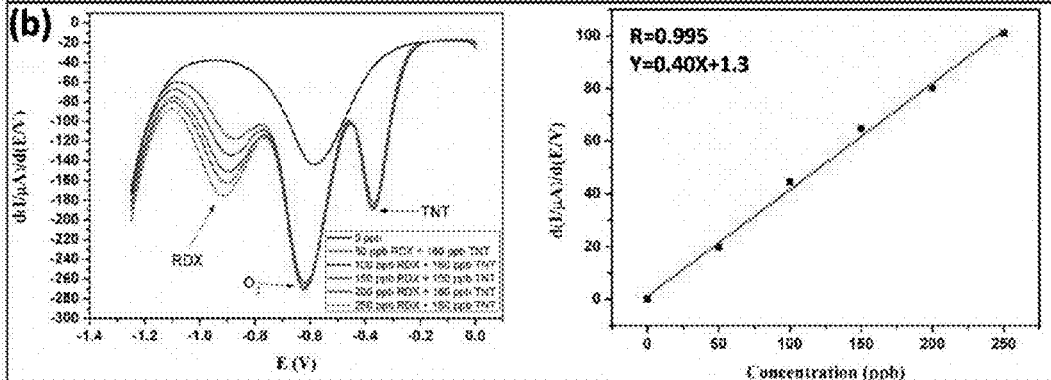
Figure 4C:
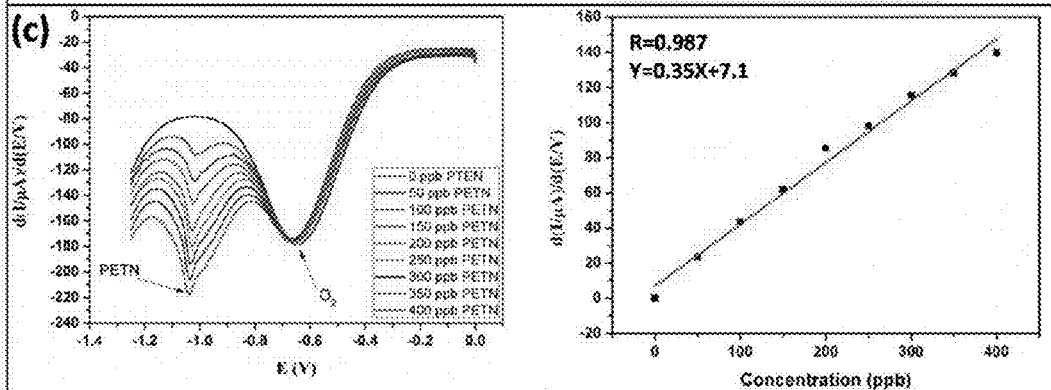

FIGS. 4A-C present differential pulse voltammetry fingerprints (left) and calibration curves (right) as obtained using amino-modified CF microlectrode, for 0-160 ppb of 2-Methyl-1,3,5-trinitrobenzene (TNT), at 20 ppb intervals (FIG. 4A); for 0-250 ppb, at 50 ppb intervals, of 1,3,5-trinitroperhydro-1,3,5-triazine (RDX) in the presence of 160 ppb TNT (FIG. 4B), and for 0-400 ppb [3-nitrooxy-2,2-bis (nitrooxymethyl)propyl] nitrate (PETN), at 50 ppb intervals (FIG. 4C). The differential pulse voltammetry was performed at modulation time of 0.05 seconds, interval time of 0.1 seconds, and modulation amplitude of 50 mV. The background solution contained 0.25 M Potassium chloride, 5 mM Tetrabutylammoniumiodide in aqueous buffer phthalate pH 4.0/acetonitrile mix at 7/3 volume ratio, respectively.

Figure 5A:
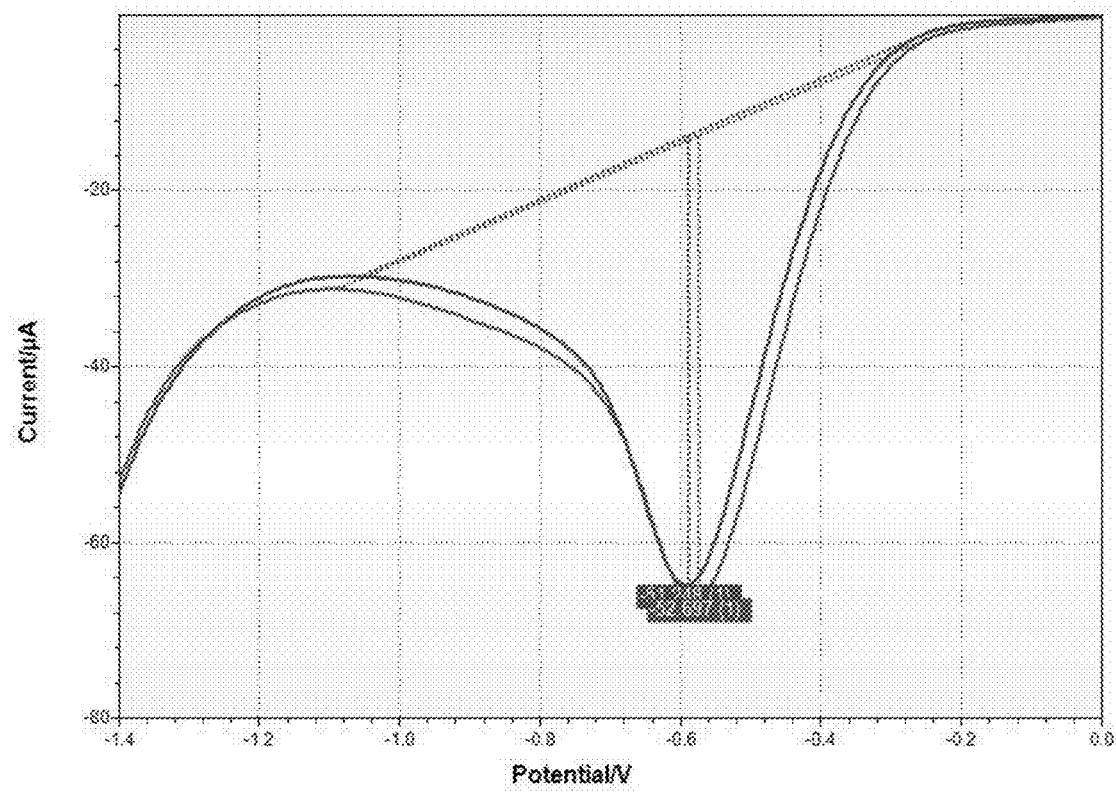
Figure 5B:
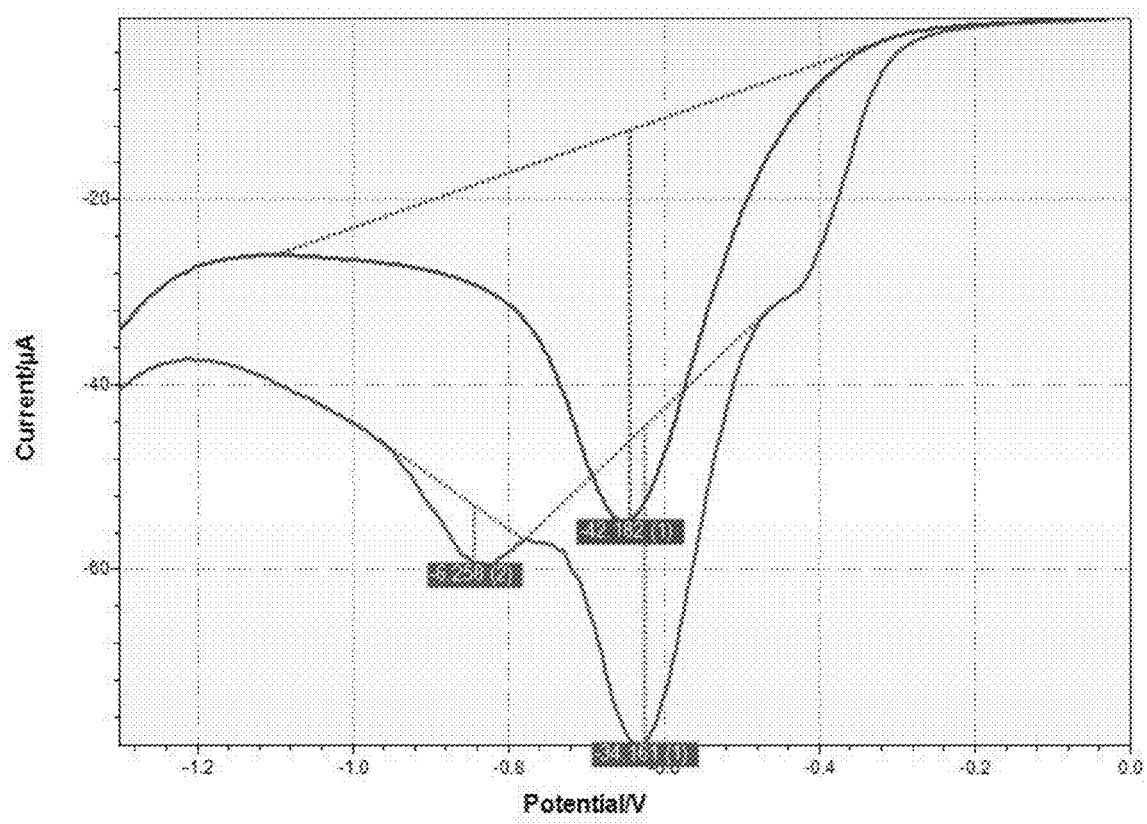
Figure 5C:
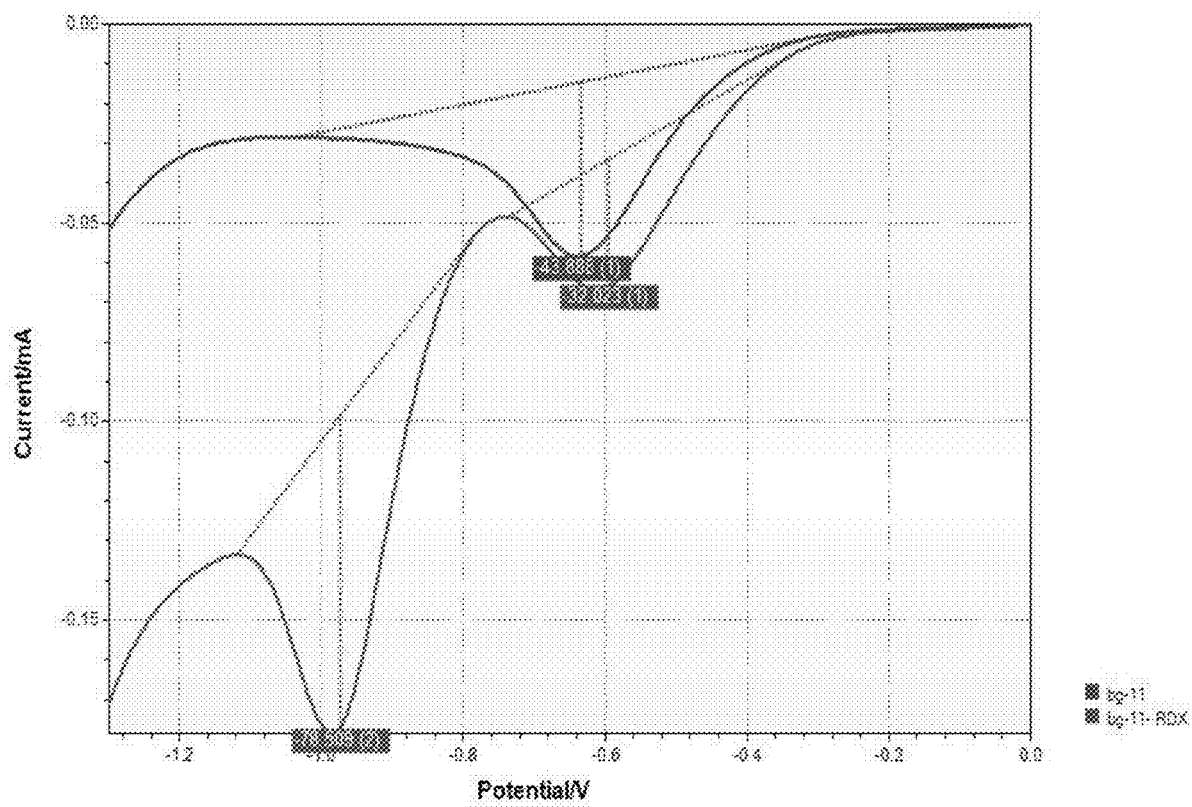
Figure 5D:
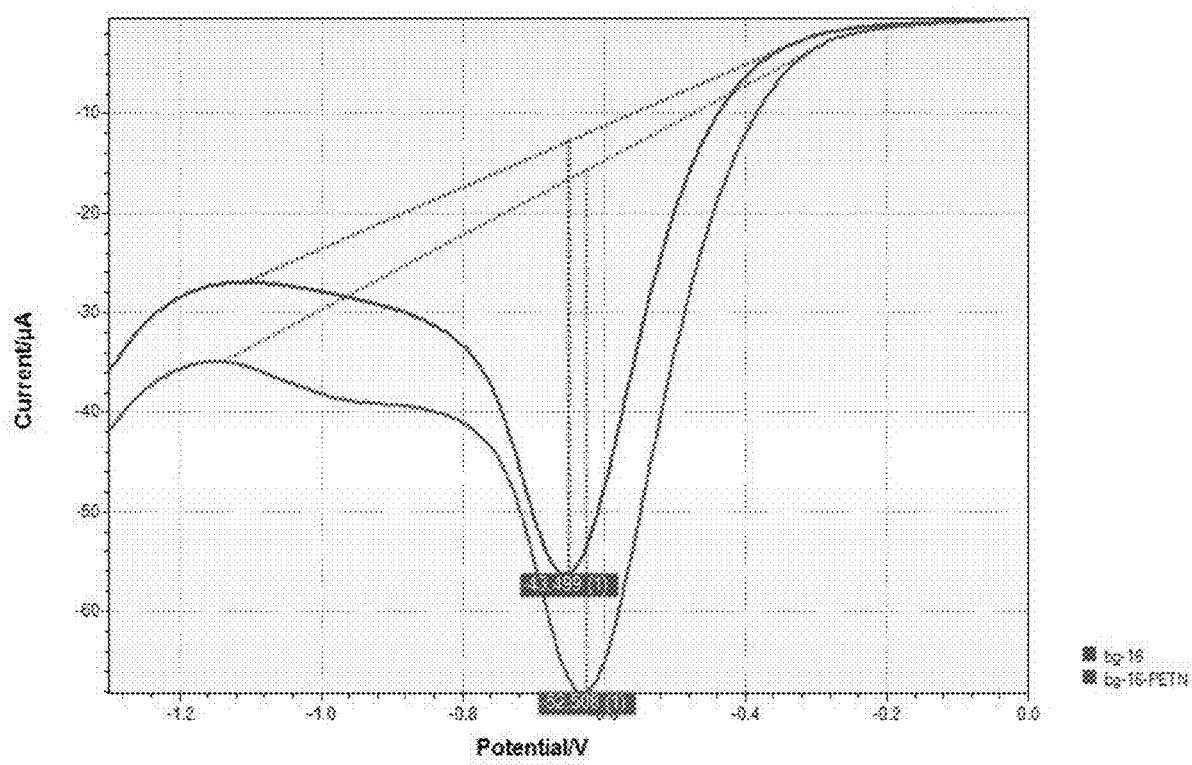
Figure 5E:
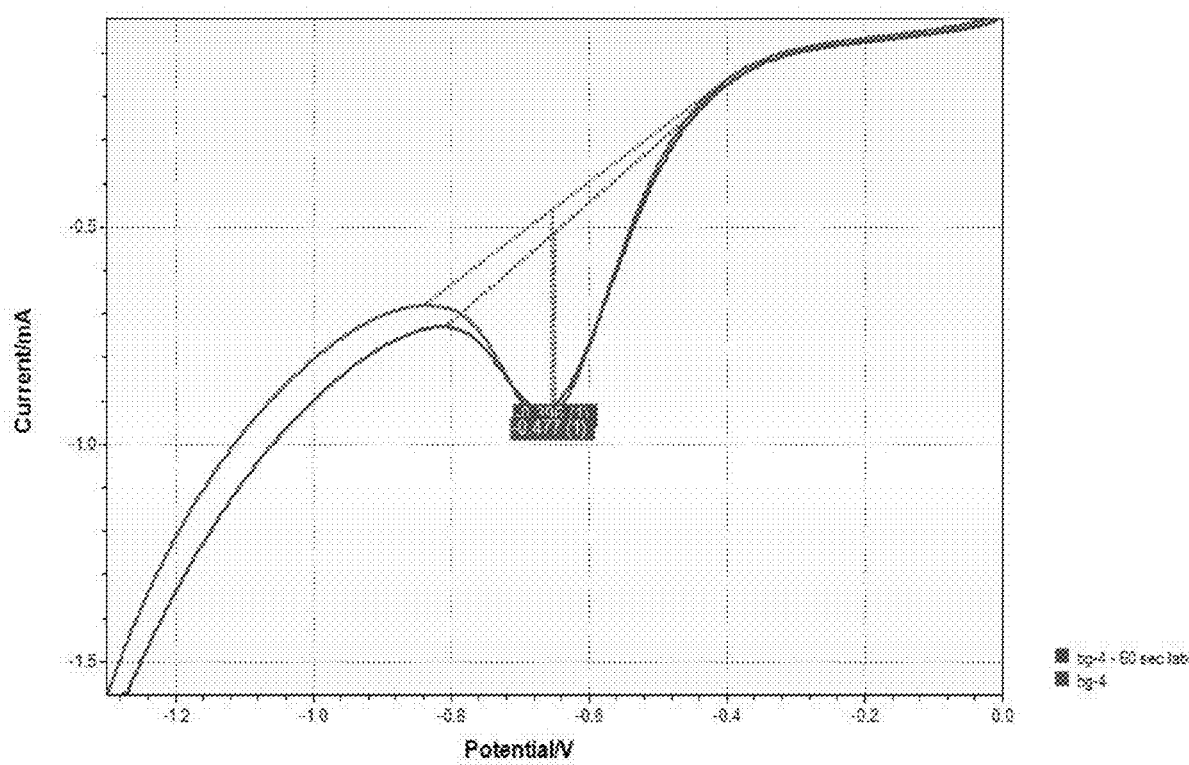
Figure 5F:
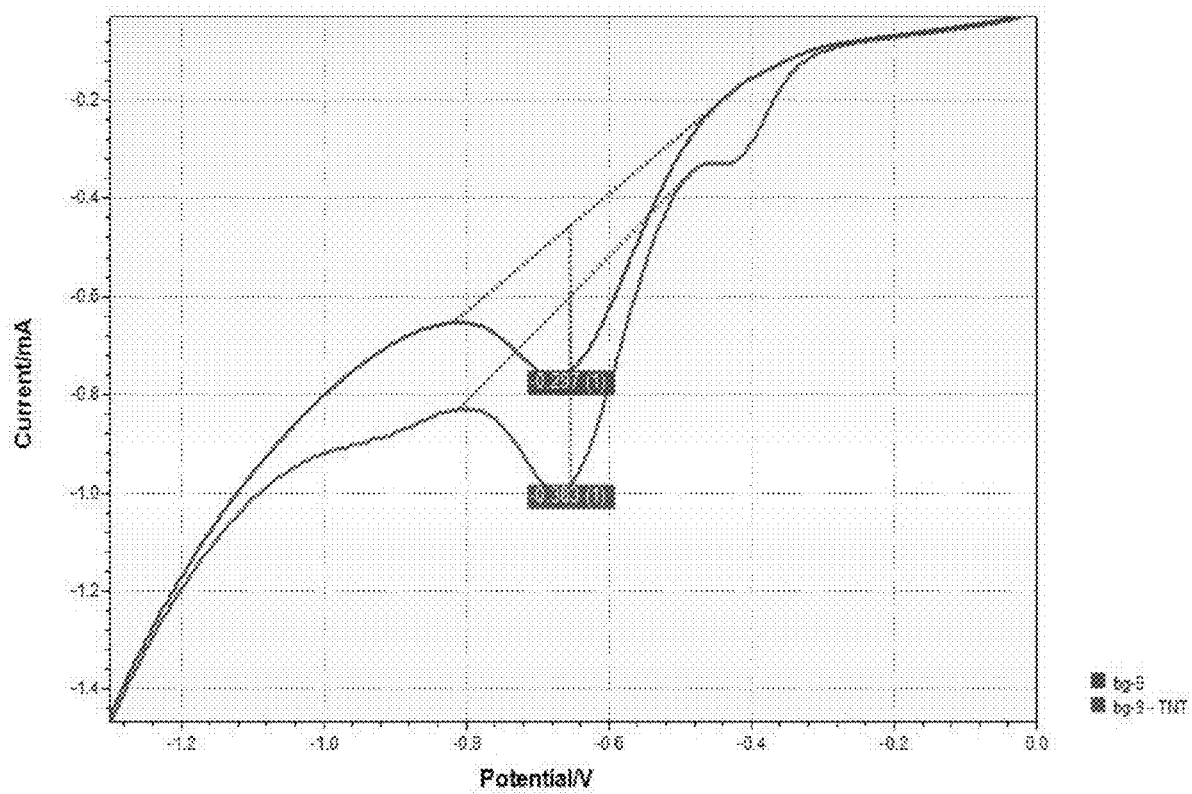
Figure 5G:
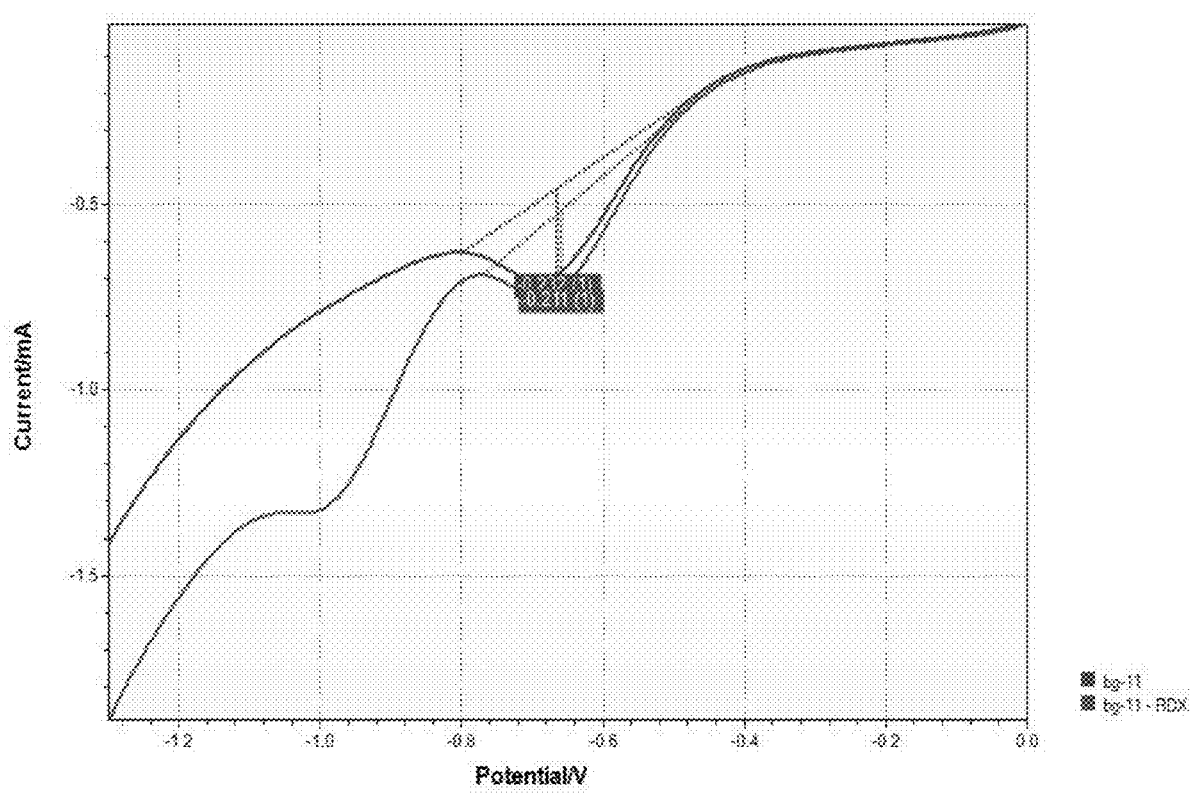

FIGS. 5A-G present linear sweep voltammetry measurements obtained using amino-modified CF microlectrode and an electrolyte solution comprising phosphate buffer, 50 mM, pH 6.5 as the aqueous solution, acetonitrile (3/7 ratio to the phosphate buffer), 5 mM of tetrabutylammonium perchlorate and 250 mM potassium chloride, upon introduction of air during 60 seconds (FIG. 5A), introduction of TNT vapors during 15 seconds (FIG. 5B), and introduction of RDX vapors during 15 seconds (FIG. 5C), and introduction of PETN vapors during 15 seconds (FIG. 5D), and measurements obtained using plasma-treated carbon paper microelectrode and the same electrolyte, upon introduction of air during 60 seconds (FIG. 5E), introduction of TNT vapors during 15 seconds (FIG. 5F), and introduction of RDX vapors during 15 seconds (FIG. 5G).

Figure 6:
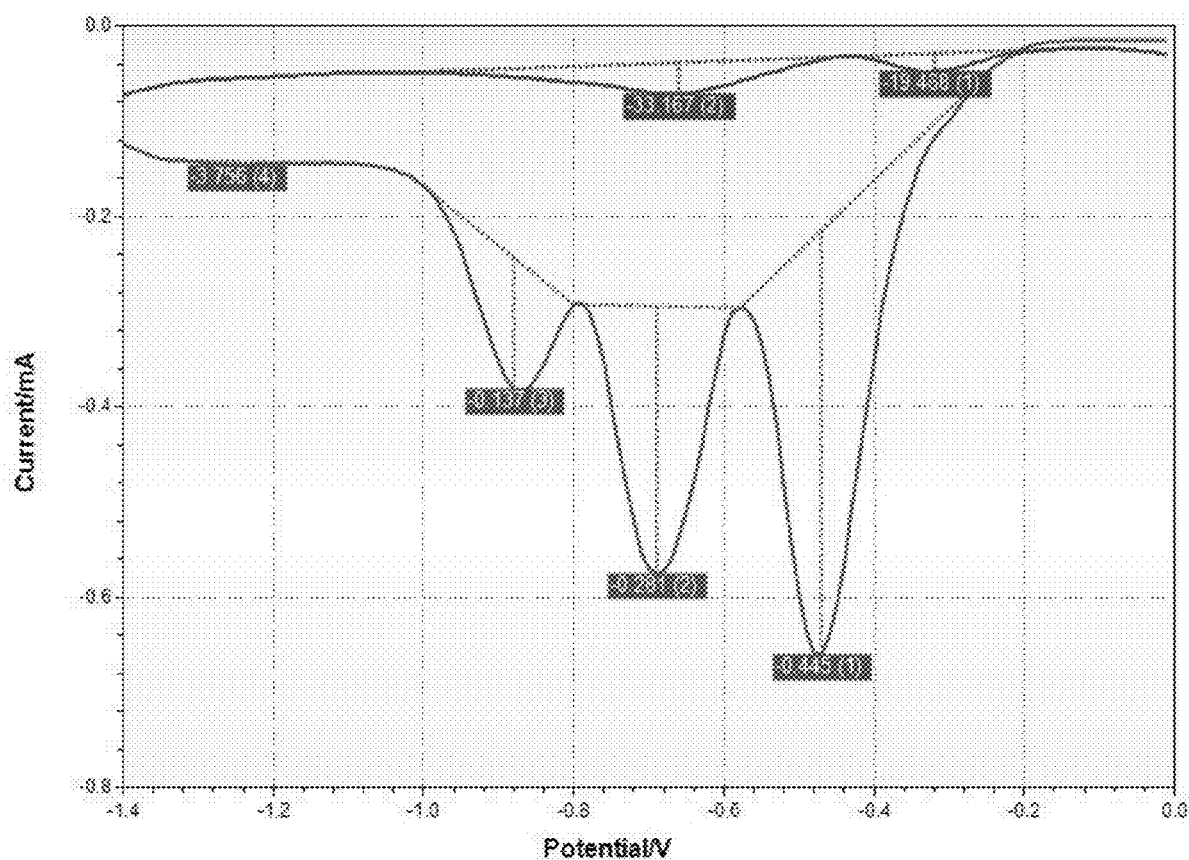

FIG. 6 presents the data obtained in linear sweep voltammetry experiments conducted with the APDMES-modified carbon paper microelectrode, and an electrolyte solution comprising a dibasic phosphate buffer, 100 mM, pH 8.8 as the aqueous solution, acetonitrile (3/7 ratio to the phosphate buffer), 5 mM of tetrabutylammonium perchlorate and 250 mM potassium chloride, upon introduction TNT vapors, after the first scan (red) and after 5 scans (blue).

Figure 7A:
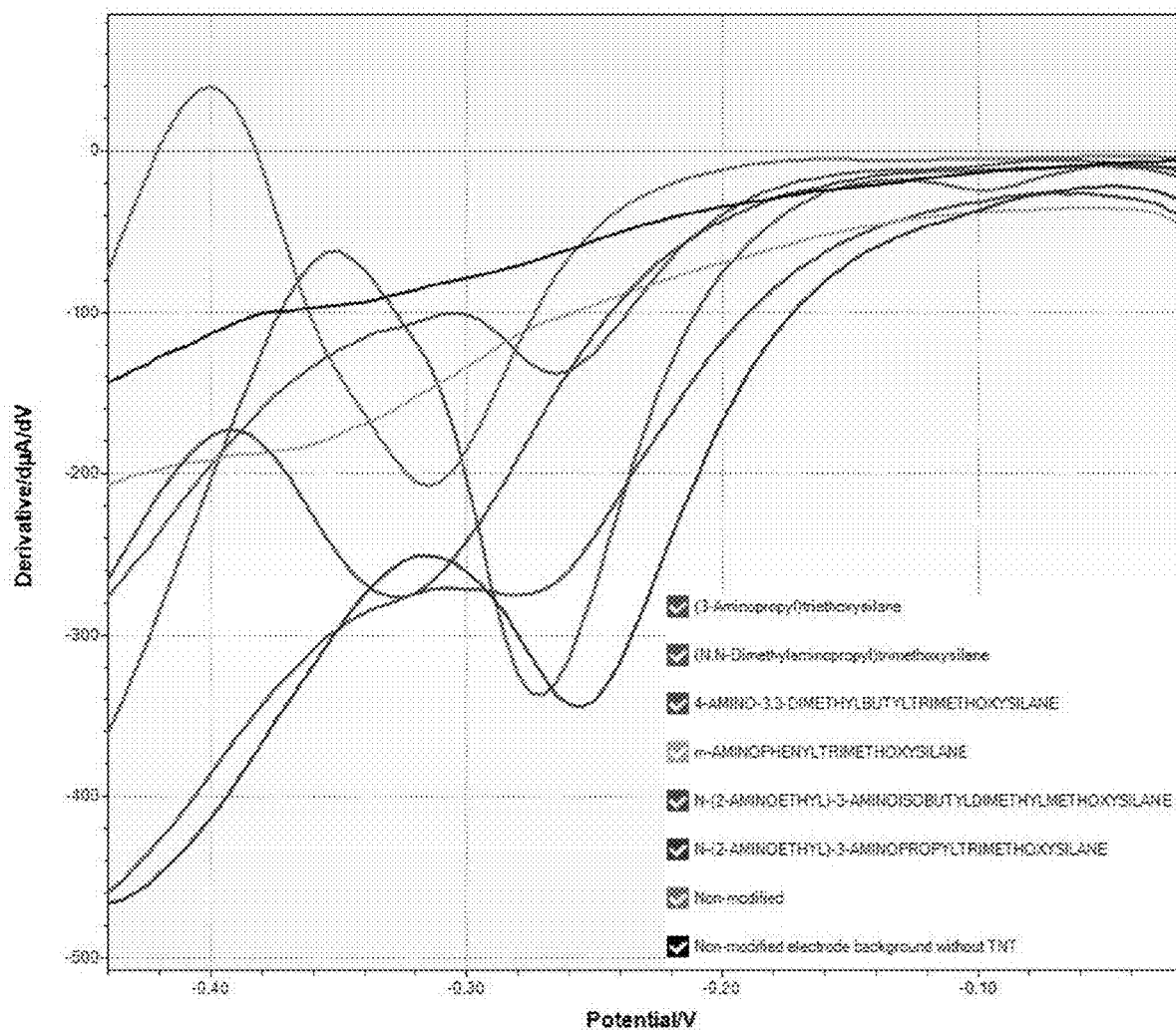
Figure 7B:
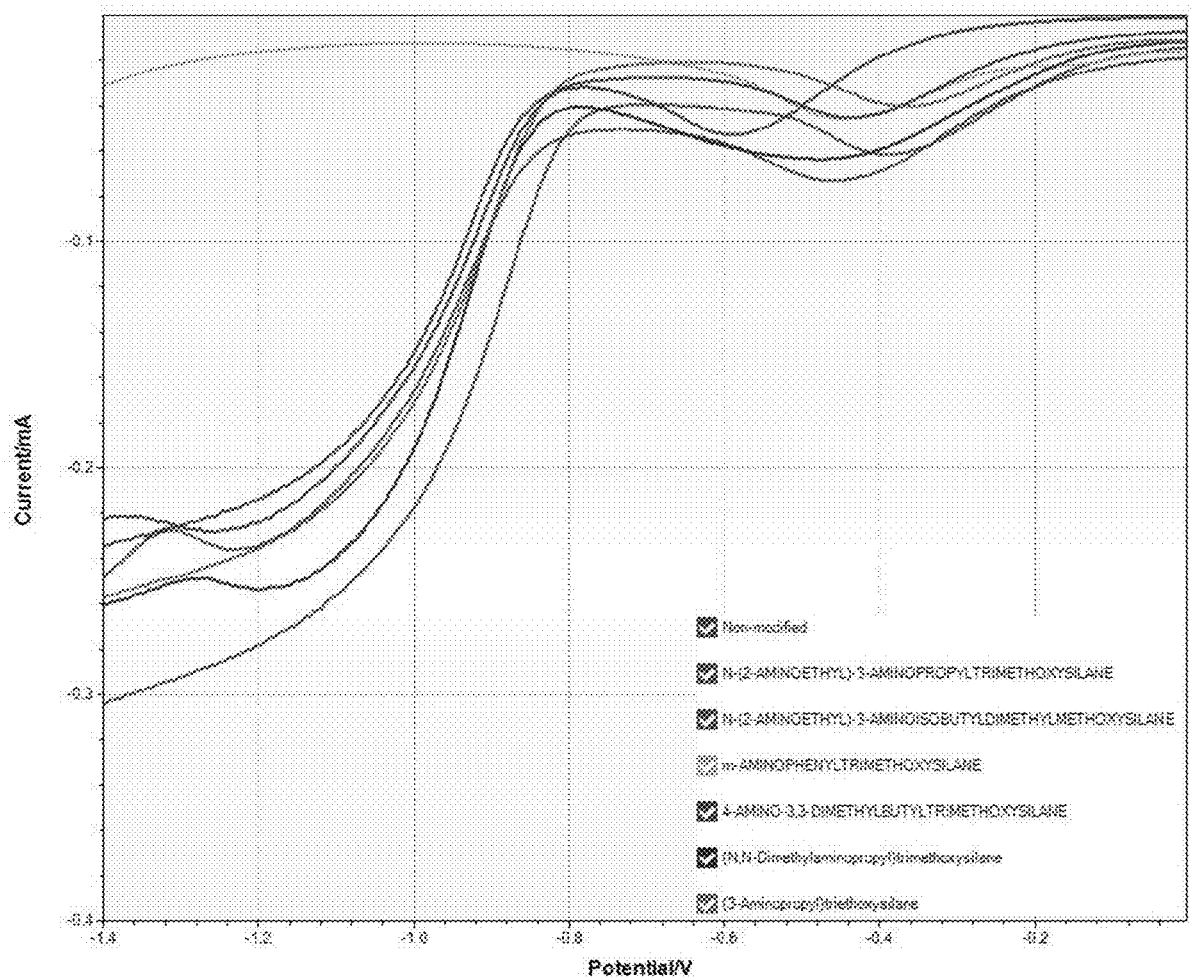

FIGS. 7A-B present data obtained in electrochemical measurements using a carbon paper microelectrode modified with varying functional groups as shown in the figure, and an electrolyte solution containing 0.25 M Potassium chloride, 5 mM tetrabutylammonium perchlorate in aqueous buffer 25 mM phosphate pH 6.6/acetonitrile mix at 7/3 aqueous/organic solution volume ratio, upon introducing TNT, 1 ppm, to the cell as vapors (FIG. 7A), and upon introducing RDX, 2 ppm, to the cell as vapors (FIG. 7B).

Figure 8A:
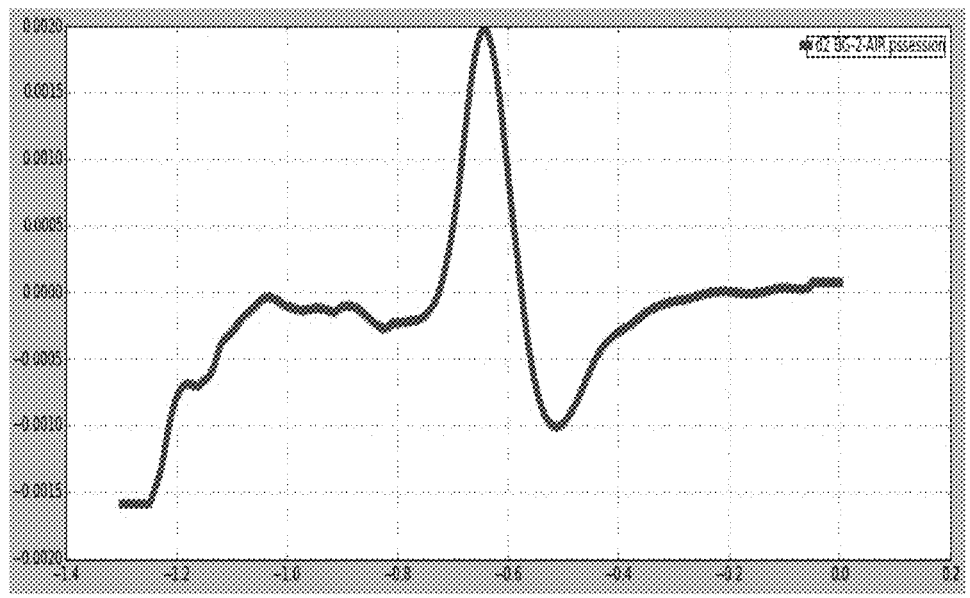
Figure 8B:
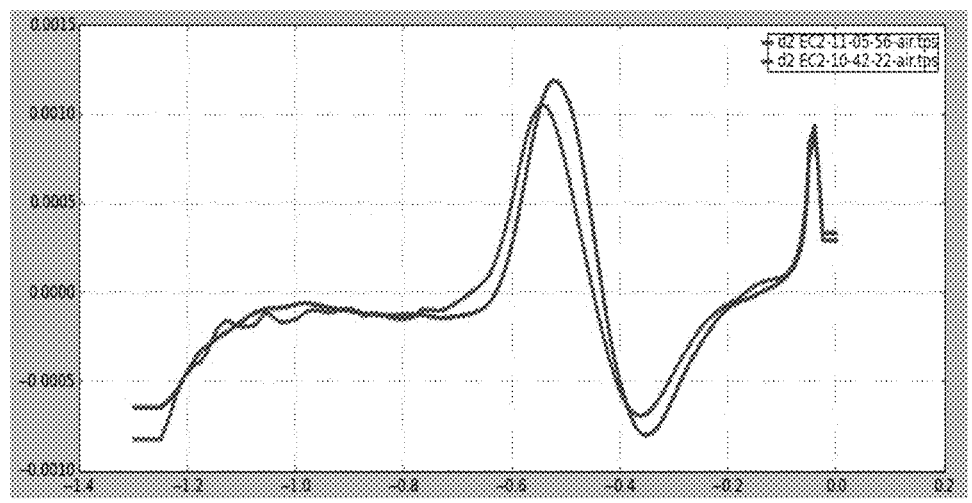
Figure 8C:
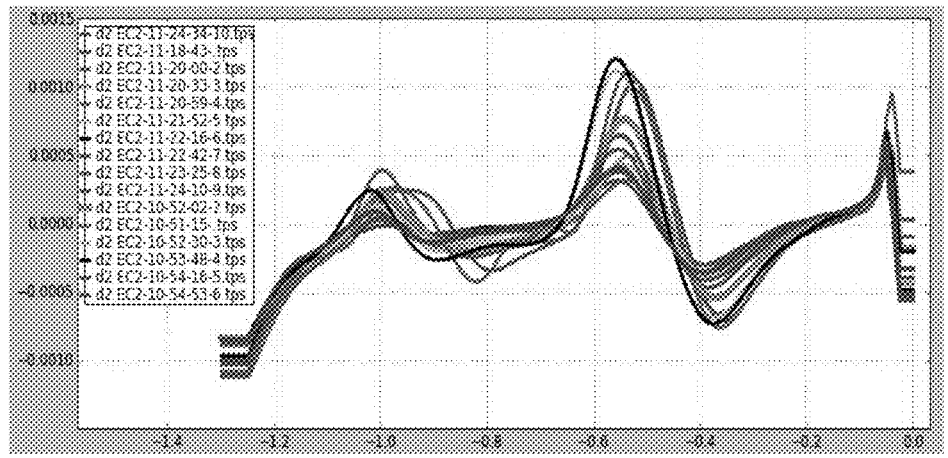
Figure 8D:
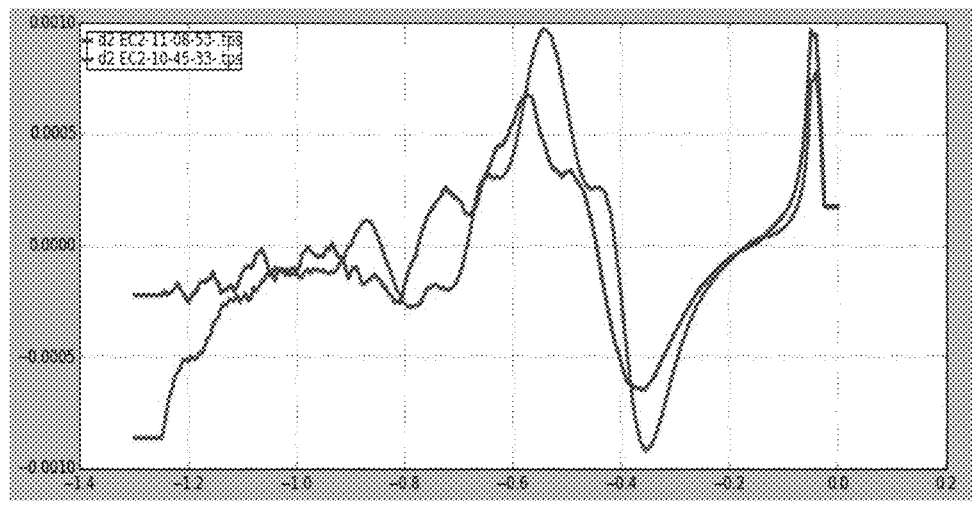

FIGS. 8A-D present the data obtained with non-modified ELAT Hydrophilic Plain Cloth® electrode upon introducing air (FIG. 8A), and with APDMES-modified ELAT Hydrophilic Plain Cloth® electrode upon introducing air (FIG. 8B), RDX (FIG. 8C) and TNT (FIG. 8D).

Figure 9A:
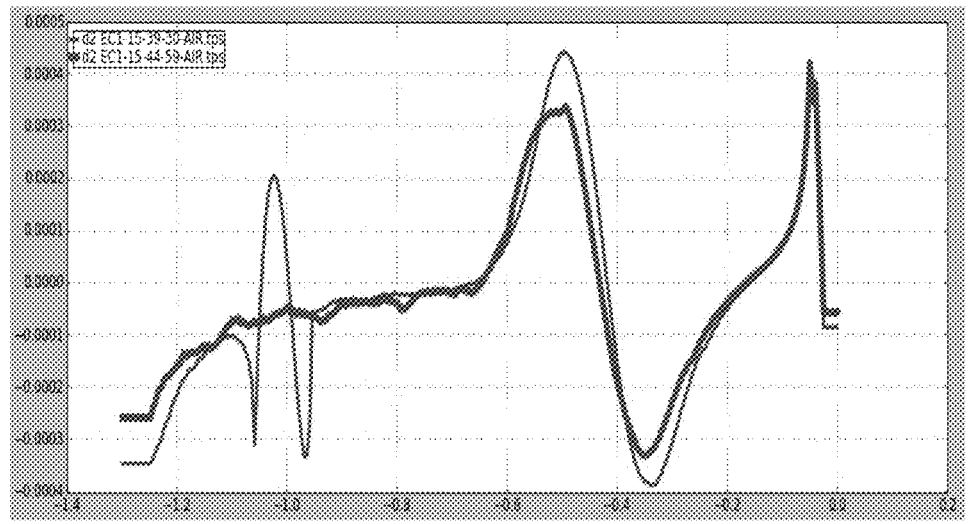
Figure 9B:
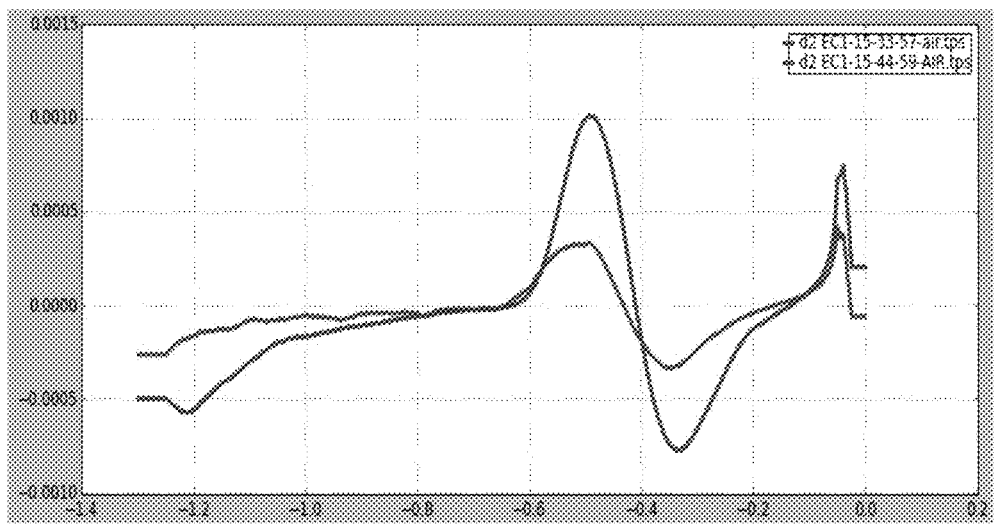
Figure 9C:
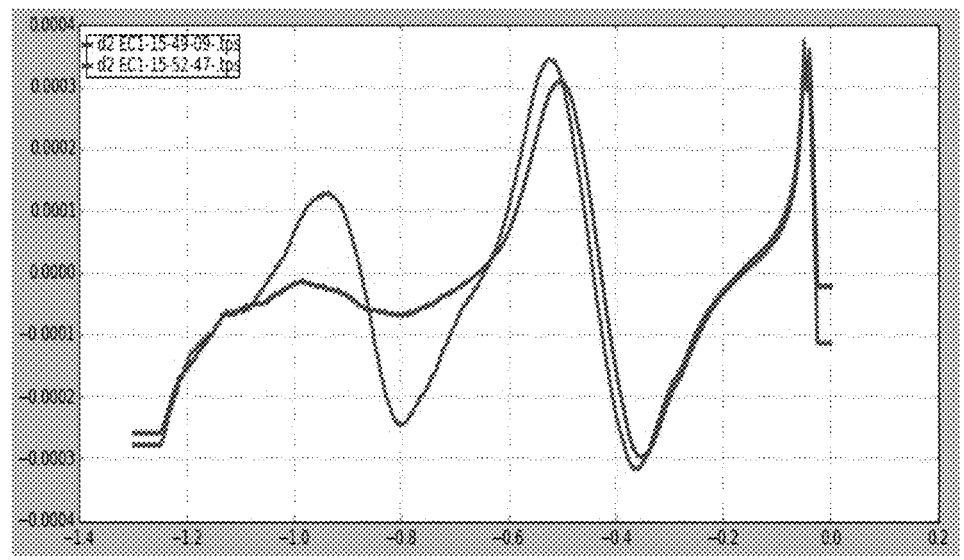
Figure 9D:
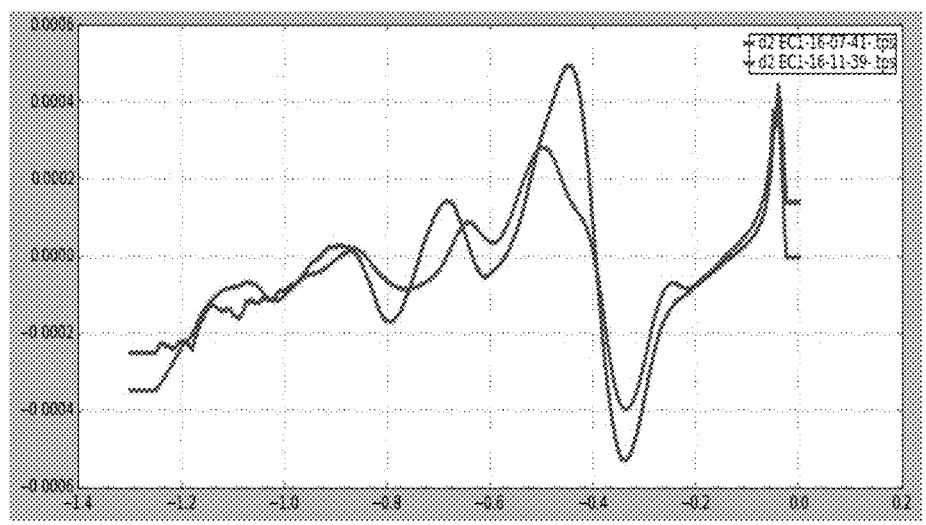

FIGS. 9A-D present the data obtained with non-modified 1071 HCB Plain Carbon Cloth electrode upon introducing air (FIG. 9A), and with APDMES-modified 1071 HCB Plain Carbon Cloth electrode upon introducing air (FIG. 9B), RDX (FIG. 9C) and TNT (FIG. 9D).

Figure 10A:
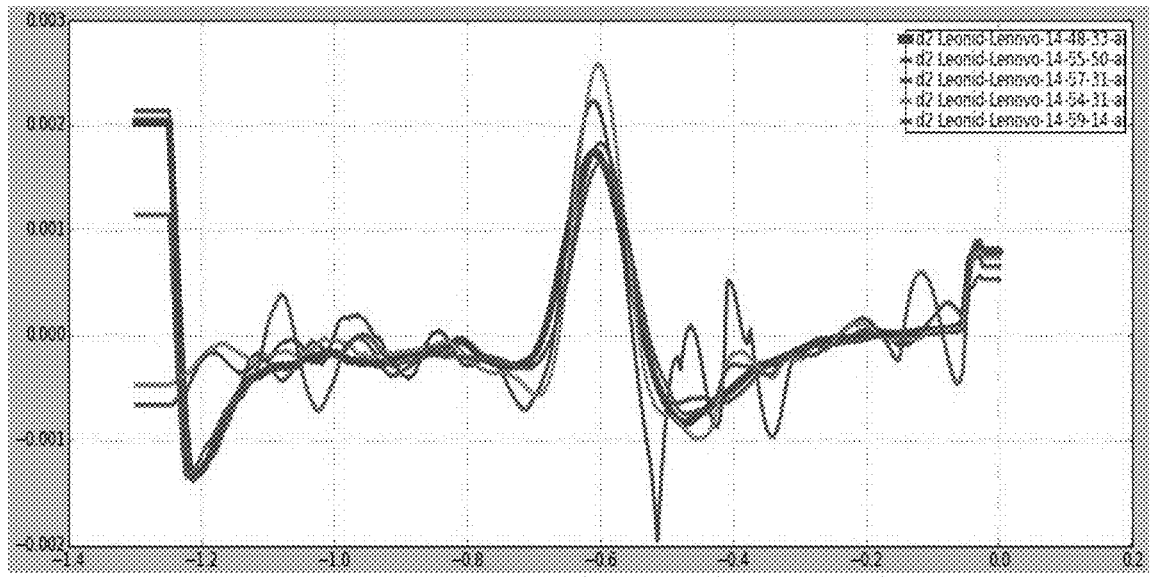
Figure 10B:
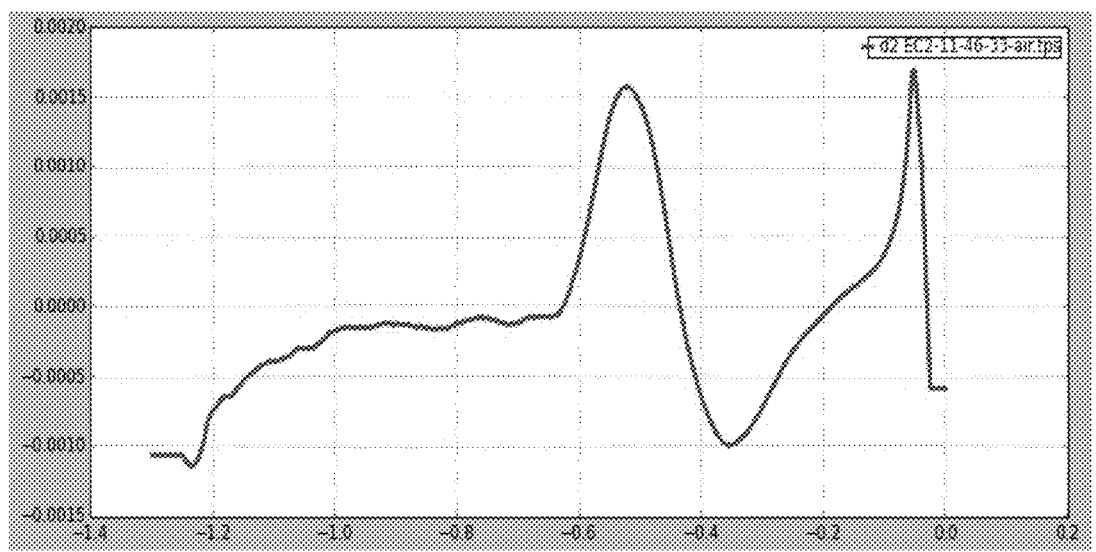
Figure 10C:
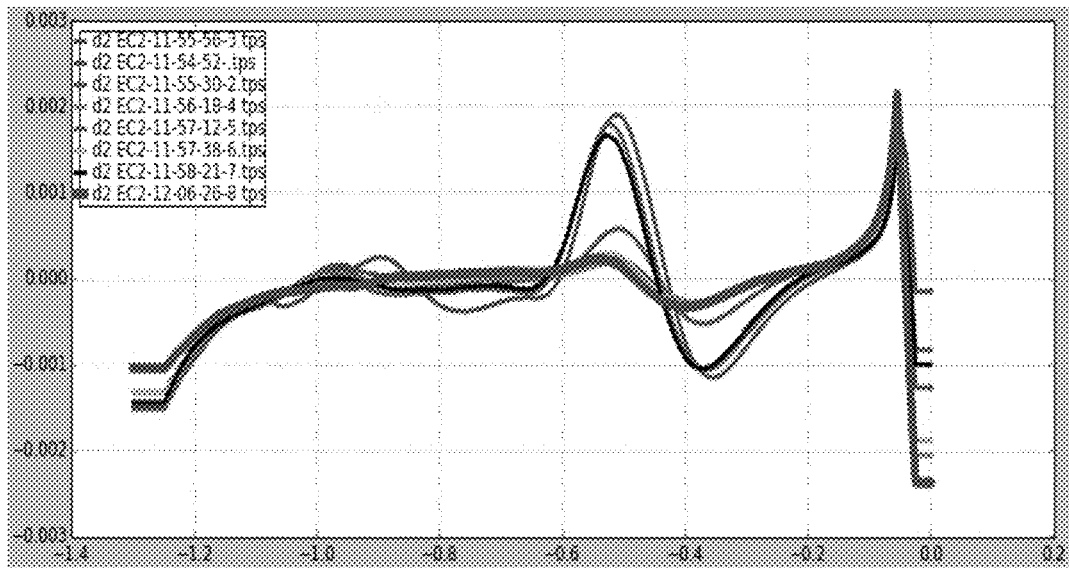
Figure 10D:
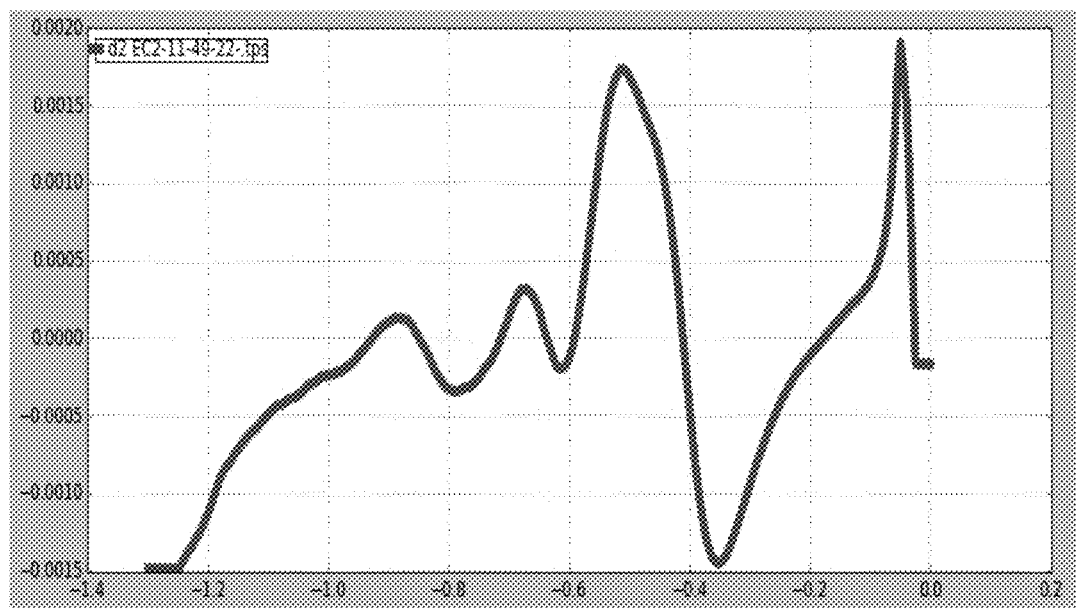

FIGS. 10A-D present the data obtained with non-modified Panex 30 Carbon Fiber Fabric electrode upon introducing air (FIG. 10A), and with APDMES-modified Panex 30 Carbon Fiber Fabric electrode upon introducing air (FIG. 10B), RDX (FIG. 10C) and TNT (FIG. 10D).

Figure 11A:
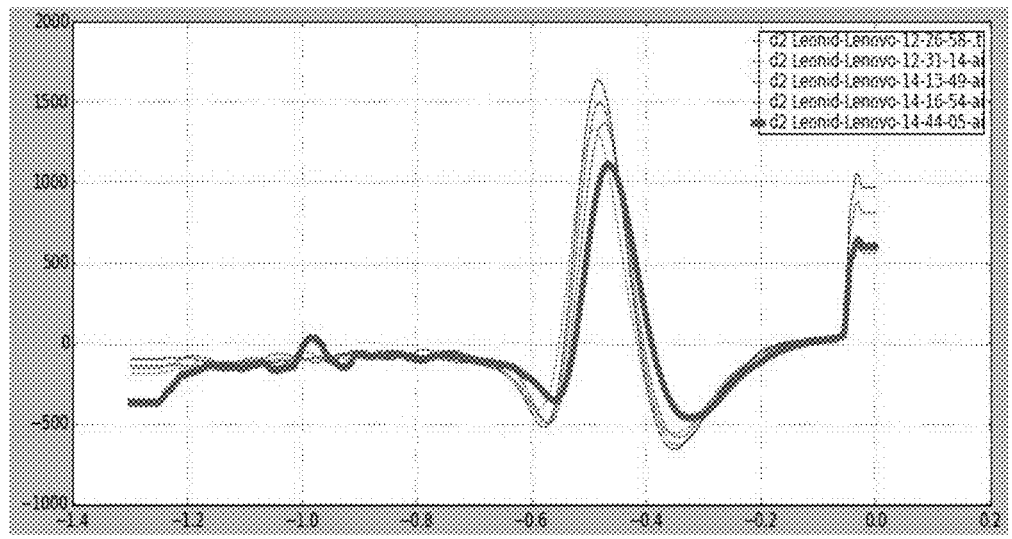
Figure 11B:
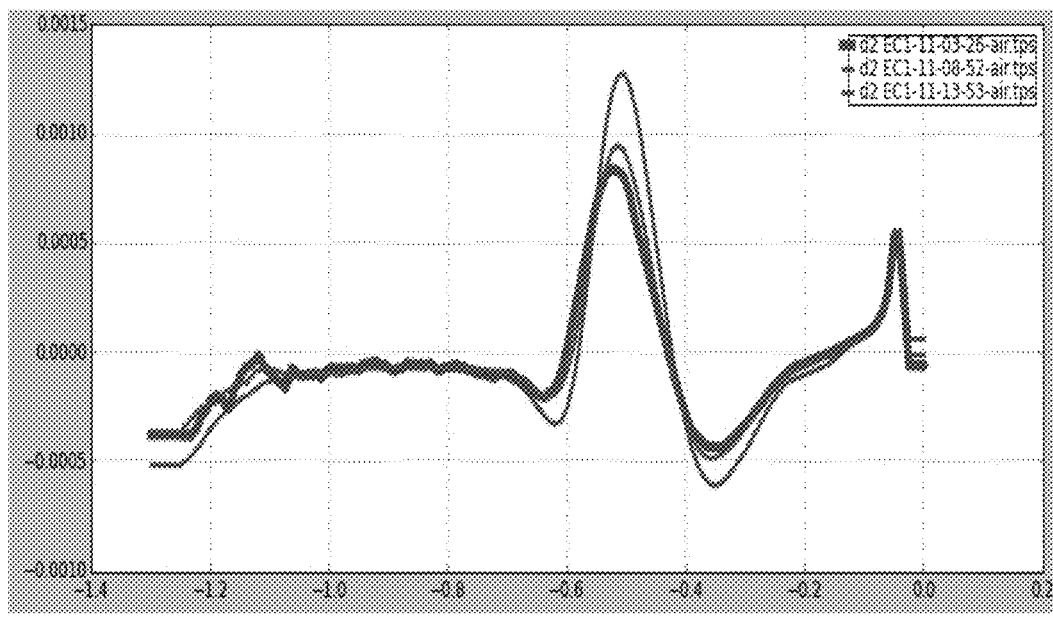
Figure 11C:
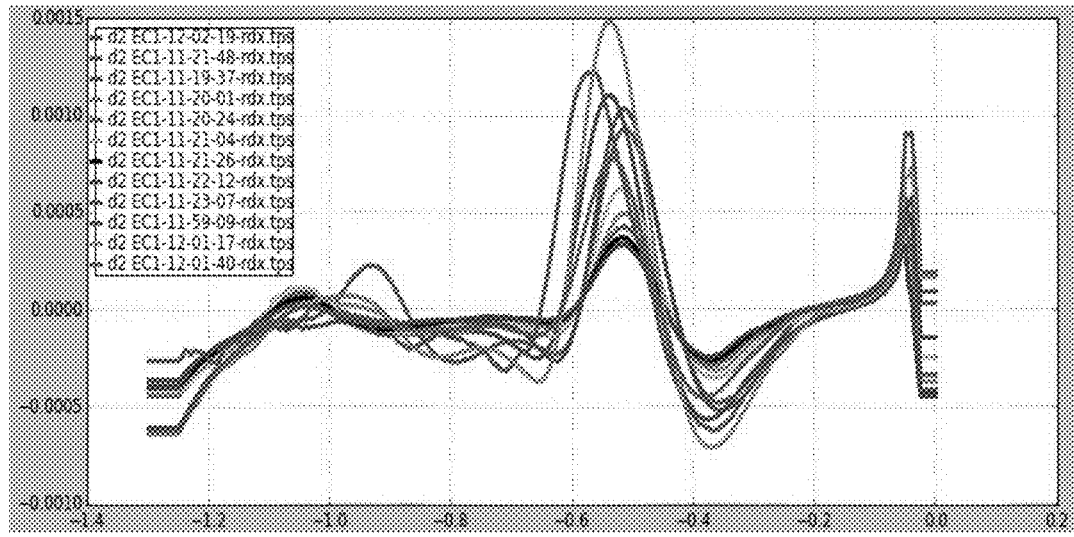
Figure 11D:
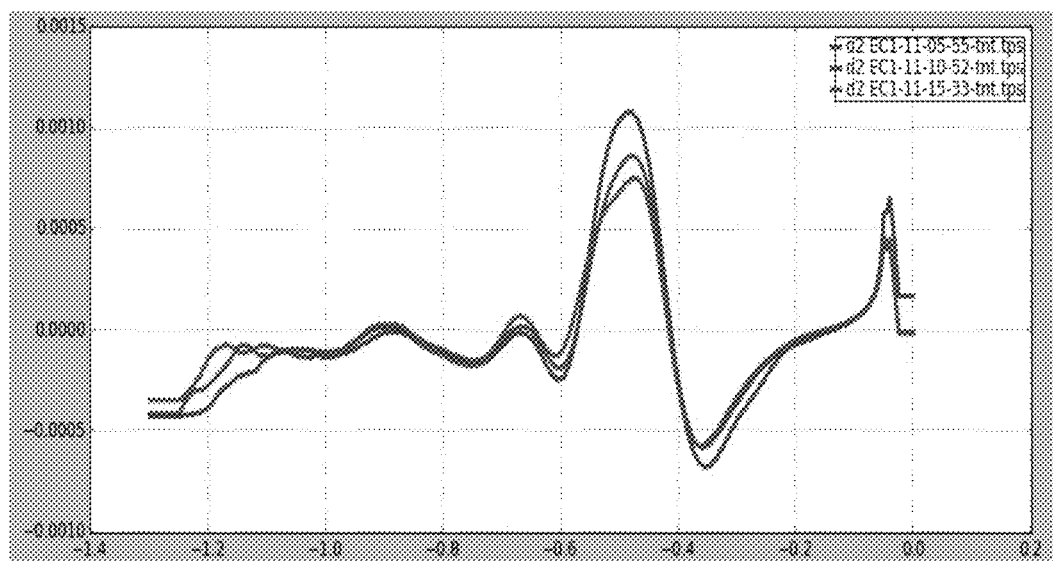

FIGS. 11A-D present the data obtained with non-modified Freudenberg H23 Carbon paper electrode upon introducing air (FIG. 11A), and with APDMES-modified Sigracet 39AA Carbon paper electrode upon introducing air (FIG. 11B), RDX (FIG. 11C) and TNT (FIG. 11D).

Figure 12A:
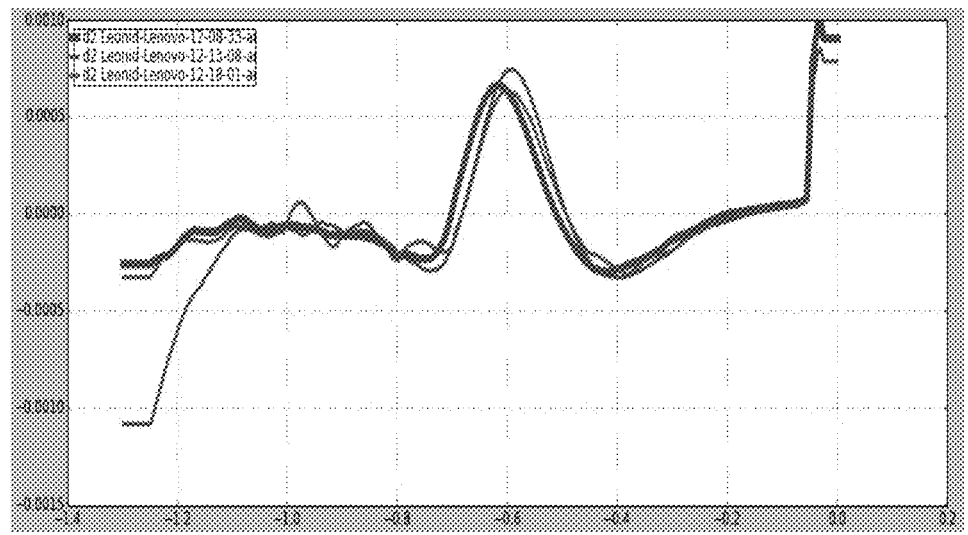
Figure 12B:
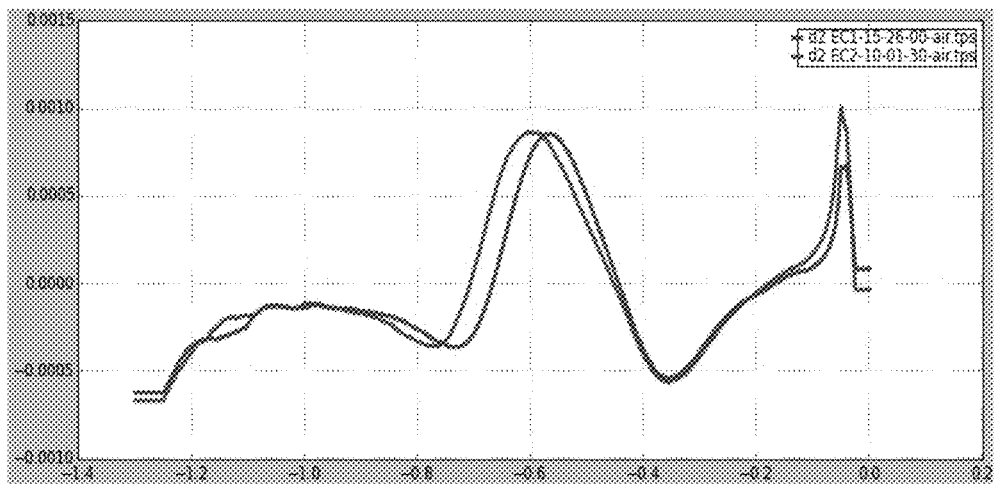
Figure 12C:
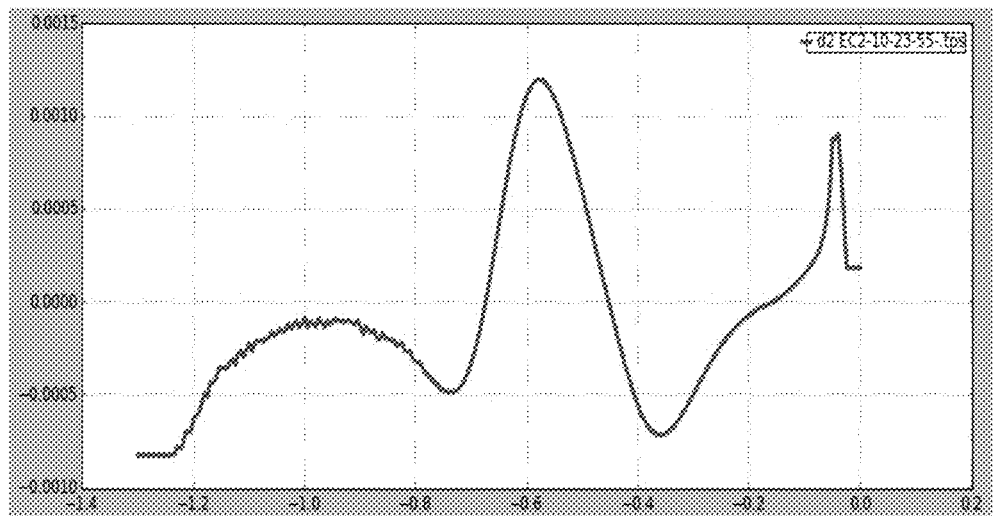
Figure 12D:
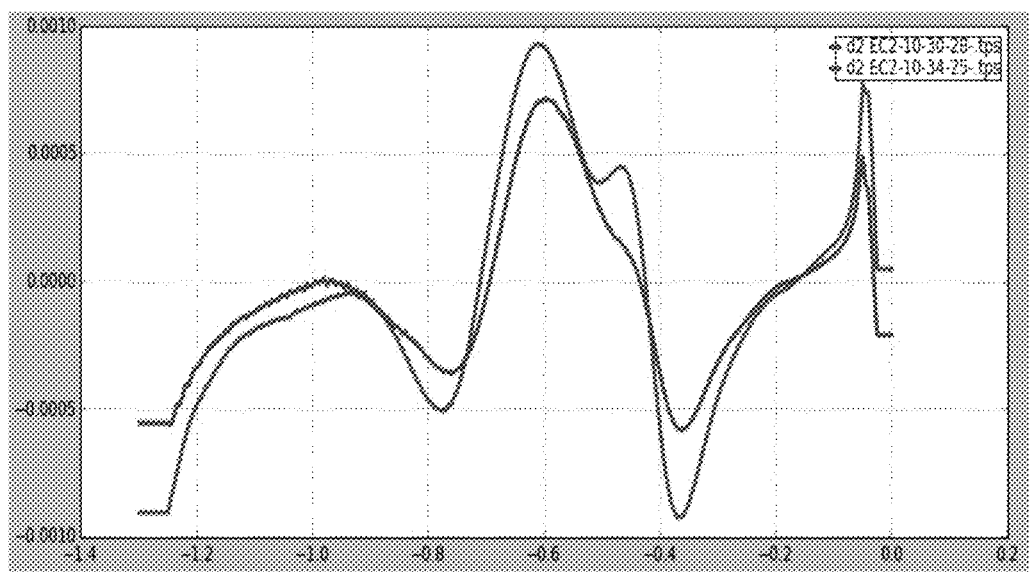

FIGS. 12A-D present the data obtained with non-modified Sigracet 39AA Carbon paper electrode upon introducing air (FIG. 12A), and with APDMES-modified Freudenberg H23 Carbon paper electrode upon introducing air (FIG. 12B), RDX (FIG. 12C) and TNT (FIG. 12D).

DESCRIPTION OF SPECIFIC EMBODIMENTS OF THE INVENTION

The present invention, in some embodiments thereof, relates to detection of chemicals and, more particularly, but not exclusively, to novel electrodes, and to systems and methods employing same, which are usable in electrochemical detection of nitro-containing chemicals such as nitro-containing explosives.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In a search for improved systems for electrochemical detection of nitro-containing compounds, which feature enhanced selectivity and sensitivity while avoiding complicate and time-consuming procedures, the present inventors have recognized that a working electrode which is made of a flexible material that can be easily and stably modified, and which can be manipulated so as to optimize its surface, to thereby increase its sensitivity, is desirable.

The present inventors have particularly sought for a system that allows manipulating the oxygen reduction kinetics so as to perform electrochemical detection of nitro-containing compounds in electrolyte solutions while overcoming the reduced sensitivity that results from the presence of dissolved oxygen. The present inventors have recognized that influencing the oxygen background signal (peak) without time-consuming steps (e.g., while circumventing the need to perform deaeration) can be effected by chemically modifying the surface of the working electrode or/and using a suitable electrochemical background.

While conceiving the present invention, the present inventors have considered utilizing carbon electrodes, due to the flexibility of carbon materials, and have particularly conceived carbon fiber microelectrodes as featuring a morphology that allows suitable signal-to-noise ratio, and which can potentially serve as effective, low cost and sensitive sensor element which meets the strict requirements of detection of explosive traces.

While reducing the present invention to practice, the present inventors have utilized electron-donating groups which can form a charge-transfer complex with the electrophilic nitro group(s) in nitro-containing compounds. The present inventors have conceived that the formation of such complexes on the surface of a carbon electrode would allow selective concentration of the nitro-containing analyte on the electrode's surface so as to increase sensitivity. Additionally, the present inventors have sought for conditions that would provide efficient detection in an environment containing dissolved oxygen, so as to provide a controlled electrochemical background and circumvent the need to perform de-aeration of the system before detection.

As demonstrated in the Examples section that follows, the present inventors have indeed designed a sensing system which can detect simultaneously trace amounts of nitro-aromatic, nitrate-ester and nitro-amine explosives in a single cycle in the presence of dissolved oxygen. The electrochemical system exhibits high sensitivity, allows detecting nitro-containing compounds at a concentration as low as 1-10 ppb, allows performing real-time and continuous monitoring of nitro-containing compounds, is operated by rapid procedures, while avoiding time consuming processes of purification and pre-concentration, allows detection within about 10-20 seconds, is free of a labeling agent, and thereby circumvents the need to use excitation and imaging techniques, enables detecting simultaneously several nitro-containing compounds; is easy to integrate with a lab on chip system/electrochemical system, can be operated with small volume sample; is reusable; and uses low-cost and low-energy constructions and operation.

The designed electrochemical system, by being capable of efficiently detecting nitro-containing compounds in the presence of dissolved oxygen, can be utilized, for example, in aqueous environments such as sea water, and in containers, open fields, and any other oxygen-containing environments. The system can furthermore be efficiently used for detecting nitro-containing compounds in air samples.

The system can be configured so to feature minimized dimensions, efficient and user-friendly delivery means for introducing the sample to the system, at the user interface.

Referring now to the drawings, FIG. 1 presents a schematic illustration of an exemplary electrochemical cell usable in the context of the present embodiments and comprising a sensing (working) electrode 16 as described herein.

FIG. 2A presents a schematic illustration of a process of preparing an exemplary sensing electrode according to some embodiments of the present invention. The electrode is simply prepared by generating free hydroxy groups on the carbon fiber electrode's surface and introducing, by covalent attachment of a siloxane to the hydroxy groups on the electrode's surface, electron-donating groups such as amines, which form charge-transfer complexes with the electron-deficient nitro groups. FIG. 2B presents an exemplary device for practicing the preparation of sensing electrodes according to some of the present embodiments.

FIG. 3A presents data obtained in differential pulse voltammetry using a non-modified carbon fiber (CF) microelectrode (CP; black line) and an exemplary amino modified CF microelectrode (CP-APDMES; red line), according to some embodiments of the present invention. Measurements were performed while using an exemplary background solution, according to some embodiments of the present invention, containing 0.25 M Potassium chloride, 5 mM Tetrabutylammoniumiodide in aqueous buffer phthalate pH 4.0/acetonitrile mixture at 7/3 volume ratio, respectively. As shown in FIG. 3A, a decrease of 200 mVolts in the oxygen reduction potential is observed with an electrode according to the present embodiments.

FIG. 3B presents data obtained in differential pulse voltammetry using a non-modified carbon fiber (CF) microelectrode (black line) and a CF microelectrode upon treatment with oxygen plasma (red line), according to some embodiments of the present invention. Measurements were performed while using an exemplary background solution, according to some embodiments of the present invention, containing 0.25 M Potassium chloride, 5 mM Tetrabutylammoniumiodide in aqueous buffer phthalate pH 4.0/acetonitrile mixture at 7/3 volume ratio, respectively. As shown in FIG. 3B, a decrease of more than 200 mVolts in the oxygen reduction potential is observed with an electrode according to the present embodiments.

FIGS. 4A-C present differential pulse voltammetry fingerprints (left) and calibration curves (right) of various nitro-containing compounds, featuring structural variability, at varying concentrations, and at a combination thereof. As shown therein, the herein disclosed system allows performing a detection of all nitro-containing compounds, and of optional combinations thereof, in the presence of dissolved oxygen, since it differentiates between the reductions peaks of the various nitro-containing compounds and of the dissolved oxygen.

FIGS. 5A-G and 6 present linear sweep voltammetry measurements performed with modified electrodes according to some of the present embodiments at varying pH, showing that the electrochemical detection can be performed at varying pH values lower than 8. FIGS. 7A and 7B show the variability of the possible chemical modifications of the carbon electrode that allow successful detection of various nitro-containing compounds, which further allow generating fingerprints for each nitro-containing compound using an array of differently modified electrodes.

FIGS. 8A-12D the variability of carbon fiber electrodes that are usable in the context of the present embodiments.

These data clearly demonstrate that a sensing system according to the present embodiments enable to perform sensitive, selective, multiplex and high sampling rate electrochemical detection of nitro-containing compounds such as nitro-containing explosives.

Embodiments of the present invention therefore provide an improved sensing electrode, and a sensing system and method utilizing same for detecting nitro-containing compounds in a sample, which are particularly usable in detecting nitro-containing compounds in the presence of dissolved oxygen.

Sensing Electrode:

A sensing electrode according to embodiments of the present invention comprises a carbon electrode and a functional moiety covalently attached to a surface of the electrode, or to a portion of the surface, the functional moiety being such that forms a charge-transfer complex with a nitro-containing compound.

According to some embodiments of the present invention, the carbon electrode features at least one nanoscale or microscale dimension.

By "microscale dimension" it is meant that at least one dimension of the electrode is lower than 1 mm, or ranges from 0.1 micron to 900 microns.

By "nanoscale dimension" it is meant that at least one dimension of the electrode is lower than 1 micron, or ranges from 0.1 nanometer to 900 nanometers.

The nanoscale or microscale dimension depends on the shape of the electrode. If an electrode is generally shaped as a cylinder, the at least one dimension can be one or both of a length and a diameter of the electrode. If the electrode is generally shaped as a rectangular, the at least one dimension can be one or more of a length and a width of the electrode.

Electrodes featuring one or more microscale or nanoscale dimension are also referred to herein and in the art as microelectrodes.

Carbon electrodes or microelectrodes can be made of glassy carbon, screen-printed carbon, carbon films, carbon fibers, carbon paste, carbon nanotubes and others.

According to some embodiments of the present invention, the carbon electrode is a carbon fiber electrode, or a carbon fiber microelectrode (also referred to herein interchangeably as "carbon microfiber electrode").

A carbon fiber (CF) electrode is an electrode that comprises elementary carbon (e.g., graphite) shaped as a fibrous structure (e.g., a filament). Generally, but not necessarily, a CF electrode features a microscale or even nansoclae diameter or thickness (width), typically, but not limited to, in a range of from 1 to 500 microns, or from 5 to 200 microns, or 5 to 100 microns, or 5 to 50 microns or 5 to 20 microns. Generally, but not necessarily, a CF electrode features a length (height) of from about 100 microns to about 50 mm, or from about 100 microns to about 1 mm, or from about 100 microns to about 800 microns, including any intermediate values and subranges therebetween. CF electrode featuring at least one dimension in the microscale or nanoscale range is a CF microelectrode.

In some embodiments the CF microelectrode further comprises a mechanical support enveloping or surrounding at least a portion of the electrode, leaving a protruding tip of e.g., from 10 to 100 microns, of unsupported, exposed portion of the electrode.

The CF microelectrode can be a single-barrel or a multi-barrel electrode.

In some embodiments, a CF microelectrode is a gas-permeable electrode. Gas permeable electrodes allow sensing of gaseous samples (e.g., air) and/or analytes while circumventing the need to introduce the sample via a dedicated gas inlet.

By "gas-permeable" it is meant that the electrode is characterized by air permeability through plane higher than 0.3 cfm/ft$^2$ through 0.25 mm, when measured according to standard assays such as ASTM 737-96, ISO 5636, ISO 4638, ISO 9237, and TAPPI T460.

The CF microelectrodes can be carbon fabric electrodes or carbon paper electrodes. Carbon fabric electrodes can be made of woven or non-woven carbon filaments or bundles of filaments. Both electrode types are preferably gas-permeable electrodes.

Exemplary commercially available gas-permeable carbon fabric microelectrodes that are usable in the context of the present embodiments include, but are not limited to, plain carbon cloth such as, for example, electrodes marketed as ELAT—Hydrophilic Plain Cloth®, 1071 HCB plain carbon cloth, Panex 30®.

Exemplary commercially available gas-permeable carbon paper microelectrodes that are usable in the context of the present embodiments include, but are not limited to, electrodes marketed by Freudenberg FCCT, such as Freudenberg H23, electrodes of the Spectracarb™ family, Sigracet 39 AA, electrodes marketed under the trade name AvCarb® (e.g., AvCarb P75), and similar gas-permeable carbon paper electrodes.

Any commercially available CF microelectrode can serve as a raw material for providing a CF microelectrode according to the present embodiments, upon generating on at least a part of its surface a functional moiety as described herein.

In some of any of the embodiments described herein, a CF microelectrode is a carbon paper electrode.

In some of any of the embodiments described herein, the CF microelectrode (e.g., the carbon fiber microelectrode) is characterized by a surface area of at least 10-50 cm$^2$ per geometrical cm$^2$, including any intermediate value and subranges therebetween.

In some embodiments, the CF microelectrode is electrically connectable to other parts of a sensing system via electrically conducting wires, for example, conducting metal foils such as, but not limited to, Ni foils.

The CF microelectrode of the present embodiments features (carries, exhibits) a functional moiety in at least a portion of its surface (e.g., an exposed portion of the electrode's surface).

In some of any of the embodiments described herein, the CF microelectrode features (carries, exhibits) a plurality of functional moieties as described herein in at least a portion of its surface.

In some of any of the embodiments described herein, the CF microelectrode of the present embodiments features a functional moiety attached to at least a portion of its surface (e.g., an exposed portion of the electrode's surface), and in some embodiments the functional moiety is covalently attached to the at least a portion of the surface.

In some of any of the embodiments described herein, the CF microelectrode features a plurality of functional moieties as described herein attached to at least a portion of its surface, and in some of these embodiments at least a portion, and preferably most or all, of the functional moieties are covalently attached to the at least a portion of the surface.

In some of any of the embodiments described herein, an average density of the functional moieties on the CF microelectrode surface is at least $10^{10}$ moieties per cm$^2$, or at least $10^{11}$ moieties per cm$^2$, and can be, for example, from about $10^{10}$ to about $10^{13}$, or from about $10^{11}$ to about $10^{13}$, functional moieties per cm$^2$ of the electrode's surface.

In some of any of the embodiments described herein, the functional moiety is such that interacts with a nitro-containing compound by forming a charge transfer complex therewith.

As defined in IUPAC, a "charge-transfer complex" is a complex of an electron donor and an electron acceptor, characterized by electronic transition(s) to an excited state in which there is a partial transfer of electronic charge from the donor to the acceptor moiety.

Since the nitro group in nitro-containing compounds acts as an electron-withdrawing group, nitro-containing compounds typically comprise domains which are electron deficient and may exhibit a partial positive charge, due to electron resonance between these domains and the nitro group(s).

In some of any of the embodiments described herein, the functional moiety is or comprises an electron donating moiety.

Without being bound by any particular theory, it is assumed that the electron donating moiety forms a charge transfer complex with the positively charged domains in nitro-containing compounds.

Thus, in some of any of the embodiments described herein, in a charge-transfer complex as described herein, the electron donor in an electron-donating moiety attached to the CF electrode by means of a modified nanostructure, as described herein, and the electron-acceptor is the nitro-containing moiety.

As used herein, the phrase "electron donating" with respect to a moiety or group describes a moiety or group that comprises at least one electron donating atom, as this phrase is defined herein.

As used herein, the phrase "electron donating atom" describes any atom in a chemical group which is capable of donating one or more electrons to an electron acceptor (e.g., an atom or a molecule that exhibits electron deficiency), so as to interact with the acceptor (e.g., via formation of a charge transfer complex). Typically, the electron donating atom is characterized by the presence of a free electron pair. Various heteroatoms (e.g., phosphorus, sulfur, nitrogen) are known in the art to be capable of acting as electron donating atoms. In addition, a carbon atom in an N-heterocyclic carbene (e.g., an N-heterocyclic carbene which is a five- or six-membered heteroalicyclic or heteroaromatic ring described herein) may be a suitable electron donating atom.

In some of any of the embodiments described herein, a length of the functional moiety is smaller than 2 nm, smaller than 1.5 nm, and even smaller than 1 nm. This allows the formation of the charge transfer complex of the nitro-containing compound and the electron donating group to occur close to the electrode surface, thereby enhancing the sensitivity of a sensing system comprising the electrode. Exemplary electron donating moieties according to the present embodiments include, but are not limited to, alkyl, alkenyl, alkynyl, aryl and cycloalkyl, each being substituted by one or more electron donating group(s).

In some of any of the embodiments described herein, a substituted alkyl, alkenyl, alkynyl, aryl or cycloalkyl as described herein is smaller than 5 nm in length, smaller than 2.5 nm, and even smaller than 1 nm.

In some of any of the embodiments described herein, the electron donating moiety is an alkyl, alkenyl or alkynyl, being from 1 to 10 carbon atoms in length, and being substituted by one or more electron donating group(s).

In some of any of the embodiments described herein, the alkyl, alkenyl or alkynyl described herein is being of from 1 to 9 carbon atoms, or from 1 to 8 carbon atoms, or from 1 to 7 carbon atoms, or from 1 to 6 carbon atoms, or from 1 to 5 carbon atoms, or from 1 to 5 carbon atoms, or from 1 to 4 carbon atoms, or from 1 to 3 carbon atoms, or from 1 to 2 carbon atoms in length, or of 1 carbon atom in length.

In some of any of the embodiments described herein, alkyl, alkenyl or alkynyl described herein is being from 1 to 3 carbon atoms in length.

In some of any of the embodiments described herein, the electron donating moiety is an alkyl being from 1 to 9 carbon atoms, or from 1 to 8 carbon atoms, or from 1 to 7 carbon atoms, or from 1 to 6 carbon atoms, or from 1 to 5 carbon atoms, or from 1 to 5 carbon atoms, or from 1 to 4 carbon atoms, or from 1 to 3 carbon atoms, or from 1 to 2 carbon atoms in length, or of 1 carbon atom in length, and in some embodiments it is an alkyl being from 1 to 4 carbon atoms in length and comprising one or more electron-donating group(s) as defined herein.

The electron-donating group(s) are preferably located at the distal terminus of the alkyl, alkenyl or alkynyl, with respect to the electrode's surface, so as to be exposed to interacting with the nitro-containing compound.

In some of any of the embodiments described herein, the electron donating moiety is a cyclic moiety, such as aryl or cycloalkyl, comprising one or more electron-donating group as substituent(s). The substituent is preferably located so as to be exposed to interacting with the nitro-containing compound.

In some of any of the embodiments described herein, the cyclic moiety is smaller than 2 mm in length and is some embodiments, the cyclic moiety comprises from 1 to 3 fused rings.

In some of any of the embodiments described herein, the functional moiety is a cyclic moiety such as a heteroalicyclic or a heteroaryl, which comprises a heteroatom that functions as an electron donating group (e.g., an electron donating atom).

In some of any of the embodiments described herein, the heteroatom is a nitrogen atom, which can be, for example, a part of a substituted or unsubstituted secondary amine with a ring of the cyclic moiety. In cases where the nitrogen atom is a substituted amine, the substituent is preferably such that enhances its electron donating properties, namely, is a substituent which features an electron inductive effect (e.g., alkyls), yet do not impart stearic hindrance (e.g., lower alkyl such as methyl or ethyl).

Exemplary electron donating groups include, but are not limited to, amine, alkoxy, thioalkoxy, aryloxy and thioaryloxy, and electron donating atoms when included in a cyclic moiety.

In some of any of the embodiments described herein, the electron donating group is amine, as defined herein. In some of these embodiments, the amine can be a primary amine, a secondary amine or a tertiary amine.

The amine can be unsubstituted, namely, be a primary amine, or substituted, namely, be a secondary amine or a tertiary amine, as defined herein. In cases where the amine is substituted, the substituent(s) is/are preferably such that enhance its electron donating properties, namely, are substituents which feature an electron inductive effect (e.g., alkyls), yet do not impart stearic hindrance (e.g., lower alkyl such as methyl or ethyl).

In some of any of the embodiments described herein, the electron donating group is an amine and the amine is a primary amine.

In some of any of the embodiments described herein, the electron donating group is an amine and the amine is a secondary amine.

In some of any of the embodiments described herein, the electron donating moiety is an aminoalkyl, the alkyl being 1-10 carbon atoms in length.

In some embodiments, the alkyl is being 1-5 carbon atoms in length.

In some embodiments, the electron donating moiety is aminopropyl.

In some embodiments, the electron donating moiety is N-methylaminopropyl.

It is to be further noted that stronger electron donating property of the electron donating moiety enables interaction with nitro-containing compounds which exhibit lower electron deficiency.

For example, while TNT exhibits a high extent of electron deficiency, compounds with less nitro substituents or aliphatic nitro-containing compounds can be less sensitive for a detection method that utilizes aminopropyl electron donating moiety, yet, such compounds will interact in a method that utilizes a stronger electron donating moiety such as, for example, N-methylpropylamine.

In some of any of the embodiments described herein the functional moiety comprises a silicon atom substituted by one or more of the electron donating moieties described herein.

In some of any of the embodiments described herein the functional moiety comprises a silyl substituted by one or more of the electron donating moieties described herein.

In some of any of the embodiments described herein, the functional moiety comprises an orthosilicate (silyl ether; siloxane) substituted by one or more of the electron donating moieties described herein.

In some of any of the embodiments described herein, the silyl or siloxane is further substituted by one or more substituents, as described herein, preferably by hydrocarbon substituents such as alkyls, alkenyls, alkynes, cycloalkyls, alkaryls and/or aryls, each being optionally substituted.

In some embodiments, the silyl or siloxane is substituted by one or more alkyls, preferably medium or lower alkyls as described herein, for example, one or two methyl substituents.

Without being bound by any particular theory, it is assumed that the hydrophobic substituents, such as hydrocarbon substituents, of a silicon atom, stabilize the chemical modification on the electrode surface, for example, by reducing interaction with (repulsing) nucleophilic species such as hydroxy ions, present in the system, which can lead to decomposition of the silicon nanostructures.

In some of any of the embodiments described herein, the functional moiety is represented by the following Formula I:

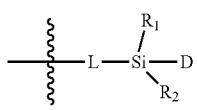

Formula I wherein the curved line denotes an attachment point to the electrode's surface (e.g., to a reactive group on the electrode's surface);

D is an electron donating moiety as described herein;

$R_1$ and $R_2$ are each independently a hydrocarbon substituent as described herein, an alkoxy, an aryloxy, hydrogen, an electron donating moiety as described herein (D) or L (having also an attachment point to a reactive group on the electrode's surface); and L is a bond, or is oxygen, or is generated upon covalent coupling of a second reactive group as described herein to a first reactive group on the electrode's surface.

In some embodiments, $R_1$ and $R_2$ are each independently an alkyl as described herein, and in some embodiments $R_1$ and $R_2$ are each methyl.

In some embodiments, L is oxygen, such that the functional moiety is covalently attached to the electrode's surface by a —Si—O— bond.

Functional moieties represented by Formula I in which D comprises an amine as an electron donating group are also referred to herein as amino-siloxanes or as moieties generated from amino-siloxanes.

In some embodiments, the functional moiety is attached to the electrode's surface by a single —Si—O— bond. In some embodiments, such functional moieties form a monolayer in the electrode's surface.

In some embodiments, the functional moiety is covalently attached to the electrode's surface by means of forming covalent bonds between a reactive group in a compound from which the functional moiety is derived and a compatible reactive group on the surface of the electrode. The functional moiety is the moiety formed upon such a covalent attachment of the compound to the reactive group on the electrode's surface.

For example, a functional moiety represented by Formula I, in which L is oxygen, is generated from a corresponding siloxane or orthosilicate, which features, instead of the oxygen, a hydroxy, alkoxy or aryloxy group.

Reactive groups on the electrode's surface are either intrinsic or can be generated upon a suitable treatment.

In some embodiments, a CF microelectrode as described herein is surface-modified so as to generate surface reactive groups (also referred to herein as first reactive groups). Such a surface modification can be performed by, for example, attaching to intrinsic functional groups on the surface a bifunctional linker molecule, which comprises in one terminus thereof a reactive group that is capable of forming a bond with these intrinsic functional groups and in another terminus thereof a reactive group that can form a bond with the functional moiety (that is, with a reactive group of a compound that generates the functional moiety). Such a surface modification can alternatively comprise other treatments which generate surface reactive groups (e.g., by oxidation or reduction of intrinsic functional groups on the electrode's surface). Exemplary methods for chemically modifying electrodes include, but are not limited to, coating with a polymer film, covalent attachment of functional moieties, sol-gel technology, physical adsorption, and oxygen plasma treatment.

In some embodiments, the generated surface (first) reactive groups render the electrode, or a portion thereof, reactive towards, for example, oxygen reduction, and thereby accelerate the oxygen reduction and improves the sensing efficiency.

Thus, surface-modified CF electrodes provide for both reactive groups for covalently attaching the functional moieties to the electrode's surface and reactive groups that improves the sensing efficiency in the presence of oxygen.

In some embodiments, the compound generating the functional moiety comprises, prior to being attached to the electrode, a reactive group that can readily react with a (first) reactive group on the electrode's surface so as to form a covalent bond with the surface. Such a reactive group is also referred to herein as a second reactive group.

In some of any of the embodiments described herein the electrode is a surface-modified electrode as described herein, which features surface hydroxy groups (also referred to herein as first reactive groups). These surface reactive groups can participate in the covalent attachment of the functional moiety thereto, via a compatible reactive group in the compound generating the functional moiety (also referred to herein as a second reactive group).

Selecting (second) reactive groups that are compatible with (first) reactive groups on the electrode of choice is within the capabilities of any person skilled in the art, particularly in view of the guidance provided herein.

In some embodiments, a carbon fiber electrode features, or is modified so as to feature, hydroxy (first) reactive groups on its surface and the compound generating the functional moiety comprises a (second) reactive group capable of forming covalent bond with the free hydroxy groups on the electrode's surface. Exemplary such (second) reactive groups include, but are not limited to, halides and alkoxides, which can act as leaving groups so as to form an ether bond, carboxylic acids or esters, which can form an ester bond via esterification or trans esterfication, as well as halosilanes and orthosilicates (siloxanes), which can form —SI—O— bonds, as exemplified herein by Formula I.

According to some embodiments of the invention, the functional moiety is attached to the nanostructure via any one of the bonds described herein.

According to some embodiments of the invention, the functional moiety is attached to the nanostructure via a —O—S— bond.

Free hydroxy groups on a carbon fiber electrode's surface can be generated, for example, by oxygen plasma treatment.

In some embodiments, the electron donating moiety is an aminoalkyl and the functional moiety is derived from an aminoalkyltriorthsilicate, such as, for example, aminopropyltriorthosilicate or N-methylaminopropyltriorthosilicate, or, preferably, from aminoalkyl dialkylalkoxysilane.

In some embodiments, the electron donating moiety is an aminoalkyl, and the functional moiety is derived from an aminoalkyl that is further substituted by halide or by tri-orthosilicate or, preferably, by dialkylalkoxysilane.

Other bifunctional compounds which comprise an electron donating moiety as described herein and a reactive group suitable for forming a covalent with a nanostructure as described herein, are contemplated for generating a functional moiety as described herein on the electrode's surface.

A sensing electrode as described herein in any of the respective embodiments, is also referred to interchangeably as a modified CF electrode, or a modified CF microelectrode, or amino-modified CF electrode, and diversions and variations thereof.

According to an aspect of some embodiments of the present invention there is provided a process of preparing the sensing electrode as described herein, the process comprising coupling to a carbon electrode featuring a plurality of first reactive groups on at least a portion of its surface, as described herein, a compound featuring the functional moiety and a second reactive group that forms a covalent bond with the first reactive groups.

The first and second reactive groups are selected so as to be compatible with one another in forming a covalent bond therebetween, as described herein, and the coupling is effected under conditions (e.g., chemical reagents, chemical conditions such as pH and/or physical conditions such as heat, radiation, etc.) for promoting the formation of a covalent bond between the first and second reactive groups.

The first and second reactive groups, according to any of the embodiments described herein, can be such that interact via a chemical reaction such as nucleophilic substitution reaction, addition-elimination reaction, Diels-Adler reaction, and any other reaction that results in formation of a covalent bond. Reactions for forming covalent bonds, reactive groups participating in such reactions and conditions for promoting such reactions are readily recognized by those skilled in the art.

In some embodiments, the coupling is effected at a gas phase, such that the compound featuring the functional moiety and the second reactive group is in a gaseous form. In some of these embodiments, the conditions for promoting the coupling (the formation of a covalent bond as described herein) are such that this compound is in a gaseous form. Such conditions typically include elevated temperatures (e.g., 50-150° C.) and reduced pressure, at which the vapor pressure of the compound is high. Exemplary such conditions are described in the Examples section that follows.

In some of any of the embodiments described herein, the process further comprises, prior to the coupling, generating the first reactive group, or a plurality of first reactive groups, on at least a portion of the surface of the carbon electrode.

In some of any of the embodiments described herein, the first reactive groups are generated by oxidizing the surface of a portion thereof, to thereby generate, as a non-limiting example, hydroxy group and/or aldehydes or ketones or carboxylate groups in the electrode-s surface or a portion thereof.

In some of any of the embodiments described herein, generating the first reactive groups comprises subjecting the carbon electrode to oxygen plasma treatment. Exemplary processes of surface modification of a carbon electrode and of preparing a sensing electrode as described herein is described in the Examples section that follows.

Sensing System:

In some of any of the embodiments described herein, the sensing electrode as described herein is usable for electrochemical detection of a nitro-containing compound in a sample.

In some of any of the embodiments described herein, the sensing electrode as described herein is usable for electrochemically determining a presence and/or level of a nitro-containing compound in a sample.

In some of any of the embodiments described herein, the sensing electrode as described herein is usable for determining a presence and/or level of a nitro-containing compound in a sample, upon integrating the electrode in an electrochemical cell.

In some embodiments of the present invention, there is provided an electrochemical cell which comprises a sensing electrode as described herein in any of the respective embodiments and any combination thereof. The sensing electrode functions, and is also referred to herein, as a working electrode.

In some embodiments of the present invention, there is provided a sensing system which comprises a sensing electrode as described herein in any of the respective embodiments and any combination thereof. Such a sensing system is also referred to as a sensor.

In some embodiments of the present invention, there is provided a sensing system which comprises an electrochemical cell as described herein in any of the respective embodiments and any combination thereof.

The following describes some embodiments of an electrochemical cell of the invention.

In some embodiments, the sensing electrode is electrically connectable to a power source, and the cell is configured such that when it is operated, at least a portion thereof, i.e., a portion thereof that have functional moieties as described herein covalently attached thereto, contacts the analyte (a nitro-containing compound or a sample containing same).

In some embodiments of the present invention, the electrochemical cell further comprises a reference electrode. Any commercially available or customarily designed reference electrode is contemplated. In some embodiments, the reference electrode is an aqueous reference electrode. Exemplary usable reference electrodes include, but are not limited to, Silver/Silver Chloride electrode (e.g., Ag/AgCl/Saturated KCl electrode such as marketed by Metrohm), a Standard calomel (e.g., saturated calomel) electrode (SCE), a Standard hydrogen electrode (SHE), a Normal hydrogen electrode (NHE), a Reversible hydrogen electrode (RHE), a Copper-copper(II) sulfate electrode (CSE); a pH-electrode; a Palladium-hydrogen electrode, a Dynamic hydrogen electrode (DHE), and a Mercury-mercurous sulfate electrode (MSE).

The reference electrode is also electrically connectable to a power source, and the cell is configured such that when it is operated, a potential difference (voltage) is applied between the sensing electrode and the reference electrode.

In some embodiments, the electrochemical cell follows a three-electrode design and further comprises an auxiliary electrode. Preferably, but not obligatory, the auxiliary electrode is a platinum electrode. Any other auxiliary electrode, commercially available or customarily designed, is contemplated. Non-limiting examples include gold electrodes, carbon electrodes and carbon/gold electrodes.

In some embodiments, the auxiliary electrode is electrically connectable to the sensing electrode.

In some of any of the embodiments described herein, the electrochemical cell further comprises a device that measures a current generated at the sensing electrode, as a result of redox reactions occurring at or next to (in the vicinity of) a surface of the sensing electrode. In some embodiments, this device (e.g., an amperometer, a picoameter) is electrically connectable to the auxiliary electrode and the sensing electrode.

A schematic presentation of an exemplary assembly of a three-electrode electrochemical cell 10 according to some embodiments of the present invention is presented in FIG. 1.

Electrochemical cell 10 comprises a sensing electrode 12 as described herein, which acts as a working electrode. Sensing electrode 12 features functional moieties 16 as described herein at least on a portion of a surface thereof, and, optionally and preferably also features surface reactive groups as described herein (not shown). When the cell is operated, the portion of the electrode that features functional moieties 16 should be in contact with the analyte, e.g., by contacting an electrolyte 18 in which the analyte is dissolved. Sensing electrode 12 is one half of electrochemical cell 10. A reference electrode 22 is the other half of cell 10. A power source 20 is electrically connectable to sensing electrode 12 and reference electrode 22 by means of electrical wires 24. Power source 20 is configured to apply voltage between sensing electrode 12 and reference electrode 22, for example, by applying potential to one of the electrodes. Optionally, but not obligatory, cell 10 further comprises an auxiliary electrode 26, and a current measuring device 28, and device 28 is electrically connectable to sensing electrode 12 and auxiliary electrode 26.

For an electrochemical cell (e.g., cell 10) to operate, at least the sensing electrode (electrode 12) should be in contact with an electrolyte shown in FIG. 1 as an electrolyte 18. The electrochemical cell (e.g., cell 10) can comprise an electrolyte (e.g., electrolyte 18, as exemplified in FIG. 1), or can comprise means (e.g., an inlet port; not shown in FIG. 1), for introducing the electrolyte to the cell, so as to contact at least the sensing electrode (e.g., sensing electrode 12).

An electrochemical cell according to the present embodiments can follow any of the designs known in the art, and can include one or more sensing electrode(s), and one or more of a reference electrode(s) and/or an auxiliary electrode(s). Exemplary designs include, without limitation, rotating disk-ring electrodes, ultramicro-electrodes, or screen printed electrodes.

The configuration of the components of electrochemical cell 10 as presented in FIG. 1 are for illustrative purpose only and are not to be regarded as limiting in any way.

Electrochemical cell 10 can be, for example, in a form of a covered glass (or other inert material like Teflon or quartz) beaker, containing the sample solution in which the three electrodes are dipped. In some embodiments, electrochemical cell 10 is a micro cell or a thin layer cell.

Electrochemical cell 10 may further comprise means for mixing/stirring a sample with electrolyte 18 (not shown in FIG. 1).

Electrochemical cell 10 may further comprise means for monitoring and/or controlling the temperature inside the cell (not shown in FIG. 1).

As used herein and in the art, an electrolyte is an electrically conducting material or medium. An electrolyte can be solid or fluid, and can be used per se or when dissolved in a polar solvent, such as water. When dissolved is a solvent, it is referred to as an electrolyte solution. In the context of electrochemical cells, an electrolyte is also referred to as a background solution.

Herein throughout, the term "electrolyte" also encompasses an "electrolyte solution".

In an electrochemical cell as described herein (e.g., cell 10, FIG. 1), at least the sensing electrode (e.g., sensing electrode 12) contacts the electrolyte (e.g., electrolyte 18) when the cell is operated. In some embodiments, all electrodes contact an electrolyte (e.g., electrolyte 18) when the cell is operated. In some embodiments, all electrodes contact the same electrolyte, as exemplified in FIG. 1, and in some embodiments, one or more of the electrodes contact an electrolyte different from the electrolyte in contact with the sensing electrode, and a membrane is interposed between the different electrolytes.

In some of any of the embodiments described herein, the electrolyte solution (e.g., electrolyte solution 18, FIG. 1), features a pH lower than 8, or a pH lower than 7, or a pH lower than 6, or lower than 5 or lower. In some embodiments, the electrolyte solution features a pH in a range of from 1 to 7, or from 1 to 6.5, or from 3 to 7, or from 3 to 6.5, or from 4 to 6.5, or from 3 to 4, including any intermediate values and subranges therebetween. In some embodiments the electrolyte solution features pH of about 4. As demonstrated in the Examples section that follows, an acidic pH as described herein provides for optimal sensing in terms of sensitivity and a linear correlation between the nitro-containing compound's concentration and the detected current. In some embodiments the electrolyte solution features pH of about 6.5. As demonstrated in the Examples section that follows, such a pH provides an efficient sensing while avoiding any possible overlap with signals generated by hydrolysis of an aqueous electrolyte solution.

In some of any of the embodiments described herein, the electrolyte solution (e.g., electrolyte 18) is or comprises an aqueous solution.

In some of any of the embodiments described herein, the electrolyte solution (e.g., electrolyte 18) comprises a mixture of an aqueous solution and an organic solvent.

Exemplary aqueous solutions include buffer solutions, for example, phthalate buffer solutions, phosphate buffer solutions or any other buffer solution that provides the desired pH value, as described herein. Buffer solutions that provide pH values as described herein are well known to those skilled in the art.

Exemplary organic solvents include, water-miscible solvents, preferably polar and/or aprotic solvents, and, further preferably, solvents in which a nitro-containing compound is dissolvable and/or in which an organic quaternary ammonium salt of choice, as described herein, is dissolvable.

Suitable organic solvents are preferably further characterized as capable of inhibiting or reducing electrolysis of water and/or of broadening the electrochemical window of water, for example, up to −2 Volts.

Suitable organic solvents are preferably further characterized as being chemically compatible with (e.g., chemically inert to) the electrochemical cell or system as described herein. In some embodiments, the organic solvent is characterized as being chemically compatible with plastic and/or any other polymeric materials typically used for constructing electrochemical cells or systems.

An exemplary solvent is acetonitrile, although other solvents, such as, for example, dimethyl formamide, dimethylsulfoxide, propylene carbonate, ethanol, methanol, and any mixture thereof, are contemplated. Another exemplary solvent is ethanol.

A volume ratio between an aqueous solution and an organic solvent can range, for example, from 10:1 to 1:1, or from 5:1 to 1:1, or from 3:1 to 1:1, or from 5:1 to 3:1, including any intermediate value and subranges therebetween. For example, an electrolyte solution can comprise 90 vol. % aqueous solution and 10 vol. % organic solvent, or 80 vol. % aqueous solution and 20 vol. % organic solvent, 75 vol. % aqueous solution and 25 vol. % organic solvent, or 70 vol. % aqueous solution and 30 vol. % organic solvent, or 65 vol. % aqueous solution and 35 vol. % organic solvent, or 60 vol. % aqueous solution and 40 vol. % organic solvent, or 55 vol. % aqueous solution and 45 vol. % organic solvent, or 50 vol. % aqueous solution and 50 vol. % organic solvent. In some embodiments, an electrolyte solution comprises 70 vol. % aqueous solution and 30 vol. % organic solvent.

In some of any of the embodiments described herein, an electrolyte solution (e.g., electrolyte solution 18, FIG. 1), comprises a soluble salt (e.g., a water-soluble salt, or a salt soluble in the solvent mixture making up the electrolyte solution). Any soluble salt commonly used in electrolyte solution for increasing the ionic strength is contemplated, typically an inorganic salt, with potassium chloride being a non-limiting exemplary salt. A concentration of the salt typically determines, at least in part, the ionic strength of the electrolyte solution and can range from, for example, 0.1M to 1M, or from 0.1M to 0.5M, including any intermediate value and subranges therebetween. In some embodiments, a concentration of the salt is 0.25M.

In some of any of the embodiments described herein, the electrolyte solution comprises, preferably in addition to an inorganic salt, a quaternary ammonium salt, preferably, an organic quaternary ammonium salt.

An organic quaternary ammonium salt can be represented by the Formula:

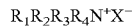

wherein: $R_1$, $R_2$, $R_3$ and $R_4$ is each independently an alkyl, cycloalkyl or aryl, or alternatively, two or more form together a heterocylic (heteroalicyclic or heteroaryl) ring; and X is an anion such as halide (e.g., chloride, bormide, iodide), perchlorate, borate, and any other acceptable anion.

The selection of the anion can be made such that it is inert to the electrochemical window of water, that is, the anion is preferably such that features a standard electrode potential higher than hydroxide.

In some embodiments, the anion is other than halide.

In some embodiments, $R_1$, $R_2$, $R_3$ and $R_4$ is each independently an alkyl, and in some embodiments, each is independently an alkyl of from 1 to 4 carbon atoms.

In some of any of the embodiments described herein, the organic quaternary ammonium salt is soluble in the electrolyte solution as described herein in any of the respective embodiments.

Exemplary organic quaternary ammonium salts that are usable in the context of the present embodiments include commonly used phase transfer catalysts.

In some of any of the embodiments described herein, a concentration of the quaternary ammonium salt is lower than 0.5 M, or lower than 0.2M, or lower than 0.1 M. In some embodiments, a concentration of the quaternary ammonium salt ranges from 1 to 10 mM, including any intermediate values and subranges therebetween. In some embodiments, a concentration of the quaternary ammonium salt is 5 nM.

In some of any of the embodiments described herein, the quaternary ammonium salt is such that assists in providing a sharp peak of the oxygen reduction and/or of the nitro-containing compound reduction.

Non-limiting examples of a quaternary ammonium salt is tetrabutylammonium iodide and tetrabutylammonium perchlorate, although other quaternary ammonium compounds are contemplated.

Exemplary electrolyte solutions according to the present embodiments are described in the Examples section that follows. As exemplified therein, an electrolyte solution comprising a mixture of an aqueous buffer solution featuring a pH lower than 7 as described herein, an organic solvent, an inorganic salt and an organic quaternary ammonium salt at a low concentration, when used in combination with a sensing electrode as described herein, enables to reduce and even diminish a masking effect resulting from the presence dissolved oxygen (e.g., by reducing an overpotential of oxygen reduction and/or increasing the gap between the potential at which reduction of a nitro-containing compound and of oxygen occurs) and allows performing electrochemical detection while circumventing the need to deaearate (e.g., evacuate oxygen from) the cell or system.

In some of any of the embodiments described herein, an electrochemical cell and/or a sensing system comprising same, as described herein, is operable when a concentration of oxygen in the electrolyte is at least 1 ppm, or at least 10 ppm, or at least 20 ppm, or at least 30 ppm, or higher.

In some of any of the embodiments described herein, electrochemical detection of a nitro-containing compound is performed using an electrochemical cell and/or a sensing system comprising same, as described herein, when a concentration of oxygen in the electrolyte is at least 1 ppm, or at least 10 ppm, or at least 20 ppm, or at least 30 ppm, or higher.

In some of any of the embodiments described herein, an electrochemical cell and/or a sensing system comprising same, as described herein, is operable when a concentration of oxygen in the electrolyte is higher than a concentration of a nitro-containing compound in the electrolyte by at least 10-folds, or at least 20 folds, or at least 30-folds, or at least 50-folds or at least 100-folds, or at least 1000-folds or at least 5000-folds, and even higher.

In some of any of the embodiments described herein, electrochemical detection of a nitro-containing compound is performed using an electrochemical cell and/or a sensing system comprising same, as described herein, when a concentration of oxygen in the electrolyte is higher than a concentration of a nitro-containing compound in the electrolyte by at least 10-folds, or at least 20 folds, or at least 30-folds, or at least 50-folds or at least 100-folds, or at least 1000-folds or at least 5000-folds, and even higher.

In some of any of the embodiments described herein, the sensing system and/or the electrochemical cell described herein is/are devoid of means for deaerating the system or cell prior to contacting the sensing electrode with a sample. Such means typically include physical means for introducing an inert gas, such as argon gas or nitrogen gas, to the cell, and optionally a source of the inert gas connectable to the means; and/or means for chemically removing oxygen, for example, zinc or sodium sulfate.

In some of any of the embodiments described herein, the sensing system and/or the electrochemical cell described herein is/are devoid of means for bubbling an inert gas in the electrolyte solution and/or means for connecting the cell and/or the system to a source of an inert gas.

In some of any of the embodiments described herein, the sensing system and/or the electrochemical cell described herein is/are devoid of zinc, sodium sulfate, or any other chemical reagents that can react with oxygen; and/or is/are devoid of means of contacting oxygen with such chemical reagents.

In some of any of the embodiments described herein, a system as described herein further comprises means for introducing a sample to the electrochemical cell. The sample should be introduced to the cell such that it contacts the sensing electrode.

In some embodiments, the sensing system comprises means for introducing a sample to the electrochemical cell such that it contacts the sensing electrode.

In some embodiments, the sensing system comprises means for introducing a sample to the electrochemical cell such that it is mixed with or dissolved in the electrolyte solution.

In some embodiments, a sample is introduced to the electrochemical cell by means of an inlet port, referred to herein also as a sample inlet. In some embodiments, the inlet port is configured for introducing a gaseous sample to the cell. In some embodiments, the inlet port is configured for introducing a liquid sample to the cell. In some embodiments, a fluid (gaseous and/or liquid) sample is bubbled into the electrolyte solution and the inlet port is configured for effecting such bubbling.

In some of any of the embodiments described herein, the system is devoid of a sample inlet. This is enabled by the carbon fiber electrode, which is gas permeable and hence gas samples can enter the electrochemical cell therethrough.

In some of any of the embodiments described herein, the means for introducing a sample to the electrochemical cell include a pump or a pumping device. An exemplary pump is an air pump, in cases where the sample is in a gaseous form. The pump or the pumping device can be in contact with the CF microelectrode of the present embodiments, such that the pumped sample permeates through the electrode and is thus introduced to the cell or system. Alternatively, the pump or pumping device are in contact with the electrolyte, such that the pumped sample contacts or is mixed with the electrolyte.

In some embodiments, a system as described herein further comprises a gas outlet.

In some of any of the embodiments described herein, a sensing system as described herein is operable by assembling at least a sensing electrode as described herein and an electrolyte, and electric means for electrically connecting the sensing electrode to a power source; introducing a sample into the electrochemical cell, by means that allow the sample to contact (e.g., dissolve in) the electrolyte, as described herein; applying a potential to the sensing electrode, by means of a power source as described herein; and measuring an electrochemical signal that is indicative of an electrochemical reaction in which the nitro-containing compound participates.

In some of any of the embodiments described herein, the electrochemical signal is an electrical current generated at the sensing electrode is response to said potential, and measuring the signal is effected by means of an electrical current measuring device. The measured current is indicative of a presence and/or level (e.g., amount, concentration) of a nitro-containing compound in the sample.

In some of any of the embodiments described herein, the electrochemical cell comprises a reference electrode and applying a potential is effected by applying voltage between the sensing electrode and the reference electrode.

The power source is configured to apply potential to the sensing electrode according to any known voltammetry method, as described in further detail hereinafter, in embodiments related to a sensing method.

In some embodiments, the power source is configured to apply a varying potential to the sensing electrode, and in some embodiments, the power source is configured to apply a linearly varying potential (as in linear sweep voltammetry); a staircase varying potential; a squarewave varying potential; or a pulse varying potential (normal pulse or differential pulse), as described in further detail hereinbelow.

In some embodiments, the power source is configured to apply differential pulse potential.

In some embodiments, the system is configured to determine a current generated in response to the varying potential, and in some embodiments, the system is configured for determining a change in the current generated at the sensing electrode, in response to the varying potential.

In some of any of the embodiments described herein, the system is configured to determine an electric current or a change in an electric current, compared to an electric current or a change in the electric current generated at the sensing electrode, in response to the varying potential, when a sample is not introduced to the electrochemical cell. Such data is also referred to herein as "background current" and in some embodiments, the system is configured to subtract the background current from the determined current or change in current.

In some embodiments, the system is operable in a differential pulse voltammetry mode and is configured to determine a change in an electrical current that is relative to a change in the potential (a derivative of the applied potential) in response to a change in the potential, as is known in the art.

Generally, but not necessarily, the system is configured for providing a voltammogram that presents values that are in line with the voltammetry methodology used.

Determination of a change in the electrical current, according to any of the respective embodiments, can be performed by means of a device which is configured to process the received signals (e.g., the mode of the applied varying potential and corresponding generated current data) so as to provide a value or a set of values as desired (e.g., a change in electrical current relative to a derivative of the applied potential, or any other voltammogram). Such a device is also referred to herein as a signal processor.

In some embodiments, the signal processor is a data processor such as a computer configured for receiving and analyzing the signals. The signal processor extracts, from each generated signal or set of signals, a parameter (e.g., a voltammogram) that is indicative of an electrochemical reaction of a nitro-containing compound, and hence of a presence and/or level of the nitro-containing compound.

In some embodiments of the invention the signal processor is configured to construct a fingerprint of a nitro-containing compound, for example, a voltammogram obtained upon contacting an electrolyte with the nitro-containing compound and applying a certain mode of a varying potential (e.g., a differential pulse potential).

In some embodiments of the invention the signal processor is configured to construct a database of fingerprints of a plurality of nitro-containing compounds, for example, a database of voltammograms obtained upon contacting an electrolyte with a nitro-containing compound and applying a certain mode of a varying potential (e.g., a differential pulse potential). The database can include several voltammograms for each nitro-containing compound, each for a different mode and/or range and/or rate of application of the varying potential, and/or each for a different electrolyte.

In some embodiments of the invention the signal processor is configured to search a database of fingerprints of a plurality of nitro-containing compounds, for example, a database of voltammograms as described herein, for a fingerprint that matches a received fingerprint, and to identify accordingly the nitro-containing compound.

In some of any of the embodiments of the invention the signal processor is configured to determine a level of an identified nitro-containing compound in a sample, by accessing and/or processing relevant data. Such data can include, for example, a calibration curve, e.g., of voltgammograms, or of specific values obtained in voltammetry measurements (e.g., a reduction peak), obtained for varying concentrations of the identified nitro-containing compound, and stored on a computer readable medium. For example, the signal processor may access the calibration curve, search for a value (e.g., a reduction peak) that matches the value obtained upon operating the system, and identify a concentration of the identified nitro-containing compound that matches this value. Alternatively, or in addition, the data include a lookup table stored on a computer readable medium, which can be searched for values that match the measured value and are indicative of a level of an identified nitro-containing compound. Further alternatively, or in addition, the data include a predetermined relationship between the measured value and a level of the identified nitro-containing compound. For example, if such a predetermined relationship comprises a linear relationship, the signal processor can determine the level of an identified nitro-containing compound by means of extrapolation, based on the pre-determined relationship.

In some of any of the embodiments described herein, the sensing system as described herein further comprises an additional sensing electrode, which is configured to generate an electrical signal upon contacting a compound other than a nitro-containing compound. In some of these embodiments, the additional sensing electrode forms a part of an additional electrochemical cell. Such a system is configured such that a sample is introduced therein and contacts both sensing electrodes. The generated electrical signals are thus indicative of the presence/absence and amount (if present) of both the nitro-containing compound and the other compound.

In some embodiments, such a sensing system further comprises a signal processor as described herein which is configured to identify the nitro-containing compound, as described herein, and to identify the other compound, and, optionally, to further determine a level of each identified compound in a sample.

In some embodiments, the additional sensing electrode is a carbon electrode which is modified so as to detect the additional compound.

In some embodiments, the additional sensing electrode is configured to detect explosives other than nitro-containing explosives, for example, peroxide-containing compounds.

In some of any of the embodiments described herein, a sensing system as described herein comprises a plurality (e.g., two, three or more) of modified CF microelectrodes as described herein, wherein at least one portion of the CF microelectrodes is modified so as to feature a first functional moiety and at least another portion of the CF microelectrodes features a second functional moiety which is different from the first functional moiety, whereby both functional moieties interact with a nitro-containing material as described herein in any of the respective embodiments.

In some of these embodiments the sensing system comprises three, four or more portions of CF microelectrodes, each featuring a different functional moiety that interacts with a nitro-containing compound as described herein.

In some of any of these embodiments, the sensing system comprises a plurality of electrochemical cells or a plurality of electrochemical half cells, each being individually connectable to a power source, and, optionally, each being individually connectable to a device for measuring the electrochemical parameter as described herein.

In some of any of these embodiments, each of the measuring devices can independently be connected to a signal processor, or, alternatively, all measuring devices are connected to the same signal processor.

Such a sensing system can generate for different peroxide-containing compounds different defined fingerprints, and allows using, for example, a dedicated database, for the identification of the nitro-containing compound based on such fingerprints database, according to the guidelines provided herein.

Electrochemical Detection:

According to an aspect of some embodiments of the present invention there is provided a method of detecting a nitro-containing compound in a sample, while utilizing a sensing electrode as described herein in any of the respective embodiments.

In some embodiments, a method as described herein utilizes a sensing electrode and an electrolyte solution, as described herein in any of the respective embodiments.

In some embodiments, a method as described herein utilizes a sensing system, as described herein in any of the respective embodiments.

In some embodiments, a method as described herein is devoid of a step of deaerating the electrolyte or a cell or a system comprising the electrolyte prior to performing the detection. In some embodiments, the method is devoid of introducing an inert gas to the cell, for example, is devoid of bubbling an insert gas in the electrolyte solution.

In some embodiments, a method as described herein is performed when a concentration of dissolved oxygen in the electrolyte at the time of detection is at least 1 ppm, and/or is higher by at least one order of magnitude (or two or three or more orders of magnitude) than a concentration of the nitro-containing compound in the electrolyte, as described herein.

Herein throughout, the terms "detection", "detecting" and grammatical diversions thereof, and the terms "sensing", are used interchangeably, and refer to determining a presence and/or level of a nitro-containing compound.

In some of embodiments, the method as described herein is a method of electrochemical detection of nitro-containing compounds.

In some embodiments, the method is effected by contacting a sensing electrode as described herein in any of the respective embodiments with a sample, and applying a potential to the sensing electrode.

In some embodiments, the method is further effected by measuring an electrochemical parameter upon applying the potential to the sensing electrode, and in some embodiments, the electrochemical parameter is an electrical current generated at the sensing electrode or a change in the electrical current at the sensing electrode. A presence and/or level of the electrochemical parameter is indicative of a presence and/or level of the nitro-containing compound.

In some embodiments, the sensing electrode forms a part of an electrochemical cell as described herein in any of the respective embodiments, or a part of a sensing system as described herein in any of the respective parameters, and contacting the sensing electrode with the sample is effected by introducing the sample to the electrochemical cell or system, as described herein.

The sample can be introduced to the cell or system by means of a sample inlet, or by means of a pump, as described herein.

In some embodiments, contacting the sensing electrode with the sample is effected by introducing the sample to an electrolyte solution, preferably an electrolyte solution as described here in any of the respective embodiments.

In some embodiments, contacting the sensing electrode with the sample is effected by contacting a gas permeable sensing electrode with a gaseous sample, for example, by means of an air pump as described herein. In some embodiments, the electrolyte and the sensing electrode form a part of an electrochemical cell or sensing system as described herein, and in some of these embodiments, the sensing electrode contacts the electrolyte.

In some embodiments, the method further comprises contacting the sensing electrode with the electrolyte, either prior to or subsequent to introducing the sample to the electrolyte.

In some embodiments, applying a potential to the sensing electrode is performed immediately after contacting the sensing electrode with the sample.

In some embodiments, applying a potential to the sensing electrode is performed immediately after contacting the sensing electrode with an electrolyte to which the sample was introduced.

In some embodiments, applying the potential is performed while a concentration of dissolved oxygen in the electrolyte is at least 1 ppm, as described herein.

In some embodiments, the sensing electrode forms a part of an electrochemical cell as described herein and applying the potential is performed by applying a voltage between the sensing electrode and a reference electrode.

In some embodiments the potential is a varying potential.

In some embodiments, measuring an electrochemical parameter is by a voltammetry experiments. Voltammetry measurements are also referred to in the art as potentiostatic electrochemical analyses.

As known in the art, voltammetry experiments are conducted for obtaining information (e.g., presence, identity and/or level) of an analyte by measuring a generated current or a change in the current in response to application of a varying potential.

In order to obtain a quantitative measurement of an analyte (e.g., a nitro-containing compound as described herein) by potentiostatic electrochemical analysis, the amount of electrons used for the reduction/oxidation of the analyte should be monitored. In thermodynamic equilibrium the ratio of the redox-reactive species at the surface of the electrode can be obtained by Nernst equation:

$$E = E^0 + \frac{2.3RT}{nF}\log\left(\frac{C_O}{C_R}\right)$$

Where $C_O$ is the concentration of the oxidized form, and $C_R$ is the concentration of the reduced form, E is electrode potential, $E^0$ is standard electrode potential, R is the gas constant $\left(8.314 \frac{J}{Kmol}\right)$, T is the temperature (Kelvin scale), n is the number of electrons participate in the redox reaction and F is the Faraday constant (96,487 coulombs).

The entire measured current is composed of Faradic currents and non-Faradic charging background current. The Faradic current obtained by the electrochemical reaction behaves according to Faraday's low, which means that 1 mole of redox active substance will involve a charge change of n×96,487 coulombs.

The information retrieved by voltammetry experiments, in its simplest form, is obtained as a voltammogram of I=f(E).

A voltammogram is a current versus potential curve used to describe the analyte's electrochemical reaction performed at the electrode as a result of the applied potential, and its derived current. It may have a complicated multi-stepped shape according to the complexity of the chemical reaction.

In some embodiments, and depending on the type of voltammetry used, the potential is varied continuously or stepwise or in pulses.

In some embodiments, the potential or varying potential applied to the sensing electrode is such that allows reduction or at least partial reduction of one or more nitro groups in a nitro-containing compound, typically to a corresponding amine group or groups.

Exemplary potentials that can be applied to a sensing electrode as described herein range from 0 to about −2 Volts.

Voltammetry experiments can be categorized as linear sweep voltammetry and cyclic voltammetry.

Cyclic voltammetry is the process of electrochemical analysis in which the applied voltage is of a multi or mono-triangular shape. The resulting plot of current versus linear triangular potential scan of the working electrode is called cyclic voltammogram, while the plot of current versus linear potential scan of the working electrode is called linear sweep voltammogram. Cyclic voltammetry is usually the preliminary process used to determine the reduction potential of an analyte, the media's influence and the thermodynamics, as well as kinetics, of the electrochemical reaction.

In response to the triangular shaped potential, the measured current of the electrochemical cell that contained initially only the oxidized species, gradually increases up to a sharp peak at $E_{p[red]}$, followed by current decrease when most species adjacent to the electrode surface are reduced. When reversing the potential's direction, a gradual increase of current at the opposite direction ends in a sharp peak at $E_{p[ox]}$, where the chemical reaction proceeds to the opposite direction towards the oxidized form. When most species adjacent to the electrode surface are oxidized, the current decreases until the point of potential reverses, and so on.

Since an electrochemical reaction is located at the interface between the working electrode and the electrolyte solution, the reduced and oxidized species causing the sharp peaks of the voltammogram are concentrated to a narrow diffusive layer adjacent to the electrode. As a result, the shape of the curve's peak depends on the rate of diffusion. The peak's incline correlative to the concentration of electroactive particles on the electrode's surface, while the sharp decline depends solely on time, and results from the absence of electroactive particles near the surface due to limited diffusion.

In order to increase the sensitivity of voltammetric measurements, the share of the Faradic currents in the obtained voltammogram can be increased on the expense of the nonfaradaic background current. Such alterations are enabled by applying a series of short duration potential steps (each last for several milliseconds) in a technique termed "pulse voltammetry". At the end of each potential step, two different current decay rates are obtained: sharp exponential decay to a negligible level is characteristic to the charging current, while slower decay is typical to the Faradic current. By recording the current's signal at the later regime, more of the signal is attributed to the Faradic current, while the contribution of the charging current is negligible. The differential pulse voltammogram is obtained from the subtraction of the pre-pulse current from the current that is obtained after the pulse is switched off, plotted against the applied potential. The corresponding sensitivity is thereby increased. The differential pulse voltammetry techniques vary by the shape of the applied potential waveform, and the current sampling technique.

Alongside increased sensitivity, differential pulse voltammetry allow the detection of two different analytes with similar redox potentials, by analysis of the peak's width according to the number of electrons that participate in their redox reaction. Exemplary values used for differential voltammetry measurements are 25-50 mV for current pulse amplitudes and 5 mV/second for the scan rate, while steeper amplitudes and faster scan rates are also contemplated.

In some of any of the embodiments described herein, the potential is a differential pulse varying potential.

In some of any of the embodiments described herein, the range of a varying potential ranges from −2 to +1 Volts, including any intermediate subranges therebetween.

In some of any of the embodiments described herein, an electrochemical parameter measured in a method as described herein is a change in electrical current relative to a derivative of the applied potential, although any other voltammogram is contemplated.

In some of any of the embodiments described herein, the measured electrochemical parameter is processed by a signal processor, as described herein in any of the respective embodiments, to thereby determine a presence, a composition and/or a level of one or more nitro-containing compounds in the sample.

In some of any of the embodiments described herein, a time ranging from introducing a sample so as to contact the sensing electrode to measuring the electrochemical parameter is less than 2 minutes, or less than 1 minute, or even less than 30 seconds, or less than 20 seconds, or less.

In some of any of the embodiments described herein, the method further comprises, prior to contacting the sample with the sensing electrode (e.g., prior to introducing the sample to the electrochemical cell), applying the potential, and measuring the electrochemical parameter, to thereby measure a background signal. In some embodiments, upon measuring the electrochemical parameter resulting from contacting the sensing system and the sample, the background signal is subtracted from the measured electrochemical parameter.

In some of any of the embodiments described herein, the method further comprises, subsequent to measuring the electrochemical parameter, applying an opposite potential to the sensing electrode, to thereby regenerate the electrode.

In some of any of the embodiments described herein, a method as described herein is effected in an oxygen-containing environment, as described herein.

Sample:

As used herein, the phrase "nitro-containing compound" encompasses compounds which include one or more nitro groups, attached to, for example, saturated or unsaturated, linear or cyclic, hydrocarbon backbone.

A nitro-containing compound can therefore be comprised of an aliphatic or alicyclic or aromatic hydrocarbon moiety, substituted by one or more nitro groups. The hydrocarbon moiety can optionally be interrupted by one or more heteroatoms such as nitrogen, oxygen, sulfur, phosphor, silicon, boron. The hydrocarbon moiety can optionally be further substituted by other substituents, as described herein.

In some of any of the embodiments described herein, the nitro-containing compound comprises an aromatic moiety (e.g., an aryl) substituted by one or more nitro groups.

In some embodiments, the nitro-containing compound is an explosive.

As used herein, the term "explosive" encompasses an explosive material, an explosive residue (e.g., a substance obtained upon explosion) and a material associated with an explosive material (e.g., a starting material for preparing an explosive material).

Nitro-containing explosives include, without limitation, nitroaromatic-based explosives, nitroamine-based explosives, nitrate ester-based explosives, and inorganic nitrate-based explosives.

Exemplary nitro-containing compounds which can be detected by utilizing the methods, devices and systems described herein include, but are not limited to, 2-nitrotoluene; 3-nitrotoluene; 4-nitrotoluene; 2,4,6-trinitrotoluene (TNT); 2,4-dinitrotoluene; 3,4-dinitrotoluene; 2,6-dinitrotoluene; ethylene glycol dinitrate (EGDN); nitroglycerine (NG); nitrocellulose; ammonium nitrate, cyclotrimethylenetrinitramine (cyclonite; RDX); pentaerythritol tetranitrate (PETN); homocyclonite (octogen; HMX); 2,4,6-Trinitrophenylmethylnitramine (Tetryl); picric acid; 1,2,3-propanetrial trinitrate and any mixture and/or formulation thereof, including, for example, 1,2,3-propanetrial trinitrate Formulations (e.g., NitroBid); C-2 (RDX, TNT, DNT and NG); C-3 (RDX, TNT, DNT, Tetryl and NG); C-4 (RDX and PETN), Semtex (RDX and PETN); Detasheet (RDX and PETN); Dynamites (EDGN and NG); Pentolite (PETN+TNT); PTX-1 (RDX, TNT and Tetryl); PTX-2 (RDX, TNT and PETN); and Tetryol (TNT and Tetryl).

Herein, a nitro-containing compound is also referred to interchangeably as an analyte.

The sample encompasses samples suspected as containing a nitro-containing compound, such that the system and method described herein is utilized for determining a presence and optionally a level (a concentration or an amount) of a nitro-containing compound and further optionally an identity (e.g., a chemical composition) of a nitro-containing compound. Optionally, the sample is known to contain a nitro-containing compound and the method and system described herein is utilized for determining an amount (level) and/or identity of the nitro-containing compound.

In some of any of the embodiments described herein, the sample is a fluid sample, and can be a liquid sample or a gaseous sample.

In some of any of the embodiments described herein, the sample is air.

In some of any of the embodiments described herein, the nitro-containing compound is in a fluid state (e.g., is in a liquid state or a gaseous state).

The term "fluid" is defined as a substance that tends to flow and to conform to the outline of its container. Typical fluids include liquids and gasses, but may also include free flowing solid particles.

In some of any of the embodiments described herein, the nitro-containing compound is in a gaseous state.

By "gaseous state" it is meant that at least a portion of the compound is in a form of vapors. Thus, for example, the compound can be a liquid or a solid at room temperature, yet, it is volatile to some extent, such that a portion thereof is in a gaseous state at room temperature. Alternatively, the compound can be in such a gaseous state upon heating a sample containing same.

Since, as noted herein, the method and system described herein can be utilized for detecting ultra-trace amounts of nitro-containing compounds, the portion of a compound in a gaseous state can be ultra-law, as is further detailed hereinbelow.

In some of any of the embodiments described herein, a concentration of the nitro-containing compound in the sample is lower than 1 micromolar.

In some of any of the embodiments described herein, a concentration of the nitro-containing compound in the sample ranges from 1 micromolar to 1 attomolar, or from 1 microliter to 1 nanomolar, or from 1 microliter to 1 picomolar, or from 1 micromolar to 1 femtomolar, or from 1 nanomolar to 1 picomolar, or from 1 nanomolar to 1 femtomolar, or from 1 nanomolar to 1 attomolar, or from 1 picomolar to 1 femtomolar, or from 1 picomolar to 1 attomolar, or from 1 femtomolar to attomolar.

The concentration of the nitro-containing compound encompasses a concentration of the compound's vapors in air or other gaseous samples, as well as a concentration of the compound in a liquid sample.

Accordingly, in some of any of the embodiments described herein, the method and system described herein can be utilized to detect low-volatile nitro-containing compounds, with ultra-low vapor pressure, without concentrating the sample and/or heating the sample prior to contacting it with the system.

In some of any of the embodiments described herein, a sample comprises two or more nitro-containing compounds, for example, two or more nitro-aromatic compounds, or, for example, a mixture of two or more nitro-containing explosives each of a different chemical family (e.g., a mixture of a nitro-aromatic compound, nitrate-ester compound and a nitro-amine compound). As exemplified in the Examples section that follows, a system as described herein enables detecting each nitro-containing compound, when two or more such compounds are present in a sample.

In some of any of the embodiments described herein, a sample comprises one or more nitro-containing compounds, and one or more additional compounds of interest (target compounds or analytes).

In some of any of the embodiments described herein, the sample comprises oxygen.

If the sample is a gaseous sample (e.g. air), the sample inherently comprises oxygen, and when it is dissolved in an electrolyte, dissolved oxygen is also present in the electrolyte.

If the sample is a liquid sample, for example sea water or from any other water source, it also comprises dissolved oxygen.

A sample as described herein can be analyzed using the methods and systems as described herein per se, without further processing.

It is expected that during the life of a patent maturing from this application many relevant electrodes and electrochemical cell configurations will be developed and the scope of the term electrode and electrochemical cell is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "aminoalkyl" is used herein to describe an alkyl substituted by an amine, as defined herein. In some embodiments, the amine substitutes a terminal carbon atom in the alkyl.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

The term "halide" and "halo" describes fluorine, chlorine, bromine or iodine. The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

The term "silyl" describes a —SiR'R"R'" end group or a —SiR'R"— linking group, as these phrases are defined hereinabove, whereby each of R', R" and R'" are as defined herein.

The term "siloxy" or "siloxane" or "alkoxysilane" describes a —Si(OR')R"R'" end group or a —Si(OR')R"— linking group, as these phrases are defined hereinabove, whereby each of R', R" and R'" are as defined herein.

The term "silaza" describes a —Si(NR'R")R'" end group or a —Si(NR'R")— linking group, as these phrases are defined hereinabove, whereby each of R', R" and R'" is as defined herein.

The term "silicate" or "triorthosilicate" describes a —O—Si(OR')(OR")(OR'") end group or a —O—Si(OR')(OR")— linking group, as these phrases are defined hereinabove, with R', R" and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking group, as these phrases are defined hereinabove, where R', R" and R'" are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Carbon fiber microelectrodes (also referred to as Micro-carbon-fibers electrodes):

Spectracarb™ 2050A-1050 carbon paper microelectrode, 0.18 mm thick was obtained from Engineered Fiber Technology, USA.

AvCarb® P75 carbon paper microelectrode, 0.245 mm thick was obtained from AvCarb material solutions.

Freudenberg H23 carbon paper microelectrode, 0.210 mm thick was obtained from Freudenberg FCCT, Germany.

Sigracet 39 AA carbon paper microelectrode, about 0.280 mm thick, was obtained from SGL carbon.

ELAT—Hydrophilic Plain Cloth® carbon fabric microelectrode, 0.406 mm thick, was obtained from Fuel Cell Store.

Plain Carbon Cloth—1071 HCB carbon fabric microelectrode, about 0.350 mm thick, was obtained from AvCarb material solutions Panex 30 Carbon Fiber Fabric carbon fabric microelectrode, about 0.020 mm thick, was obtained from AbCarb Material Solutions.

Electrode samples having an area of 0.35 cm$^2$ were used in all experiments, unless otherwise indicated.

Nickel foil (thickness of 0.125 mm, ≥99.9%), Tetrabutylammonium iodide (TBA-I≥98.0%, electrochemical grade), Acetonitrile (99.8%), and Ethanol (≥99.5%), were purchased from Sigma-Aldrich, Israel.

2,4,6-Trinitrotoluene (TNT, 1.000 mg/ml in acetonitrile), 1,3,5-Trinitroperhydro-1,3,5-triazine (RDX, 1.000 mg/ml in acetonitrile), [3-Nitrooxy-2,2-bis(nitrooxymethyl)propyl] nitrate (PETN, 1.000 mg/ml in acetonitrile), were purchased from AccuStandard, USA.

Parafilm PM996 was purchased from Alex Red, Israel.

All other reagents were obtained from known vendors.

Millipore Mill-Q water (deionized water, 18 mega-ohm) was used in all experiments.

Scanning electron microscope (SEM) measurements were performed using Quanta 200 FEG environmental scanning electron microscope.

X-ray Photoelectron Spectroscopy (XPS) measurements were performed in UHV ($2.5 \times 10^{-10}$ Torr base pressure) using 5600 Multi-Technique System (PHI, USA). The sample was irradiated with an Al K$_\alpha$ monochromated source (1486.6 eV) and the outcome electrons were analyzed by a Spherical Capacitor Analyzer using the slit aperture of 0.8 mm. The samples were analyzed at the surface only. They were uncharged during measurements.

A three-electrode cell (volume 3 ml) was used in all experiments, unless otherwise indicated, in which a platinum (Pt) electrode (0.4 cm$^2$) was used as the counter electrode, a silver-silver chloride (Ag—AgCl), with 3 molar potassium chloride, was used as the reference electrode with a double junction salt bridge (Metrohm), and micro-carbon-fibers (0.35 cm$^2$, 0.18 mm in diameter), or micro-carbon-fibers chemical modified electrode (0.35 cm$^2$, 0.18 mm in diameter) was used as the working electrode.

A non-modified working electrode was prepared from micro-carbon-fibers paper (0.18×20×5 mm), and nickel foil (0.2×25×5 mm) as a current collector (electrical contact); the connection and the insulation of micro-carbon-fibers with nickel contact was performed by Parafilm. The electrode with current collector was pressed with a pressure of about 2 kg/cm$^2$ for 30 seconds at room temperature. The electrode was carefully washed with ethanol, rinsed with distilled water and dried at room temperature.

Differential pulse voltammetry was performed using Autolab PGSTAT 302N, with baseline correction regime; the conditions were: modulation time=0.05 seconds, interval time=0.1 seconds, modulation amplitude=50 mV.

Linear sweep voltammetry were performed using Autolab PGSTAT 302N, at a scan rate of 0.1 Volt/second, unless otherwise indicated.

Example 1

Micro-Carbon-Fibers Electrode Chemical Modification and Characterization
Micro-Carbon-Fibers Electrode Chemical Modification All the equipment utilized in the modification procedures was washed with isopropanol, dried under nitrogen stream and subjected to plasma treatment at 100 W for 10 minutes.

Generally, prior to surface modification, the carbon microelectrode is immersed in ethanol for 5 minutes and washed with deionized water. Thereafter, the carbon microelectrode's surface is activated by 10 minutes exposure to 1% potassium hydroxide (weight percent in deionized water) followed by gentle wash with deionized water.

The micro-carbon-fiber electrode is subjected to $O_2$ plasma treatment at 30-60 Watts for 3-10 minutes at 0.2-0.4 Torr.

An exemplary modification of the carbon microelectrode with amino-silane mono-layer in solution phase was performed using a previously published amino-silane modification on oxidized organic surface [Dixit et al. *Nat Protoc* 6, 439-445, (2011)], and as exemplified in FIG. 2A, as follows:

Once the electrode's surface was pre-treated (e.g., oxidized), it was treated with 3-aminopropyldimethylethoxysilane (APDMES) or another amino-siloxane derivative for further silane-based modification. The micro-carbon-fibers electrode was left to react with 3-aminopropyldimethylethoxysilane for 2 hours at 80° C. in a glass sealed reactor.

Another exemplary modification was performed in gas phase using a device as depicted ion FIG. 2B. Gas phase modification is usable for large scale production of multiple modified carbon microelectrodes.

The carbon microelectrode and a vial containing the amino-siloxane derivative were placed in a device as depicted in FIG. 2B, the device was put in an oven heated to 100° C. Vacuum was generated in the oven and the device was maintained under these conditions for 4 hours. The oven was then subjected to steam cleansing, the vial containing the amino-siloxane derivative was removed and the device was put back in the heated oven and maintained therein at reduced pressure and 100° C. for additional 3 hours. After steam cleansing, the device was removed from the oven and the electrodes were removed from the device and kept in closed vessels until used.

In an alternative procedure, the pre-treated carbon microelectrode was left to react with the vapors of the amine-siloxane for 16 hours at 85° C. in a vacuum (−0.1 MPa) oven (vacuum drying oven, BIOBASE®).

All modified electrodes, once obtained, were washed with isopropanol and dried with N2 stream.

Scanning Electron Microscope and X-Ray Photoelectron Spectroscopy Analysis of Chemically Modified Micro-Carbon-Fibers Electrode:

By pre-treating (e.g., oxidizing) and thereafter modifying the carbon microelectrode (carbon paper or carbon fiber microelectrode), long term covalent binding of amino groups mono-layer to the electrode was obtained, as depicted in the schematic representation of chemical modification of an exemplary carbon paper electrode (Spectracarb™ 2050A-1050) by APDMES in FIG. 2A (left).

Further in FIG. 2A, scanning electron microscope (secondary electrons) image and X-ray photoelectron spectroscopy atomic concentrations for carbon (C), oxygen (O) nitrogen (N) and silicon (Si) analysis before (upper images) and after (lower images) modification of the electrode are presented.

According to the scanning electron microscope images, the micro-carbon-fibers electrode (before modification) is composed of rough fibers with few microns width, which contributed to the active surface area of the electrode.

The X-ray photoelectron spectroscopy analyses show the atomic concentration of carbon (C), oxygen (O), nitrogen (N) and silicon (Si) on the micro-carbon-fibers electrode surface before and after the amino moiety modification. The rise in the atomic concentration of oxygen indicates the oxidation of the micro-carbon-fibers electrode surface after the modification. The rise in the atomic concentration of nitrogen and silicon, which have the same values of the atomic concentration, indicates the successful chemical modification of the micro-carbon-fibers surface with 3-aminopropyldimethylethoxysilane.

The advantage of the described modification method is the stability of the amine monolayer. The observed lifetime of the electrode was longer than one month when stored in dry air at room temperature (data not shown).

Example 2

Oxygen Reduction by Chemically Modified Micro-Carbon-Fiber Electrodes

The electrochemical reduction of nitro-based explosives includes at least 3-4 stages, from nitro, nitroso and hydroxilamine as intermediate products to amines [See, for example, Chua et al. *J Phys Chem C* 116, 4243-4251, (2012)]. Reduction of nitro compounds to amines involves transfer of not only electrons, but also protons. A background solution with low pH has therefore been used in experiments testing its performance.

Preliminary experiments showed that the optimal mix of potassium chloride, acetonitrile and low concentration of a quaternary ammonium salt in aqueous buffer phthalate pH 4.0, have sufficiently improved the oxygen peak's shape, to form two separate electrochemical windows for nitro-aromatic, nitrate-ester and nitro-amine detection. A detailed description of assays conducted for determining an optimal pH of the electrolyte (background) solution is provided in Example 4 hereinbelow.

Differential pulse voltammetry was performed as described hereinabove, using Spectracarb™ 2050A-1050, non-modified, or modified by APDMES (as depicted in FIG. 2A) and the oxygen reduction peaks obtained were measured. The obtained differential pulse voltammetry curves are presented in FIGS. 3A-B, with the black line showing data obtained with an umodified electrode (CP), and the red line showing data obtained for amino modified electrode (CP-APDMES). The background solution contained 0.25 M Potassium chloride, 5 mM Tetrabutylammoniumiodide in aqueous buffer phthalate pH 4.0/acetonitrile mix at 7/3 volume ratio, respectively.

As shown in FIG. 3A, the differential pulse voltammetry curve of the unmodified electrode tested in the mixed background electrolyte showed that the reduction peak of oxygen was obtained at about −0.9 Volt, while the cathode window limit was at −1.3 Volt. This indicates that two electrochemical windows are available for detection: the first window was open from 0 to −0.6 Volt and the second from −1.0 Volt to −1.2 Volt.

The differential pulse voltammetry curve of the APDMES-modified electrode in the same background electrolyte showed that the reduction peak of oxygen was obtained at about −0.7 Volt and the cathode window limit was at −1.4 Volt. The two electrochemical windows available in this case for detection are therefore from 0 to −0.45 Volt and from −0.8 Volt to −1.3 Volt.

It is therefore shown that the electrochemical windows of the modified micro-carbon-fibers electrode are broader, thereby allowing the detection of both nitro-aromatic, nitrate-ester and nitro-amine explosives in sufficiently short detection time and in a single cycle.

Further, it can be seen that the chemical modification of the carbon paper microelectrode has lowered the overpotential of oxygen by about 200 mV.

Differential pulse voltammetry was also performed as described hereinabove for measuring the oxygen reduction peak obtained by the unmodified carbon paper electrode and by an electrode that was subjected to plasma treatment. The obtained differential pulse voltammetry curves are presented in FIG. 3B, with the red line showing data obtained with an unmodified electrode (untreated electrode), and the black line showing data obtained for same electrode subjected to plasma treatment (oxygen plasma treated electrode). The background solution contained 0.25 M Potassium chloride, 5 mM Tetrabutylammoniumiodide in aqueous buffer phthalate pH 4.0/acetonitrile mix at 7/3 volume ratio, respectively.

As shown in FIG. 3B, the electrochemical windows of the plasma-treated electrode are broader than those of the untreated electrode, and the over-potential of oxygen is lowered by about 200 mV.

Example 3

Detection of Nitro-Aromatic and Nitro-Amines Based Explosives in the Presence of Dissolved Oxygen The amino-modified carbon electrode prepared as described hereinabove enables to perform calibration curves and finger-printing of nitro-based explosives using differential pulse voltammetry in the presence of dissolved oxygen, as described herein.

FIGS. 4A-C present the data obtained in differential pulse voltammetry scans of TNT (FIG. 4A), RDX (FIG. 4B) and PETN (FIG. 4C), with an APDMES-modified electrode as shown in FIG. 2A and described in Example 3, as an exemplary amine-modified carbon paper microelectrode, as described herein. The background solution contained 0.25 M Potassium chloride, 5 mM Tetrabutylammoniumiodide in aqueous buffer phthalate pH 4.0/acetonitrile mix at 7/3 volume ratio, respectively.

Differential pulse voltammetry fingerprints and calibration curve for 2-Methyl-1,3,5-trinitrobenzene (TNT) was performed by sequential additions of 20 ppb of TNT, at a concentration range of 0-160 ppb. Differential pulse voltammetry fingerprints and calibration curve for 1,3,5-trinitroperhydro-1,3,5-triazine (RDX) in the presence of 160 ppb TNT was performed by sequential additions of 50 ppb of RDX, at a concentration range of 0-250 ppb. Differential pulse voltammetry fingerprints and calibration curve for [3-nitrooxy-2,2-bis(nitrooxymethyl)propyl] nitrate (PETN) was performed by sequential additions of 50 ppb of PETN, at a concentration range of 0-400 ppb.

As shown in FIG. 4A (left), during differential pulse voltammetry scan of TNT, three current peaks appeared; at −0.35 Volt, −0.90 Volt and another peak at about −0.65 Volt, that was masked by an oxygen peak. The combination of the two peaks and their shape can be used as a "fingerprint" of TNT when measured by modified carbon electrode as described herein. The calibration curve (FIG. 4A, right) shows a linear dependency of TNT concentration in a derivative of the current in respect to the voltage (dI/dE), which increased the sensitivity to 1 μA/(ppb*volt).

The nitro-amine based explosive is much more complicated target for electrochemical analysis in comparison to nitro-aromatic based explosive, due to its low volatility and the overlap of its peak with the oxygen reduction peak. By utilizing the broader electrochemical window obtained with modified carbon microelectrode described herein, the detection of nitro amine based explosive in the presence of dissolved oxygen and even in the presence of other explosives can be performed.

The detection of 1,3,5-Trinitroperhydro-1,3,5-triazine (RDX) was performed in the presence of TNT and the obtained data is shown in FIG. 4B. As shown therein, during differential pulse voltammetry scan of RDX, only one current peak appeared at −0.90 volt. The shape of the peak in the voltage combination can be used as a "finger print" of RDX when measured by the modified carbon electrode.

The detection of [3-Nitrooxy-2,2-bis(nitrooxymethyl)propyl] nitrate (PETN) was performed under the same conditions used for TNT detection, and the obtained data is shown in FIG. 4C. As shown therein, during differential pulse voltammetry scan of PETN, only one current peak appeared at −1.05 volt and its shape is different from the RDX peak. The shape of the peak in the voltage combination can be used as a "finger print" of PETN when measured by the modified micro-carbon-fibers electrode. The calibration curve (FIG. 4C, right) shows a linear dependency between the concentration of both nitrate-ester based explosive and a derivative of the current in respect to the voltage (dI/dE), which increased the sensitivity to about 2 μA/(ppb*volt).

The explosive detections were performed in 12 seconds.

As shown herein, the detection using the modified electrode of the present embodiments distinguishes between the signals coming from common nitro-aromatic explosive and those coming from common nitro-amine and nitrate-ester explosives. These capabilities are highly crucial for detection of explosives in field conditions.

Importantly, the detection of nitro-aromatic based explosives can be performed by a single short measurement.

Another advantage of the modified carbon electrode is its high stability towards the measurements conditions. The presented electrode can perform over more than 100 cycles, and has long shelf-life, of at least one month.

Example 4

Optimization of the Electrolyte Solution

Acetonitrile is an exemplary water-miscible solvent which provides for fast dissolution of nitro-containing explosive. See, for example, Sanoit et al. *Electrochim Acta* 54, 5688-5693.

For increasing the mixed background's conductivity, 0.25 M KCl was added.

In order to find the ideal conditions for sensing, detection of various concentrations of TNT was assayed at various pH values ranging from 0 to 13, as follows:

Emstat 2 potentiostat (Palmsens) was used as the electrochemical system. Electrochemical cell's volume: 1 mL; working electrode: Toray paper SGL; average size of electrode: 0.5 $cm^2$; reference electrode: Ag/AgCl in sat. KCl; counter electrode: Pt 0.4 cm2. APDMES-modified Spectracarb™ 2050A-1050 was used.

Electrochemical (linear sweep voltammetry) measurements were performed with a starting potential of −0.1V, end potential of 1.1V, and scan rate of 0.1V/second.

TNT was tested at a concentration ranging from 2 to 18, prepared from a stock solution of 200 ppm TNT.

Background solution composition was 35 mL of phosphate buffer, 15 mL of Acetonitrile, 0.5 mL KCl sat.

pH values of the background solution were as follows: 0, 1, 3, 4, 7, 9, 11, 12, and about 13.

The system was operated by introducing TNT to the electrochemical cell, and immediately thereafter mixing the background solution with pipettor in order to achieve a homogenous solution.

Table 1 below summarizes the average reduction potentials obtained for TNT at the various pH values of the electrolyte solution. Of note, only at pH 1 the first reduction of TNT was detected.

TABLE 1

| pH | V [Volts] (average) |
|---|---|
| 0 | No signal |
| 1 | 0.34, 0.69 |
| 3 | 0.43 |
| 4 | 0.51 |
| 7 | 0.52 |
| 9 | 0.52 |
| 11 | 0.50 |
| 12 | 0.54 |
| 13 | No signal |

Plots demonstrating the correlation between the current and the detected concentration of TNT (dependence $I_p=f(C)$) were generated based on the Randles-Sevcik equation: an equation that relates the current and different parameters in the half cell reaction:

$$I_p=2.69 \cdot 10^5 \cdot AD^{0.5}n^{1.5}\gamma^{0.5}C$$

wherein: n is the number of electrons participating in the redox reaction; A is the electrode area; D is the diffusion coefficient of the tested compound in the solution; C is the concentration of the analyte in the bulk solution; and γ is the potential scan rate.

The data obtained at pH 1 yielded a linear $I_p=f(C)$) plot with $R^2=0.9872$. Such a pH, however, is not ideal for performing sensing.

The data obtained at pH 3 and pH 4 also yielded linear plots.

The data obtained at pH 7 and pH 9 yielded less linear plots and suggest that the system reaches saturation at a concentration of about 10 ppm.

At higher pH values, pH 11 and 12, the solution reaches saturation already at about 6 ppm of TNT.

While considering both practical considerations, sensitivity, and linearity (which is highly useful for correlating signal to concentration), the obtained data suggest that an acidic pH is suitable for detecting nitro-containing compounds such as TNT, preferably pH lower than 5, e.g., of 2-5 or of 3-5, or of 3-4, or of 4.

Some experiments were therefore carried out using a mixed background electrolyte solution of phthalate buffer pH 4.0/acetonitrile (7/3 v/v %).

5 mM of tetrabutylammonium iodide (TBA-I) was found to improve the $O_2$ peak shape, and to assist in separating the TNT, $O_2$ and RDX peaks.

Additional experiments were conducted with an electrolyte solution comprising phosphate buffer, 50 mM, pH 6.5 as the aqueous solution, acetonitrile (3/7 ratio to the phosphate buffer), 5 mM of tetrabutylammonium perchlorate and 250 mM potassium chloride, using the same electrochemical system.

Vapors of the tested explosive were pumped into the cell, using an air pump of 10-20 liter/minute capacity, during the indicated time period.

FIGS. 5A-E present the data obtained in experiments conducted with the APDMES-modified carbon paper microelectrode, upon introduction of air during 60 seconds (FIG. 5A), introduction of TNT vapors during 15 seconds (FIG. 5B), introduction of RDX vapors during 15 seconds (FIG. 5C), and introduction of PETN vapors during 15 seconds (FIG. 5D).

FIGS. 5E-G present the data obtained in experiments conducted with plasma-treated carbon paper microelectrode (Spectracarb™ 2050A-1050), upon introduction of air during 60 seconds (FIG. 5E), introduction of TNT vapors during 15 seconds (FIG. 5F), and introduction of RDX vapors during 15 seconds (FIG. 5G).

As can be seen, much more substantial differences of the reduction peaks from the oxygen reduction peak are observed when the modified electrode was employed.

While considering practical considerations, sensitivity, linearity, and while considering that working potentials should preferably outside the electrochemical window of water, the obtained data suggest that a pH of 6.5 is also suitable for detecting nitro-containing compounds.

Additional experiments were performed also with an electrolyte solution comprising a dibasic phosphate buffer, 100 mM, pH 8.8 as the aqueous solution, acetonitrile (3/7 ratio to the phosphate buffer), 5 mM of tetrabutylammonium perchlorate and 250 mM potassium chloride, using the same electrochemical system and while introducing vapors of the tested explosive using an air pump as described hereinabove (for 1-60 seconds, e.g., 3-20 seconds).

FIG. 6 presents the data obtained in experiments conducted with the APDMES-modified carbon paper microelectrode, upon introduction TNT vapors, after the first scan (red) and after 5 scans (blue). The obtained data further support the inferior detection performance when an electrolyte solution of high pH is employed.

Example 5

Carbon Paper Microelectrode Chemically-Modified by Varying Amine-Containing Moieties Chemical modification of a carbon paper microelectrode with varying functional groups was performed in accordance with the procedure described in Example 2 hereinabove, using respective starting materials featuring the respective functional group and a silicate moiety or moieties. Measurements were performed using an electrochemical setup as described in Example 3 hereinabove.

The electrolyte solution contained 0.25 M Potassium chloride, 5 mM tetrabutylammonium perchlorate in aqueous buffer 25 mM phosphate pH 6.6/acetonitrile mix at 7/3 aqueous/organic solution volume ratio.

TNT, 1 ppm, was introduced to the cell as solution, described hereinabove. Measurements were made using a linear sweep voltammetry mode [parameters: scan rate=0.1 volt/second, E step=0.005 volt], using EmStat, and data is presented as d(current)/d(voltage) as a function of Voltage].
The obtained data is presented in FIG. 7A, and show that all tested modifications were superior to the non-modified electrode, while the aminophenyl-substituted electrode is less preferred. The obtained data further show that a different signal is generated by a different modification, thereby indicating that a fingerprint can be generated for a nitro-containing compound when an array of electrodes, each featuring a different modification, is used.

In another set of experiments, RDX, 2 ppm, was introduced to the cell as solution, and measurements were made using a square wave voltammetry mode [E step=0.005V, amplitude=0.05V, Frequency=7.0 Hz]. The obtained data is presented in FIG. 7B, and is in corroboration with the data presented in FIG. 7A Example 6

Carbon Fiber Electrodes

Various carbon paper microelectrodes and carbon fabric microelectrodes were modified with APDMES, as described in Example 2 hereinabove for gas phase preparation, and were tested in detection of TNT and RDX.

Measurements were conducted using an electrochemical set up as described in Example 3 hereinabove, using an electrolyte solution as described herein, featuring pH 6.5, and acetonitrile or ethanol as an organic solvent.

Measurements were performed upon introducing vapors of the tested sample into the cell using an air pump as described herein, during 20-30 seconds, in a linear sweep voltammetry mode.

FIGS. 8A-D present the data obtained with non-modified ELAT Hydrophilic Plain Cloth® electrode upon introducing air (FIG. 8A), and with APDMES-modified ELAT Hydrophilic Plain Cloth® electrode upon introducing air (FIG. 8B), RDX (FIG. 8C) and TNT (FIG. 8D).

FIGS. 9A-D present the data obtained with non-modified 1071 HCB Plain Carbon Cloth electrode upon introducing air (FIG. 9A), and with APDMES-modified 1071 HCB Plain Carbon Cloth electrode upon introducing air (FIG. 9B), RDX (FIG. 9C) and TNT (FIG. 9D).

FIGS. 10A-D present the data obtained with non-modified Panex 30 Carbon Fiber Fabric electrode upon introducing air (FIG. 10A), and with APDMES-modified Panex 30 Carbon Fiber Fabric electrode upon introducing air (FIG. 10B), RDX (FIG. 10C) and TNT (FIG. 10D).

FIGS. 11A-D present the data obtained with non-modified Freudenberg H23 Carbon paper electrode upon introducing air (FIG. 11A), and with APDMES-modified Sigracet 39AA Carbon paper electrode upon introducing air (FIG. 11B), RDX (FIG. 11C) and TNT (FIG. 11D).

FIGS. 12A-D present the data obtained with non-modified Sigracet 39AA Carbon paper electrode upon introducing air (FIG. 12A), and with APDMES-modified Freudenberg H23 Carbon paper electrode upon introducing air (FIG. 12B), RDX (FIG. 12C) and TNT (FIG. 12D).

The data is presented as d(current)/d(voltage) as a function of Voltage, and show that for all tested electrodes, a signal for the tested nitro-containing compound is seen separated from the oxygen peak (typically to the left of the oxygen peak, at a more negative potential).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An electrochemical cell comprising a sensing electrode, said sensing electrode being a working electrode and comprising a carbon electrode and a functional moiety covalently attached to a surface of said electrode, said functional moiety comprising an electron donating moiety and forms a charge-transfer complex with a nitro-containing compound, said functional moiety being selected from an aminoalkyl, and a silyl or siloxane substituted by an aminoalkyl, wherein said aminoalkyl is 1-10 carbon atoms in length, substituted by a —NR'R" group, wherein R' and R" are each independently hydrogen, alkyl, or cycloalkyl, the electrochemical cell being such that upon contacting said nitro-containing compound with said sensing electrode and applying potential to said sensing electrode, a change in an electrochemical parameter as a result of electrochemical reduction of one or more nitro groups of said nitro-containing compound is effected.

2. The electrochemical cell of claim 1, wherein said carbon electrode is a carbon fiber microelectrode.

3. The electrochemical cell of claim 1, wherein said carbon electrode is a carbon paper microelectrode.

4. The electrochemical cell of claim 1, wherein said carbon electrode is gas-permeable.

5. The electrochemical cell of claim 1, wherein said carbon electrode is a surface-modified carbon electrode featuring a plurality of surface reactive groups.

6. A sensing system comprising the electrochemical cell according to claim 1.

7. The sensing system of claim 6, wherein said electrochemical cell further comprises an electrolyte solution in contact with said sensing electrode.

8. The sensing system of claim 7, wherein said electrolyte features a pH lower than 8.

9. The sensing system of claim 7, wherein said electrolyte comprises a mixture of an aqueous solvent and an organic solvent.

10. The sensing system of claim 7, wherein said electrolyte comprises a quaternary ammonium salt.

11. The sensing system of claim 6, wherein said electrochemical cell is devoid of means for deaerating the electrochemical cell prior to introducing a sample to the electrochemical cell.

12. The sensing system of claim 6, further comprising a power source electrically connected to said sensing electrode.

13. The sensing system of claim 6, further comprising a device for measuring an electrochemical parameter of said sensing electrode.

14. A method of detecting a nitro-containing compound in a sample, the method comprising:
introducing the sample to the electrochemical cell according to claim 1;
applying potential to said sensing electrode; and
measuring an electrochemical parameter of said sensing electrode, wherein a presence and/or level of said parameter is indicative of a presence and/or level of the nitro-containing compound in the sample.

15. The method of claim 14, wherein said electrochemical parameter comprises an electrical current generated at said sensing electrode, wherein a presence and/or level of said electrical current is indicative of a presence and/or level of the nitro-containing compound.

16. The method of claim 14, wherein the sample comprises oxygen.

17. The method of claim 14, wherein introducing the sample to the electrochemical cell comprises contacting an electrolyte solution comprising the sample with the sensing electrode.

18. The method of claim 17, wherein a concentration of dissolved oxygen in said electrolyte is at least 1 ppm.

19. The method of claim 14, wherein said nitro-containing compound is a nitro-containing explosive.

20. The method of claim 14, being devoid of dearating the electrochemical cell prior to introducing the sample to the electrochemical cell.

* * * * *